United States Patent
Backer et al.

(10) Patent No.: US 7,157,463 B2
(45) Date of Patent: Jan. 2, 2007

(54) SUBSTITUTED PIPERIDINES/PIPERAZINES AS MELANOCORTIN RECEPTOR AGONISTS

(75) Inventors: Ryan Thomas Backer, Indianapolis, IN (US); Karin Briner, Indianapolis, IN (US); Christopher William Doecke, Indianapolis, IN (US); Matthew Joseph Fisher, Mooresville, IN (US); Steven Lee Kuklish, Fishers, IN (US); Vincent Mancuso, Thy-Le-Chateau (BE); Michael John Martinelli, Zionsville, IN (US); Jeffrey Thomas Mullaney, Indianapolis, IN (US); Chaoyu Xie, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 376 days.

(21) Appl. No.: 10/466,249

(22) PCT Filed: Jan. 23, 2002

(86) PCT No.: PCT/US02/00516

§ 371 (c)(1),
(2), (4) Date: Jul. 11, 2003

(87) PCT Pub. No.: WO02/059107

PCT Pub. Date: Aug. 1, 2002

(65) Prior Publication Data

US 2004/0058936 A1 Mar. 25, 2004

Related U.S. Application Data

(60) Provisional application No. 60/263,595, filed on Jan. 23, 2001.

(51) Int. Cl.
*A61K 31/496* (2006.01)
*C07D 401/12* (2006.01)
*C07D 403/12* (2006.01)
*C07D 403/14* (2006.01)

(52) U.S. Cl. .......................... 514/253.05; 514/254.09; 514/233.5; 514/253.13; 514/307; 514/308; 514/323; 544/121; 544/363; 544/373; 544/130; 544/360; 546/140; 546/146; 546/201

(58) Field of Classification Search ............... 544/363, 544/373, 121; 514/233.5, 253.05, 254.09
See application file for complete search history.

(56) References Cited

U.S. PATENT DOCUMENTS 6,294,534 B1    9/2001    Nargund et al. ......... 514/233.5

FOREIGN PATENT DOCUMENTS

| WO | WO 94 13696 A1 | 6/1994 |
|---|---|---|
| WO | WO 99 55679 A1 | 11/1999 |
| WO | WO 99 64002 A1 | 12/1999 |
| WO | WO 00 74679 A1 | 12/2000 |
| WO | WO 01 70337 A1 | 9/2001 |
| WO | WO 01 70708 A1 | 9/2001 |
| WO | WO 02 15909 A1 | 2/2002 |
| WO | WO 02 059095 A1 | 8/2002 |
| WO | WO 02 059108 A1 | 8/2002 |
| WO | WO 02 059117 A1 | 8/2002 |
| WO | WO 02 070511 A1 | 9/2002 |

OTHER PUBLICATIONS

Sebhat et al. Annula Reports in Medicinal Chemistry, vol. 38, p. 31-40 (2003).*
Campfield et al. Science, vol. 280, p. 1383-1387 (1998).*

* cited by examiner

*Primary Examiner*—Emily Bernhardt
(74) *Attorney, Agent, or Firm*—James B. Myers; Soonhee Jang

(57) ABSTRACT

The present invention relates to melanocortin receptor agonists of formula I, which is useful in the treatment of obesity, diabetes and male and/or female sexual dysfunction

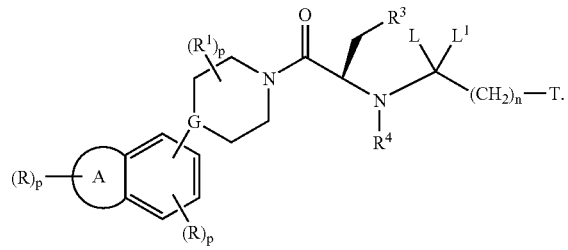

25 Claims, No Drawings

SUBSTITUTED PIPERIDINES/PIPERAZINES AS MELANOCORTIN RECEPTOR AGONISTS

REFERENCE TO RELATED APPLICATIONS

This is the national stage application, under 35 USC 371, for PCT/US02/00516, filed Jan. 23, 2002, which claims the benefit of U.S. Provisional Application Ser. No. 60/263,595, filed Jan. 23, 2001.

FIELD OF THE INVENTION

The present invention relates to melanocortin receptor agonists, and more particularly piperazine and piperdine derivatives as melanocortin receptor agonists, which are useful for the treatment or prevention of diseases and disorders responsive to the activation of melanocortin receptors.

BACKGROUND OF THE INVENTION

Pro-opiomelanocortin (POMC) derived peptides are known to affect food intake. Several lines of evidence support the notion that the G-protein coupled receptors (GPCRs) of the melanocortin receptor (MC-R) family, several of which are expressed in the brain, are targets of POMC derived peptides involved in the control of food intake and metabolism.

Evidence for the involvement of MC-R in obesity includes: i) the agouti ($A^{vy}$) mouse which ectopically expresses an antagonist of the MC-1R, MC-3R and MC-4R is obese, indicating that blocking the action of these three MC-Rs can lead to hyperphagia and metabolic disorders; ii) MC-4R knockout mice (Huszar et al., Cell, 88:131–141, 1997) recapitulate the phenotype of the agouti mouse and these mice are obese; iii) the cyclic heptapeptide MC-1R, MC-3R, MC-4R, and MC-5R agonist melanotanin-II (MT-II) injected intracerebroventricularly (ICV) in rodents, reduces food intake in several animal feeding models (NPY, ob/ob, agouti, fasted) while ICV injected SHU-9119 (MC-3R, MC-4R antagonist; MC-1R and MC-5R agonist) reverses this effect and can induce hyperphagia; and iv) chronic intraperitoneal treatment of Zucker fatty rats with an alpha-NDP-MSH derivative (HP228) has been reported to activate MC-1R, MC-3R, MC-4R and MC-5R and to attenuate food intake and body weight gain over a 12 week period.

Five MC-Rs have thus far been identified, and these are expressed in different tissues. MC-1R was initially characterized by dominant gain of function mutations at the extension locus, affecting coat color by controlling phaeomelanin to eumelanin conversion through control of tyrosinase. MC-1R is mainly expressed in melanocytes. MC-2R is expressed in the adrenal gland and represents the ACTH receptor. MC-3R is expressed in the brain, gut and placenta and may be involved in the control of food intake and thermogenesis. MC-4R is uniquely expressed in the brain and its inactivation was shown to cause obesity. (A. Kask, et al., "Selective antagonist for the melanocortin-4-receptor (HS014) increases food intake in free-feeding rats, *Biochein. Biophys. Res. Commun.*, 245:90–93, 1998). MC-5R is expressed in many tissues including white fat, placenta and exocrine glands. A low level of expression is also observed in the brain. MC-5R knock out mice reveal reduced sebaceous gland lipid production (Chen et al., *Cell*, 91:789–798, 1997).

MC-4R appears to play a role in other physiological functions as well, namely controlling grooming behavior, erection and blood pressure. Erectile dysfunction denotes the medical condition of inability to achieve penile erection sufficient for successful intercourse. The term "impotence" is often times employed to describe this prevalent condition. Synthetic melanocortin receptor agonists have been found to initiate erections in men with psychogenic erectile dysfunction (H. Wessells et al., "Synthetic Melanotropic Petide Initiates Erections in Men With Psychogenic Erectile Dysfunction: Double-Blind, Placebo Controlled Crossover Study," *J. Urol.*, 160: 389–393, 1998). Activation of melanocortin receptors of the brain appears to cause normal stimulation of sexual arousal. Evidence for the involvement of MC-R in male and/or female sexual dysfunction is detailed in WO 00/74679.

Diabetes is a disease in which a mammal's ability to regulate glucose levels in the blood is impaired because the mammal has a reduced ability to convert glucose to glycogen for storage in muscle and liver cells. In Type I diabetes, this reduced ability to store glucose is caused by reduced insulin production. "Type II Diabetes" or "non-insulin dependent diabetes mellitus" (NIDDM) is the form of diabetes, which is due to a profound resistance to insulin stimulating or regulatory effect on glucose and lipid metabolism in the main insulin-sensitive tissues, muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver. When these cells become desensitized to insulin, the body tries to compensate by producing abnormally high levels of insulin and hyperinsulemia results. Hyperinsulemia is associated with hypertension and elevated body weight. Since insulin is involved in promoting the cellular uptake of glucose, amino acids and triglycerides from the blood by insulin sensitive cells, insulin insensitivity can result in elevated levels of triglycerides and LDL which are risk factors in cardiovascular diseases. The constellation of symptoms which includes hyperinsulemia combined with hypertension, elevated body weight, elevated triglycerides and elevated LDL is known as Syndrome X.

Spiropiperidine and piperidine derivates have been disclosed in U.S. Pat. No. 6,294,534 B1, WO 01/70337, WO 00/74679 and WO 01/70708 as agonists of melanocortin receptor(s), which can be used for the treatment of diseases and disorders, such as obesity, diabetes and sexual dysfunction.

In view of the unresolved deficiencies in treatment of various diseases and disorders as discussed above, it is an object of the present invention to provide novel piperazine and piperidine derivatives, which are useful as melanocortin receptor agonists to treat obesity, diabetes, and male and female sexual dysfunction.

SUMMARY OF THE INVENTION

The present invention relates to a compound of novel piperazine and piperidine derivatives as melanocortin receptor agonists as shown formula I,

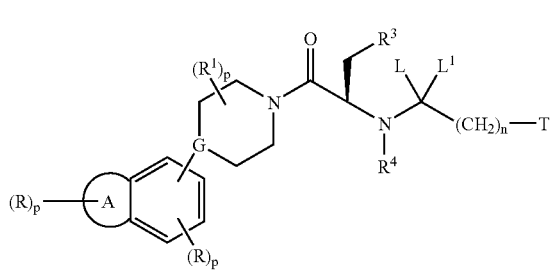

(I)

or a pharmaceutically acceptable salts or stereoisomers thereof, wherein
G is $CR^1$ or N;
L and $L^1$ are independently hydrogen or together oxo;

is a 5- or 6-membered carbocyclyl wherein the carbocyclyl being saturated, partially saturated or aromatic ring, and the carbocyclyl being optionally substituted with one to three substituents independently selected from R;
T is:

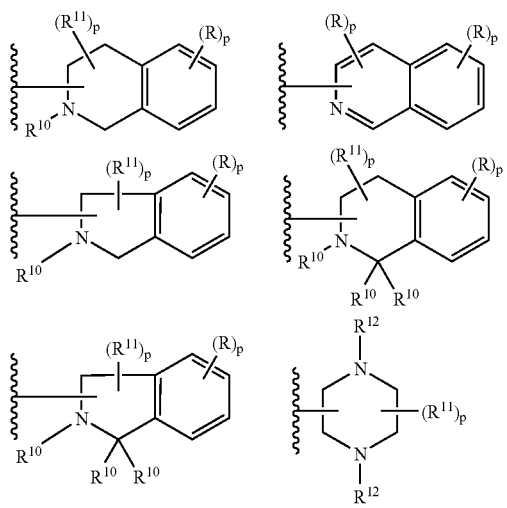

R is independently:
  hydrogen,
  hydroxy,
  (D)cyano,
  halo,
  $C_1$–$C_8$ alkyl,
  $C_1$–$C_8$ alkoxy,
  $C_3$–$C_7$ cycloalkyl,
  $C_1$–$C_4$ haloalkyl,
  (D)heterocyclyl
  (D)C(O)$R^8$,
  (D)C(O)(CH_2)_nN(R^8)_2,
  $C_1$–$C_8$ alkyl-N($R^8$)_2,
  (D)O$R^8$,
  (D)OCO$R^8$,
  (D)OC(O)N($R^8$)_2,
  (D)N($R^8$)_2,
  (D)N$R^8$C(O)$R^8$,
  (D)N$R^8$C(O)O$R^8$,
  (D)N$R^8$C(O)N($R^8$)_2,
  (D)N$R^8$SO_2$R^8$,
  (D)S$R^8$,
  (D)SO$R^8$,
  (D)SO_2$R^8$, or
  (D)SO_2N($R^8$)_2;
$R^1$ is independently:
  hydrogen, CONH($C_1$–$C_8$ alkyl), $C_1$–$C_8$ alkyl, (D)phenyl, (D)$C_3$–$C_7$ cycloalkyl or oxo, provided that oxo is not attached to the same carbon that attached to nitrogen which forms an amide bond when G is N;
$R^3$ is independently: aryl or thienyl;
wherein aryl and thienyl are optionally substituted with one to three substituents selected from the group consisting of:
  cyano, halo, $C_1$–$C_8$ alkyl, (D)$C_3$–$C_7$ cycloalkyl, $C_1$–$C_4$ alkoxy, $C_1$–$C_4$ haloalkyl and $C_1$–$C_4$ haloalkyloxy;
$R^4$ is independenly:
  hydrogen, $C_1$–$C_8$ alkyl, C(O)$R^8$, C(O)O$R^8$, $C_3$–$C_7$ cycloalkyl or (CH_2)_nO($C_1$–$C_8$ alkyl), wherein n is 2–8;
each $R^8$ is independently:
  hydrogen,
  aryl, wherein aryl being phenyl or naphthyl,
  $C_1$–$C_8$ alkyl,
  $C_1$–$C_4$ alkoxy, or
  (CH_2)_n$C_1$–$C_4$ haloalkyl, wherein n is 2–8;
each $R^{10}$ is independently:
  hydrogen, ($C_1$–$C_8$)alkyl, C(O)$C_1$–$C_8$ alkyl, aryl, or $C_3$–$C_7$ cycloalkyl;
each $R^{11}$ is independently:
  hydrogen,
  $C_1$–$C_8$ alkyl,
  aryl,
  heteroaryl
  (CH_2)_nN($R^8$)_2,
  (CH_2)_nN$R^8$C(O)$C_1$–$C_4$ alkyl,
  (CH_2)_nN$R^8$SO_2$C_1$–$C_4$ alkyl,
  (CH_2)_nSO_2N($R^8$)_2,
  (CH_2)_n[O]_q$C_1$–$C_8$ alkyl,
  (CH_2)_n[O]_q(CH_2)_nN$R^8$CO$R^8$,
  (CH_2)_n[O]_q(CH_2)_nN$R^8$SO_2$R^8$,
  (CH_2)_n[O]_q-heterocyclyl or
  (CH_2)_n[O]_q($C_1$–$C_8$ alkyl)-heterocyclyl; and
  wherein n is 2–8;
each $R^{12}$ is independently:
  hydrogen,
  $C_1$–$C_8$ alkyl,
  (D)$C_3$–$C_7$ cycloalkyl,
  (D)phenyl
  C(O)$C_1$–$C_8$ alkyl,
  C(O)phenyl,
  SO_2$C_1$–$C_8$ alkyl or
  SO_2-phenyl;
D is a bond or —(CH_2)_n—;
n is 0–8;
p is 0–4; and
q is 0–1.

The compounds of the present invention are useful in preventing or treating obesity or diabetes mellitus in a mammal comprising the administration of a therapeutically effective amount of the compound of formula I.

The compounds of the present invention are also useful in preventing or treating male or female sexual dysfunction in mammal, more specifically erectile dysfunction, comprising the administration of a therapeutically effective amount of the compound of formula I.

Also within the scope of the present invention is a pharmaceutical composition or formulation which comprises a pharmaceutical carrier and at least one compound of formula I or its pharmaceutically acceptable salts or stereoisomers thereof.

The present invention further includes a process of making a pharmaceutical composition or formulation comprising a compound of formula I or its pharmaceutically acceptable salt or stereoisomers thereof and a pharmaceutically acceptable carrier.

The present invention further includes a process of preparing a compound of formula I.

DETAILED DESCRIPTION OF THE INVENTION

The present invention relates to melanocortin receptor agonists, and more particularly piperazine and piperidine derivatives as melanocortin receptor agonists. The compounds of present invention are useful for the treatment or prevention of diseases and disorders responsive to the activation of melanocortin receptors, such as obesity, diabetes and sexual dysfunction including erectile dysfunction and female sexual dysfunction.

An embodiment of the present invention is a compound of formula I,

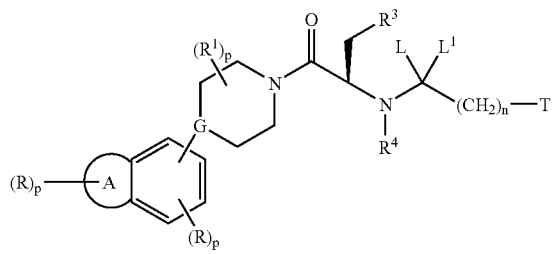

(I)

or a pharmaceutically acceptable salts or stereoisomers thereof, wherein

G is $CR^1$ or N;

L and $L^1$ are independently hydrogen or together oxo;

is a 5- or 6-membered carbocyclyl wherein the carbocyclyl being saturated, partially saturated or aromatic ring, and the carbocyclyl being optionally substituted with one to three substituents independently selected from R;

T is:

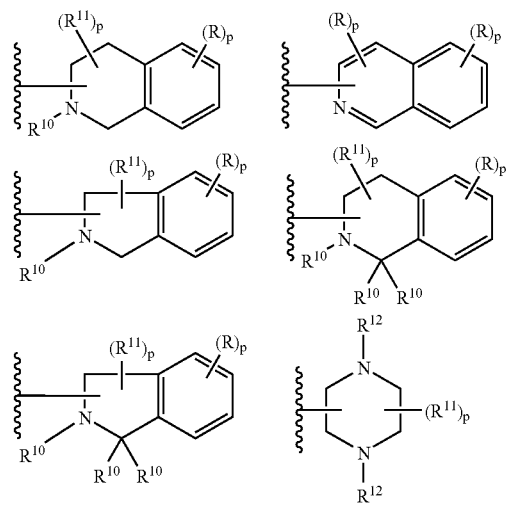

R is independently:
hydrogen,
hydroxy,
(D)cyano,
halo,
$C_1$–$C_8$ alkyl,
$C_1$–$C_8$ alkoxy,
$C_3$–$C_7$ cycloalkyl,
$C_1$–$C_4$ haloalkyl,
(D)heterocyclyl
(D)C(O)$R^8$,
(D)C(O)(CH$_2$)$_n$N($R^8$)$_2$,
$C_1$–$C_8$ alkyl-N($R^8$)$_2$,
(D)O$R^8$,
(D)OCO$R^8$,
(D)OC(O)N($R^8$)$_2$,
(D)N($R^8$)$_2$,
(D)N$R^8$C(O)$R^8$,
(D)N$R^8$C(O)O$R^8$,
(D)N$R^8$C(O)N($R^8$)$_2$,
(D)N$R^8$SO$_2$$R^8$,
(D)S$R^8$,
(D)SO$R^8$,
(D)SO$_2$$R^8$, or
(D)SO$_2$N($R^8$)$_2$;

$R^1$ is independently:
hydrogen, CONH($C_1$–$C_8$ alkyl), $C_1$–$C_8$ alkyl, (D)phenyl, (D)$C_3$–$C_7$ cycloalkyl or oxo, provided that oxo is not attached to the same carbon that attached to nitrogen which forms an amide bond when G is N;

$R^3$ is independently: aryl or thienyl;
wherein aryl and thienyl are optionally substituted with one to three substituents selected from the group consisting of: cyano, halo, $C_1$–$C_8$ alkyl, (D)$C_3$–$C_7$ cycloalkyl, $C_1$–$C_4$ alkoxy, $C_1$–$C_4$ haloalkyl and $C_1$–$C_4$ haloalkyloxy;

$R^4$ is independenly:
hydrogen, $C_1$–$C_8$ alkyl, C(O)$R^8$, C(O)O$R^8$, $C_3$–$C_7$ cycloalkyl or (CH$_2$)$_n$O($C_1$–$C_8$ alkyl), wherein n is 2–8;

each $R^8$ is independently:
hydrogen,
aryl, wherein aryl being phenyl or naphthyl,
$C_1$–$C_8$ alkyl,
$C_1$–$C_4$ alkoxy, or $(CH_2)_nC_1-C_4$ haloalkyl, wherein n is 2–8;

each $R^{10}$ is independently:
- hydrogen, $(C_1-C_8)$alkyl, $C(O)C_1-C_8$ alkyl, aryl, or $C_3-C_7$ cycloalkyl;

each $R^{11}$ is independently:
- hydrogen,
- $C_1-C_8$ alkyl,
- aryl,
- heteroaryl
- $(CH_2)_nN(R^8)_2$,
- $(CH_2)_nNR^8C(O)C_1-C_4$ alkyl,
- $(CH_2)_nNR^8SO_2C_1-C_4$ alkyl,
- $(CH_2)_nSO_2N(R^8)_2$,
- $(CH_2)_n[O]_qC_1-C_8$ alkyl,
- $(CH_2)_n[O]_q(CH_2)_nNR^8COR^8$,
- $(CH_2)_n[O]_q(CH_2)_nNR^8SO_2R^8$,
- $(CH_2)_n[O]_q$-heterocyclyl or
- $(CH_2)_n[O]_q(C_1-C_8$ alkyl)-heterocyclyl; and
wherein n is 2–8;

each $R^{12}$ is independently:
- hydrogen,
- $C_1-C_8$ alkyl,
- (D)$C_3-C_7$ cycloalkyl,
- (D)phenyl
- $C(O)C_1-C_8$ alkyl,
- C(O)phenyl,
- $SO_2C_1-C_8$ alkyl or
- $SO_2$-phenyl;

D is a bond or $—(CH_2)_n—$;

n is 0–8;

p is 0–4; and q is 0–1.

The compound of the present invention as recited above, wherein the 5- or 6-membered carbocyclyl is cyclohexyl, cyclopentyl, cyclohexenyl, cyclopentenyl or phenyl.

The compound of the present invention as recited above, wherein R is independently at each occurrence: hydrogen, halo, hydroxy, $C_1-C_8$ alkyl, $C_1-C_8$ alkoxy, $C_3-C_7$ cycloalkyl, (D)heterocyclyl, (D)C(O)$R^8$, (D)OC(O)$R^8$, (D)C(O)aryl, (D)C(O)(CH2)$_n$N(R$^8$)$_2$, (D)OC(O)(CH2)$_n$N(R$^8$)$_2$, (D)C(O)$C_1-C_4$ alkoxy, (D)N(R$^8$)$_2$, (D)NR$^8$COR$^8$, (D)NR$^8$C(O)$C_1-C_4$ alkoxy, (D)SR$^8$, (D)SO$_2$R$^8$, (D)SO$_2$N(R$^8$)$_2$ or (D)NR$^8$SO$_2$R$^8$ where R$^8$ independently at each occurrence being hydrogen, $C_1-C_8$ alkyl, $C_1-C_8$ alkoxy or phenyl.

The compound of present invention as recited above, wherein $R^3$ is phenyl optionally para-substituted with chloro, bromo, fluoro, methoxy, benzyloxy or methyl. The preferred $R^3$ is phenyl para-substituted with chloro, fluoro or methoxy.

The compound of the present invention as recited above, wherein $R^4$ is hydrogen.

The compound of the present invention as recited above, wherein $—(CH_2)_n$-T is

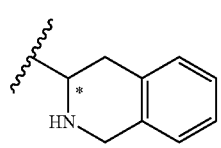 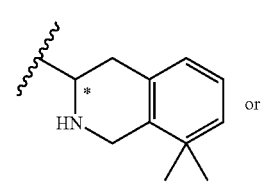 or

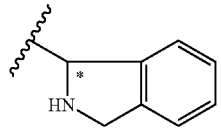

where * denotes a chiral carbon atom which has a R or S configuration.

The compound of the present invention as recited above, wherein L and $L^1$ are together oxo and the chiral carbon has R configuration.

Another embodiment of the present invention is a compound of formula II,

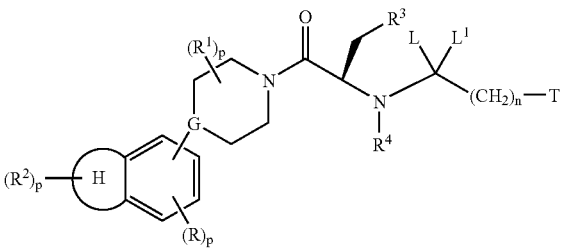

(II)

or a pharmaceutically acceptable salts or stereoisomers thereof, wherein

G is $CR^1$ or N;

L and $L^1$ are independently hydrogen or together oxo;

is a 5- or 6-membered heterocyclyl,
wherein the heterocyclyl being saturated, partially saturated or aromtic ring, provided that when G is carbon, the 5-membered nitrogen containing heterocyclyl does not contain a carbon-carbon double bond in the ring; and wherein the heterocyclyl being optionally substituted with one to three substituents independently selected from $R^2$;

T is:

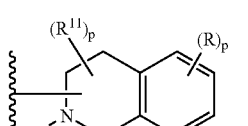 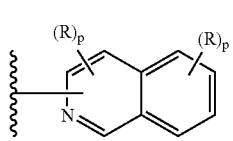

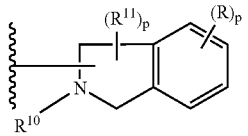 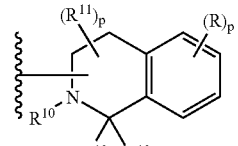

-continued

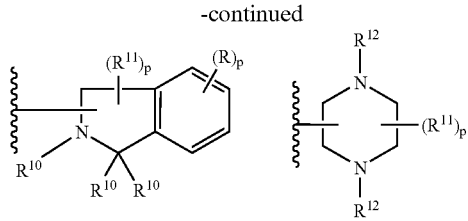

R is independently:
  hydrogen,
  hydroxy,
  (D)cyano,
  halo,
  $C_1$–$C_8$ alkyl,
  $C_1$–$C_8$ alkoxy,
  $C_3$–$C_7$ cycloalkyl,
  $C_1$–$C_4$ haloalkyl,
  (D)heterocyclyl,
  (D)C(O)$R^8$,
  (D)C(O)(CH$_2$)$_n$N($R^8$)$_2$,
  $C_1$–$C_8$ alkyl-N($R^8$)$_2$,
  (D)O$R^8$,
  (D)OCO$R^8$,
  (D)OC(O)N($R^8$)$_2$,
  (D)N($R^8$)$_2$,
  (D)N$R^8$C(O)$R^8$,
  (D)N$R^8$C(O)O$R^8$,
  (D)N$R^8$C(O)N($R^8$)$_2$,
  (D)N$R^8$SO$_2$$R^8$,
  (D)S$R^8$,
  (D)SO$R^8$,
  (D)SO$_2$$R^8$, or
  (D)SO$_2$N($R^8$)$_2$;
$R^1$ is independently:
  hydrogen, CONH($C_1$–$C_8$ alkyl), $C_1$–$C_8$ alkyl, (D)phenyl, (D)$C_3$–$C_7$ cycloalkyl or oxo, provided that oxo is not attached to the same carbon that attached to nitrogen which forms an amide bond when G is N;
$R^2$ is independently:
  hydrogen,
  $C_1$–$C_8$ alkyl,
  $C_3$–$C_7$ cycloalkyl,
  C(O)NH$_2$,
  C(O)O($C_1$–$C_6$ alkyl),
  C(O)(CH$_2$)$_n$N($C_1$–$C_6$ alkyl)$_2$,
  C(O)-phenyl,
  SO$_2$($C_1$–$C_6$ alkyl),
  SO$_2$N($C_1$–$C_6$ alkyl)$_2$,
  SO$_2$-phenyl or
  C(O)($C_1$–$C_6$ alkyl);
$R^3$ is independently: aryl or thienyl;
  wherein aryl and thienyl are optionally substituted with one to three substituents selected from the group consisting of:
  cyano, halo, $C_1$–$C_8$ alkyl, (D)$C_3$–$C_7$ cycloalkyl, $C_1$–$C_4$ alkoxy, $C_1$–$C_4$ haloalkyl and $C_1$–$C_4$ haloalkyloxy;
$R^4$ is independently:
  hydrogen, $C_1$–$C_8$ alkyl, C(O)$R^8$, C(O)O$R^8$, $C_3$–$C_7$ cycloalkyl or (CH$_2$)$_n$O($C_1$–$C_8$ alkyl), wherein n is 2–8;
each $R^8$ is independently:
  hydrogen,
  aryl, wherein aryl being phenyl or naphthyl,
  $C_1$–$C_8$ alkyl,
  $C_1$–$C_4$ alkoxy, or
  (CH$_2$)$_n$$C_1$–$C_4$ haloalkyl, wherein n is 2–8;

each $R^{10}$ is independently:
  hydrogen, ($C_1$–$C_8$)alkyl, C(O)$C_1$–$C_8$ alkyl, aryl, or $C_3$–$C_7$ cycloalkyl;
each $R^{11}$ is independently:
  hydrogen,
  $C_1$–$C_8$ alkyl,
  aryl,
  heteroaryl
  (CH$_2$)$_n$N($R^8$)$_2$,
  (CH$_2$)$_n$N$R^8$C(O)$C_1$–$C_4$ alkyl,
  (CH$_2$)$_n$N$R^8$SO$_2$$C_1$–$C_4$ alkyl,
  (CH$_2$)$_n$SO$_2$N($R^8$)$_2$,
  (CH$_2$)$_n$[O]$_q$$C_1$–$C_8$ alkyl,
  (CH$_2$)$_n$[O]$_q$(CH$_2$)$_n$N$R^8$CO$R^8$,
  (CH$_2$)$_n$[O]$_q$(CH$_2$)$_n$N$R^8$SO$_2$$R^8$,
  (CH$_2$)$_n$[O]$_q$-heterocyclyl or
  (CH$_2$)$_n$[O]$_q$($C_1$–$C_8$ alkyl)-heterocyclyl; and
  wherein n is 2–8;
each $R^{12}$ is independently:
  hydrogen,
  $C_1$–$C_8$ alkyl,
  (D)$C_3$–$C_7$ cycloalkyl,
  (D)phenyl
  C(O)$C_1$–$C_8$ alkyl,
  C(O)phenyl,
  SO$_2$$C_1$–$C_8$ alkyl or
  SO$_2$-phenyl;
D is a bond or —(CH$_2$)$_n$—;
n is 0–8;
p is 0–4; and
q is 0–1.

The compound of present invention as recited above, wherein the 5- or 6-membered heterocycly contains at least one nitrogen.

The compound of present invention as recited above, wherein the heterocyclyl is piperidinyl, pyrrolidinyl, pyrrolinyl, isoxazolyl, oxazolyl, thiazoyl, triazolyl, tetrazolyl, thiadiazolyl or oxadiazolyl.

The compound of present invention as recited above, wherein $R^3$ is phenyl optionally para-substituted with chloro, bromo, fluoro, methoxy, benzyloxy or methyl.

The compound of present invention as recited above, wherein $R^3$ is phenyl para-substituted with chloro, fluoro or methoxy.

The compound of present invention as recited above, wherein $R^4$ is hydrogen.

The compound of present invention as recited above, wherein —(CH$_2$)$_n$-T is

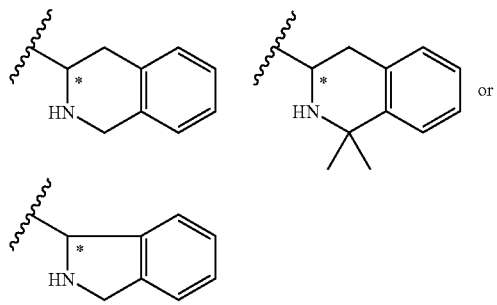

where * denotes a chiral carbon atom which has a R or S configuration.

The compound of present invention as recited above, wherein L and L¹ are together oxo and the chiral carbon has R configuration.

The preferred embodiment of the present invention provides a compound of formula III,

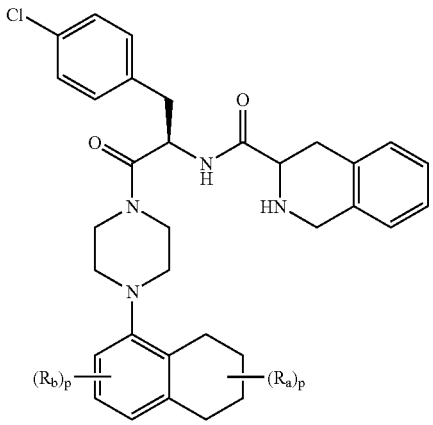

(III)

or a pharmaceutically acceptable salts or stereoisomers thereof, wherein $R_a$ is selected from the group consisting of:
  $C_1$–$C_6$ alkoxy, $NH_2$, $NH(C_1$–$C_6$ alkyl), $N(C_1$–$C_6$ alkyl)$_2$, $NHC(O)O(C_1$–$C_6$ alkyl), $N(CH_3)SO_2(C_1$–$C_6$ alkyl), $NHSO_2(C_1$–$C_6$ alkyl), $NHC(O)(C_1$–$C_6$ alkyl), $OC(O)(C_1$–$C_6$ alkyl), $OC(O)NH_2$, heterocyclyl, $C_1$–$C_6$ alkoxy, hydrogen and $C_3$–$C_7$ cycloalkyl;

$R_b$ is selected from the group consisting of:
  halo, $C_1$–$C_6$ alkyl, $N(C_1$–$C_6$ alkyl)$_2$, $C_1$–$C_4$ haloalkyl, $C_1$–$C_6$ alkoxy and hydrogen; and p is 0–4.

Another preferred embodiment of the present invention provides a compound of formula IV,

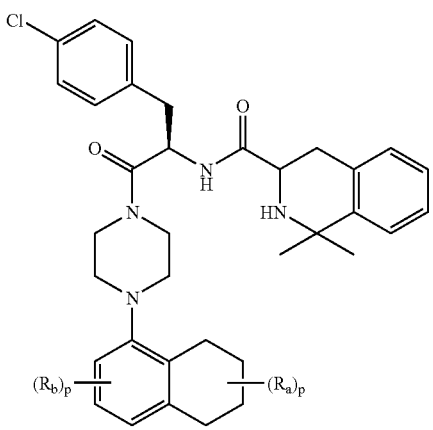

(IV)

or a pharmaceutically acceptable salts or stereoisomers thereof, wherein $R_a$ is selected from the group consisting of:
  $C_1$–$C_6$ alkoxy, $NH_2$, $NH(C_1$–$C_6$ alkyl), $N(C_1$–$C_6$ alkyl)$_2$, $NHC(O)O(C_1$–$C_6$ alkyl), $N(CH_3)SO_2(C_1$–$C_6$ alkyl), $NHSO_2(C_1$–$C_6$ alkyl), $NHC(O)(C_1$–$C_6$ alkyl), $OC(O)(C_1$–$C_6$ alkyl), $OC(O)NH_2$, heterocyclyl, $C_1$–$C_6$ alkoxy, hydrogen and $C_3$–$C_7$ cycloalkyl;

$R_b$ is selected from the group consisting of:
  halo, $C_1$–$C_6$ alkyl, $N(C_1$–$C_6$ alkyl)$_2$, $C_1$–$C_4$ haloalkyl, $C_1$–$C_6$ alkoxy and hydrogen; and p is 0–4.

Yet another preferred embodiment of the present invention provides a compound of formula V,

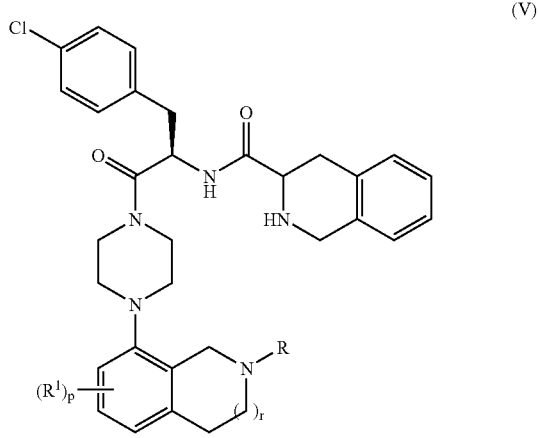

(V)

or a pharmaceutically acceptable salts or stereoisomers thereof, wherein

R is selected from the group consisting of:
  hydrogen, $C_1$–$C_6$ alkyl $C(O)NH2$, $C(O)O(C_1$–$C_6$ alkyl), $C(O)(CH_2)_nN(C_1$–$C_6$ alkyl)$_2$, $C(O)$-phenyl, $SO_2(C_1$–$C_6$ alkyl), $SO_2N(C_1$–$C_6$ alkyl)$_2$, $SO_2$-phenyl, $C(O)C_1$–$C_6$ alkyl, $C_3$–$C_7$ cycloalkyl and $(C_2$–$C_6$ alkyl)$N(C_1$–$C_6$ alkyl)$_2$;

$R^1$ is selected from the group consisting of:
  halo, $C_1$–$C_6$ alkyl, $N(C_1$–$C_6$ alkyl)$_2$, $C_1$–$C_4$ haloalkyl, hydrogen and $C_1$–$C_6$ alkoxy;

n is 0–8
p is 0–4; and
r is 0–1.

Yet another preferred embodiment of the present invention provides a compound of formula VI,

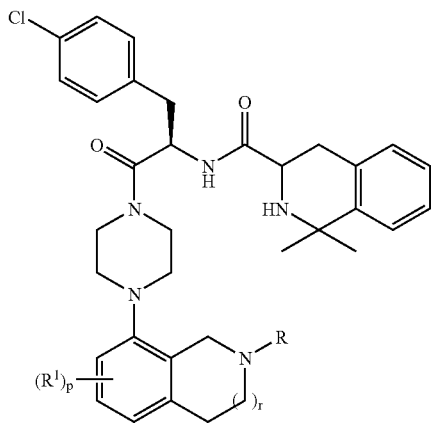

(VI)

or a pharmaceutically acceptable salts or stereoisomers thereof, wherein
R is selected from the group consisting of:
  hydrogen, $C_1$–$C_6$ alkyl, C(O)NH2, C(O)O($C_1$–$C_6$ alkyl), C(O)(CH$_2$)$_n$N($C_1$–$C_6$ alkyl)$_2$, C(O)-phenyl, SO$_2$($C_1$–$C_6$ alkyl), SO$_2$N($C_1$–$C_6$ alkyl)$_2$, SO$_2$-phenyl, C(O)$C_1$–$C_6$ alkyl, $C_3$–$C_7$ cycloalkyl and ($C_2$–$C_6$ alkyl)N($C_1$–$C_6$ alkyl)$_2$;
$R^1$ is selected from the group consisting of:
  halo, $C_1$–$C_6$ alkyl, N($C_1$–$C_6$ alkyl)$_2$, $C_1$–$C_4$ haloalkyl, hydrogen and $C_1$–$C_6$ alkoxy;
n is 0–8
p is 0–4; and
r is 0–1.

Yet another preferred embodiment of the present invention provides a compound of formula VII,

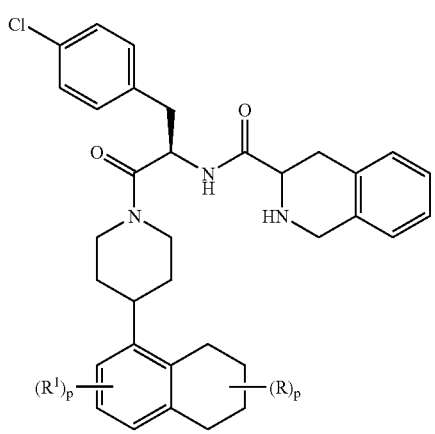

(VII)

or a pharmaceutically acceptable salts or stereoisomers thereof, wherein
R is selected from the group consisting of:
  $C_1$–$C_6$ alkoxy, NH$_2$, NH($C_1$–$C_6$ alkyl), N($C_1$–$C_6$ alkyl)$_2$, NHC(O)O($C_1$–$C_6$ alkyl), N(CH$_3$)SO$_2$($C_1$–$C_6$ alkyl), NHSO$_2$($C_1$–$C_6$ alkyl), NHC(O)($C_1$–$C_6$ alkyl), OC(O)($C_1$–$C_6$ alkyl), OC(O)NH$_2$, heterocyclyl, $C_1$–$C_6$ alkoxy, hydrogen and $C_3$–$C_7$ cycloalkyl;
$R^1$ is selected from the group consisting of:
  halo, $C_1$–$C_6$ alkyl, N($C_1$–$C_6$ alkyl)$_2$, $C_1$–$C_4$ haloalkyl, hydrogen and $C_1$–$C_6$ alkoxy; and
p is 0–4.

Yet another preferred embodiment of the present invention provides a compound of formula VIII,

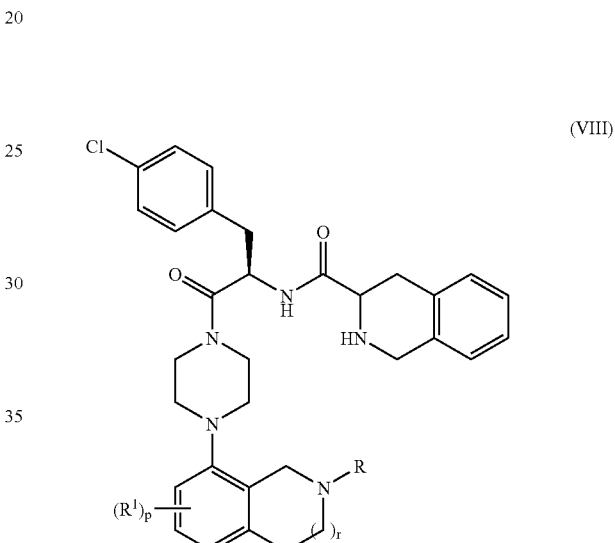

(VIII)

or a pharmaceutically acceptable salts or stereoisomers thereof, wherein
R is selected from the group consisting of:
  hydrogen, $C_1$–$C_6$ alkyl, C(O)NH2, C(O)O($C_1$–$C_6$ alkyl), C(O)(CH$_2$)$_n$N($C_1$–$C_6$ alkyl)$_2$, C(O)-phenyl, SO$_2$($C_1$–$C_6$ alkyl), SO$_2$N($C_1$–$C_6$ alkyl)$_2$, SO$_2$-phenyl, C(O)$C_1$–$C_6$ alkyl, $C_3$–$C_7$ cycloalkyl and ($C_2$–$C_6$ alkyl)N($C_1$–$C_6$ alkyl)$_2$;
$R^1$ is selected from the group consisting of:
  halo, $C_1$–$C_6$ alkyl, N($C_1$–$C_6$ alkyl)$_2$, $C_1$–$C_4$ haloalkyl, hydrogen and $C_1$–$C_6$ alkoxy;
n is 0–8
p is 0–4; and
r is 0–1.

The most preferred compound of the present invention is selected from the group consisting of:

| Name of compound | Structure of compound |
|---|---|
| 1,2,3,4-tetrahydro-isoquinoline-3-carboxylic acid{1-(4-chlorobenzyl)-2-[4-(2-methane-sulfonyl-1,2,3,4-tetra-hydro-isoquinoline-8-yl)-piperazin-1-yl]-2-oxo-ethyl}-amide | |
| 1,2,3,4-tetrahydro-isoquinoline-3-carboxylic acid{1-(4-chlorobenzyl)-2-[4-(7-diethyl-amino-5,6,7,8-tetrahydro-naphthalen-1-yl)-piperazin-1-yl]-2-oxo-ethyl}-amide | |
| 1,1-dimethyl-1,2,3,4-tetrahydro-iso-quinolin-3-carboxylic acid{1-(4-chloro-benzyl)-2-[4-(7-diethylamino-5,6,7,8-tetra-hydro-naphthalen-1-yl)-piperazin-1-yl]-2-oxo-ethyl}-amide | | and its stereoisomers

-continued

| Name of compound | Structure of compound |
|---|---|
| N-{1-(4-chloro-benzyl)-2-[4-(7-diethyl-amino-5,6,7,8-tetrahydro-naph-thalen-1-yl)-piperazin-1-yl]-2-oxo-eth-yl}-2-(1,2,3,4-tetrahydro-isoquinolin-1-yl)-acetamide | 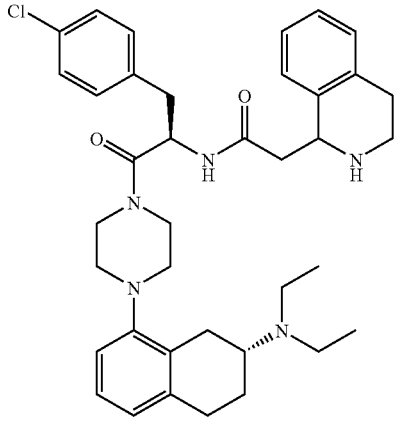<br>and its stereoisomers |
| N-{1-(4-chloro-benzyl)-2-oxo-2-[4-(7-py-ridin-1-yl-5,6,7,8-tetrahydro-naph-thalen-1-yl)-piperazin-1-yl]-ethyl}-2-(2,3-di-hydro-1H-isoindol-1-yl)-acetamide | 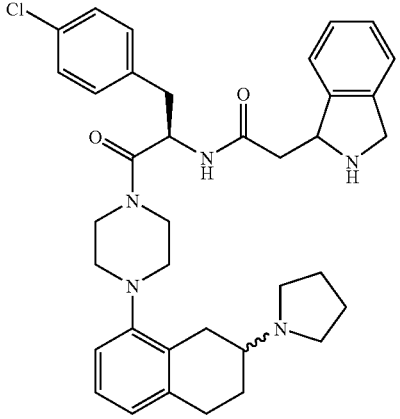<br>and its stereoisomers |

Also encompassed by the present invention is a pharmaceutical composition or formulation, which comprises a pharmaceutical carrier and at least one compound of formula I or its pharmaceutically acceptable salts or stereoisomers thereof. The pharmaceutical composition and or formulation may optionally further include a second active ingredient selected from the group consisting of an insulin sensitizer, insulin mimetic, sulfonylurea, alpha-glycosidase inhibitor, HMG-CoA reductase inhibitor, sequestrant cholesterol lowering agent, beta 3 adrenergic receptor agonist, neuropeptide Y antagonist, phosphodiester V inhibitor, and an alpha 2 adrenergic receptor antagonist.

Yet another aspect of the present invention is a process of making a pharmaceutical composition comprising a compound of formula I or its pharmaceutically acceptable salt or stereoisomers thereof as recited above and a pharmaceutically acceptable carrier.

Yet another aspect of the present invention is a method of preventing or treating obesity or diabetes mellitus in mammal comprising the administration of a therapeutically effective amount of the compound of formula I.

Yet anther aspect of the present invention is a method of preventing or treating male or female sexual dysfunction in mammal, more specifically the male or female sexual dysfunction, comprising the administration of a therapeutically effective amount of the compound of formula I.

Yet another aspect of the present invention is a process for preparing a compound of formula I:

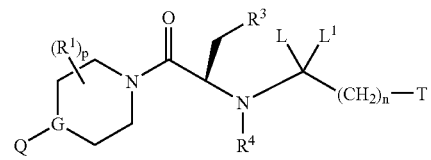

or a pharmaceutically acceptable salts or stereoisomers thereof, wherein
—CLL$^1$-(CH$_2$)$_n$-T is:

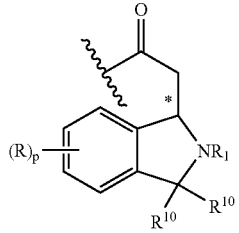

wherein R$_1$ is hydrogen, C$_1$–C$_8$ alkyl, Boc, CBZ, FMOC, phenyl or (C$_1$–C$_8$ alkyl)phenyl;
Q represents a moiety:

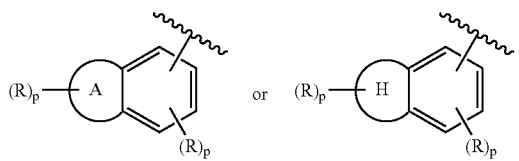

G is CR$^1$ or N;

is a 5- or 6-membered carbocyclyl wherein the carbocyclyl being saturated, partially saturated or aromatic ring, and the carbocyclyl being optionally substituted with one to three substituents independently selected from R;

is a 5- or 6-membered heterocyclyl,
wherein the heterocyclyl being saturated, partially saturated or aromtic ring, provided that when G is carbon, the 5-membered nitrogen containing heterocyclyl does not contain a carbon-carbon double bond in the ring; and
wherein the heterocyclyl being optionally substituted with one to three substituents independently selected from R$^2$;
R is independently:
  hydrogen,
  hydroxy,
  (D)cyano,
  halo,
  C$_1$–C$_8$ alkyl,
  C$_1$–C$_8$ alkoxy,
  C$_3$–C$_7$ cycloalkyl,
  C$_1$–C$_4$ haloalkyl,
  (D)heterocyclyl
  (D)C(O)R$^8$,
  (D)C(O)(CH$_2$)$_n$N(R$^8$)$_2$,
  C$_1$–C$_8$ alkyl-N(R$^8$)$_2$,
  (D)OR$^8$,
  (D)OCOR$^8$,
  (D)OC(O)N(R$^8$)$_2$,
  (D)N(R$^8$)$_2$,
  (D)NR$^8$C(O)R$^8$,
  (D)NR$^8$C(O)OR$^8$,
  (D)NR$^8$C(O)N(R$^8$)$_2$,
  (D)NR$^8$SO$_2$R$^8$,
  (D)SR$^8$,
  (D)SOR$^8$,
  (D)SO$_2$R$^8$, or
  (D)SO$_2$N(R$^8$)$_2$;
R$^1$ is independently:
  hydrogen, CONH(C$_1$–C$_8$ alkyl), C$_1$–C$_8$ alkyl, (D)phenyl, (D)C$_3$–C$_7$ cycloalkyl or oxo, provided that oxo is not attached to the same carbon that attached to nitrogen which forms an amide bond when G is N;
R$^2$ is independently:
  hydrogen,
  C$_1$–C$_8$ alkyl,
  C$_3$–C$_7$ cycloalkyl,
  C(O)NH$_2$,
  C(O)O(C$_1$–C$_6$ alkyl),
  C(O)(CH$_2$)$_n$N(C$_1$–C$_6$ alkyl)$_2$,
  C(O)-phenyl,
  SO$_2$(C$_1$–C$_6$ alkyl),
  SO$_2$N(C$_1$–C$_6$ alkyl)$_2$,
  SO$_2$-phenyl or
  C(O)(C$_1$–C$_6$ alkyl);
R$^3$ is independently: aryl or thienyl;
wherein aryl and thienyl are optionally substituted with one to three substituents selected from the group consisting of:
  cyano, halo, C$_1$–C$_8$ alkyl, (D)C$_3$–C$_7$ cycloalkyl, C$_1$–C$_4$ alkoxy, C$_1$–C$_4$ haloalkyl and C$_1$–C$_4$ haloalkyloxy;
R$^4$ is independenly:
  hydrogen, C$_1$–C$_8$ alkyl, C(O)R$^8$, C(O)OR$^8$, C$_3$–C$_7$ cycloalkyl or (CH$_2$)$_n$O(C$_1$–C$_8$ alkyl), wherein n is 2–8;
each R$^8$ is independently:
  hydrogen,
  aryl, wherein aryl being phenyl or naphthyl,
  C$_1$–C$_8$ alkyl,
  C$_1$–C$_4$ alkoxy, or
  (CH$_2$)$_n$C$_1$–C$_4$ haloalkyl, wherein n is 2–8;
each R$^{10}$ is independently:
  hydrogen, (C$_1$–C$_8$)alkyl, C(O)C$_1$–C$_8$ alkyl, aryl, or C$_3$–C$_7$ cycloalkyl;
D is a bond or —(CH$_2$)$_n$—;
n is 0–8;
p is 0–4; and
q is 0–1;
comprising the steps of:
  a) reacting a compound having a structural formula 1,

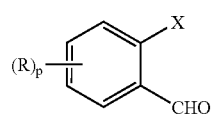

(1)

with $CH_2CH=C(O)OR^a$ wherein $R^a$ is hydrogen or $C_1$–$C_8$ alkyl and X is halo, in the presence of a catalyst and a base in a suitable organic solvent to give the compound of formula 2,

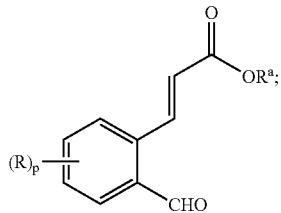

(2)

b) reductively aminating the compound of formula 2 in the presence of amine in an acidic condition to give a compound of formula 3,

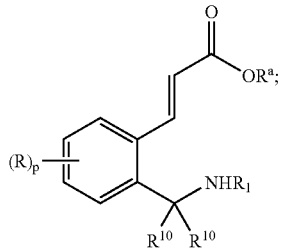

(3)

c) cyclizing the compound of formula 3 by Michael addition to give a compound of formula 4 or stereoisomers thereof,

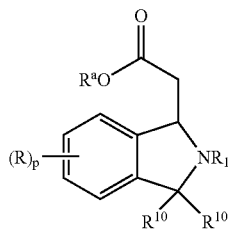

(4)

d) coupling the compound of formula 4 or stereoisomers thereof, wherein $R^a$ of compound 4 is H, with a compound of formula 5,

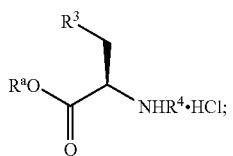

(5)

wherein $R^a$ of compound 5 is $C_1$–$C_8$ alkyl, to give a compound of formula 6;

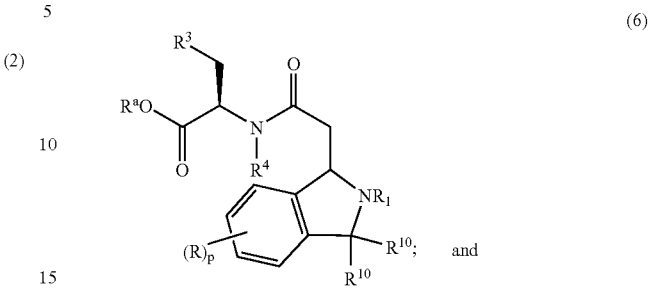

(6)

e) coupling the compound of formula 6, wherein $R^a$ is H, with a compound having a structural,

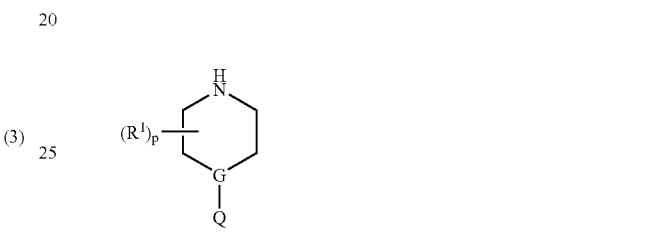

to afford the compound of formula 1.

The process of the present invention as recited above, wherein

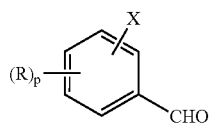

in Step (a) is 2-boromobenzaldehydes.

The process of the present invention as recited above, wherein $CH_2CH=C(O)OR$ in Step (a) is methylacrylate.

The process of the present invention as recited above, wherein the catalyst in Step (a) is selected from the group consisting of: $Pd(Ph_3P)_2Cl_2$, $Pd(Ph_3P)_4Cl_2$, $Pd(Ph_3P)_4$, $Pd(Ph_3P)_2Cl_2/CuI$, $Pd(OAc)_2/Ph_3P-Bu_4NBr$, $Pd(Ph_3P)_4Cl_2/H_2$ and $Pd(OAc)_2/P(O-tol)_3$; and wherein the base in Step (a) is $NR_3$ wherein R is hydrogen or $C_1$–$C_8$ alkyl.

The process of the present invention as recited above, wherein the amine in Step (b) is selected from the group consisting of: benzylamine, alpha-methylbenzylamine and $BocNH_2$.

The process of the present invention as recited above, wherein the Step (b) further comprises reducing of intermediate imine compound in the presence of reducing agent, the reducing agent being selected from the group consisting of: $NaCNBH_3$, $Na(OAc)_3BH$, $NaBH_4/H+$, and a combination of $Et_3SiH$ and TFA in $CH_3CN$ or $CH_2Cl_2$.

The process of the present invention as recited above, wherein the stereoisomer of compound of formula 4 in Step (c) is a compound of formula 4a.

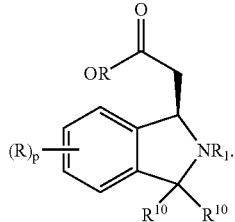

(4a)

The process of the present invention as recited above, wherein the compound of formula 4a is prepared by asymmetric hydrogenation of a compound having structural formula,

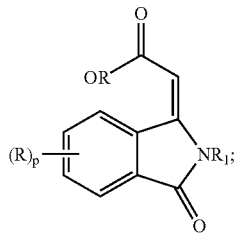

The process of the present invention as recited above, wherein the Michael addition in Step (c) is carried out in a basic workup condition.

The process of the present invention as recited above, wherein the Step (e) further comprises deprotecting or protecting of the compound of formula (4) at $NR_1$.

Yet another aspect of the present invention is a process for preparing a compound of formula I:

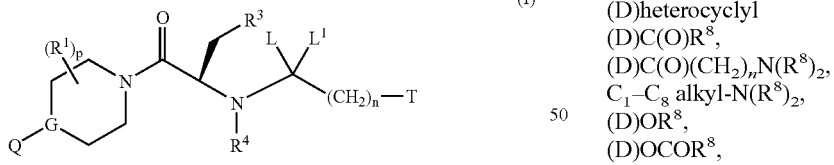

(I)

or a pharmaceutically acceptable salts or stereoisomers thereof, wherein —$CLL^1$-$(CH_2)_n$-T is:

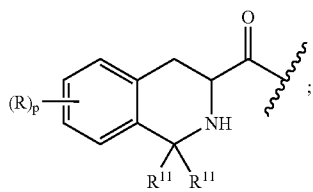

Q represents a moiety:

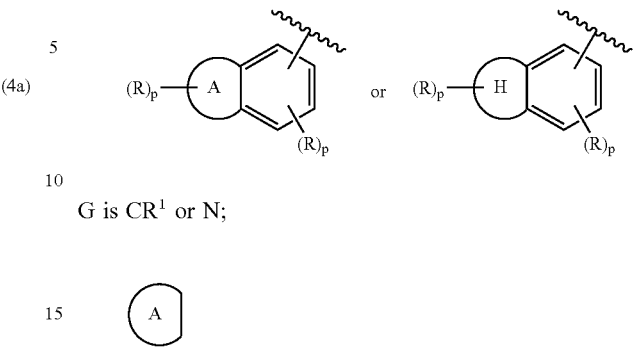

G is $CR^1$ or N;

is a 5- or 6-membered carbocyclyl wherein the carbocyclyl being saturated, partially saturated or aromatic ring, and the carbocyclyl being optionally substituted with one to three substituents independently selected from R;

(H)

is a 5- or 6-membered heterocyclyl,
  wherein the heterocyclyl being saturated, partially saturated or aromtic ring, provided that when G is carbon, the 5-membered nitrogen containing heterocyclyl does not contain a carbon-carbon double bond in the ring; and
  wherein the heterocyclyl being optionally substituted with one to three substituents independently selected from $R^2$;
R is independently:
  hydrogen,
  hydroxy,
  (D)cyano,
  halo,
  $C_1$–$C_8$ alkyl,
  $C_1$–$C_8$ alkoxy,
  $C_3$–$C_7$ cycloalkyl,
  $C_1$–$C_4$ haloalkyl,
  (D)heterocyclyl
  (D)C(O)$R^8$,
  (D)C(O)$(CH_2)_n$N$(R^8)_2$,
  $C_1$–$C_8$ alkyl-N$(R^8)_2$,
  (D)O$R^8$,
  (D)OCO$R^8$,
  (D)OC(O)N$(R^8)_2$,
  (D)N$(R^8)_2$,
  (D)N$R^8$C(O)$R^8$,
  (D)N$R^8$C(O)O$R^8$,
  (D)N$R^8$C(O)N$(R^8)_2$,
  (D)N$R^8$SO$_2R^8$,
  (D)S$R^8$,
  (D)SO$R^8$,
  (D)SO$_2R^8$, or
  (D)SO$_2$N$(R^8)_2$;
$R^1$ is independently:
  hydrogen, CONH($C_1$–$C_8$ alkyl), $C_1$–$C_8$ alkyl, (D)phenyl, (D)$C_3$–$C_7$ cycloalkyl or oxo, provided that oxo is not attached to the same carbon that attached to nitrogen which forms an amide bond when G is N;

$R^2$ is independently:
  hydrogen,
  $C_1$–$C_8$ alkyl,
  $C_3$–$C_7$ cycloalkyl,
  $C(O)NH_2$,
  $C(O)O(C_1$–$C_6$ alkyl),
  $C(O)(CH_2)_nN(C_1$–$C_6$ alkyl)$_2$,
  $C(O)$-phenyl,
  $SO_2(C_1$–$C_6$ alkyl),
  $SO_2N(C_1$–$C_6$ alkyl)$_2$,
  $SO_2$-phenyl or
  $C(O)(C_1$–$C_6$ alkyl);
$R^3$ is independently: aryl or thienyl;
wherein aryl and thienyl are optionally substituted with one to three substituents selected from the group consisting of: cyano, halo, $C_1$–$C_8$ alkyl, (D)$C_3$–$C_7$ cycloalkyl, $C_1$–$C_4$ alkoxy, $C_1$–$C_4$ haloalkyl and $C_1$–$C_4$ haloalkyloxy;
$R^4$ is independenly:
  hydrogen, $C_1$–$C_8$ alkyl, $C(O)R^8$, $C(O)OR^8$, $C_3$–$C_7$ cycloalkyl or $(CH_2)_nO(C_1$–$C_8$ alkyl), wherein n is 2–8;
each $R^8$ is independently:
  hydrogen,
  aryl, wherein aryl being phenyl or naphthyl,
  $C_1$–$C_8$ alkyl,
  $C_1$–$C_4$ alkoxy, or
  $(CH_2)_nC_1$–$C_4$ haloalkyl, wherein n is 2–8;
each $R^{11}$ is independently: hydrogen or $(C_1$–$C_8)$alkyl;
D is a bond or —$(CH_2)_n$—;
n is 0–8;
p is 0–4; and
q is 0–1;
comprising the steps of:
  a) esterifying a compound of formula 1,

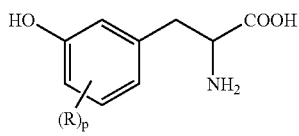

(1)

with an alcohol $R^aOH$ to form a compound of formula 2,

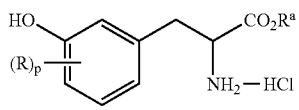

(2)

wherein $R^a$ is $C_1$–$C_4$ alkyl or (D)phenyl;

b) reacting a compound of formula 2 with $R^{11}COR^{11}$ to form a compound of formula 3,

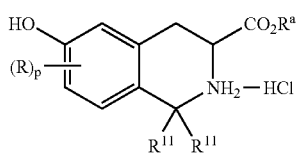

(3)

wherein $R^{11}$ is independently hydrogen or $C_1$–$C_4$ alkyl;

c) reacting a compound of formula 3 with an activating group to form a compound of formula 4,

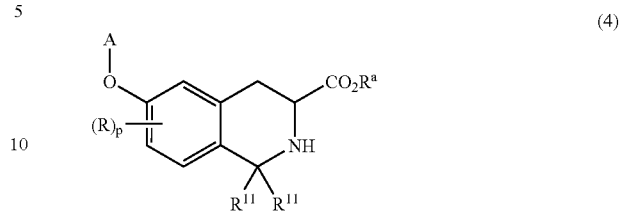

(4)

wherein A is an activating group;

d) deoxygenating the compound of formula 4 by hydrogenation to afford a compound of formula 5,

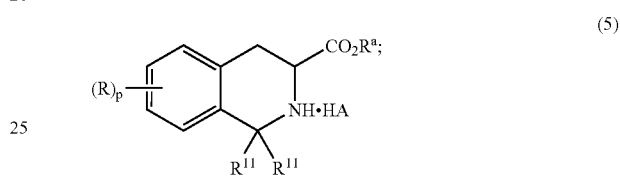

(5)

e) optionally reacting the compound of formula 5 with an inorganic base to form a compound of formula 6,

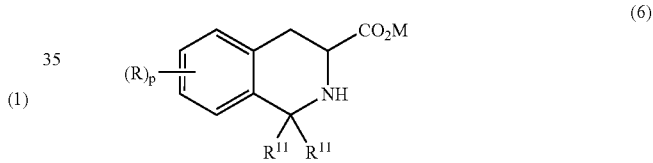

(6)

wherein HA is an acidic and M is a univalent cation;

f) resolving the compound of formula 5 or formula 6 to afford a chiral compound of formula 7,

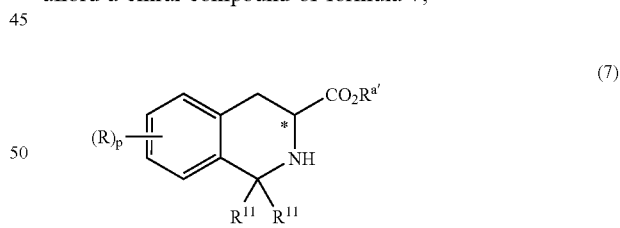

(7)

wherein M is hydrogen and $R^{a'}$ is H or $R^a$;

g) coupling the compound of formula 7 with a compound of formula 8,

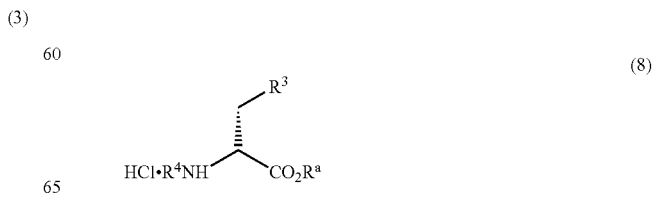

(8)

to afford a compound of formula 9,

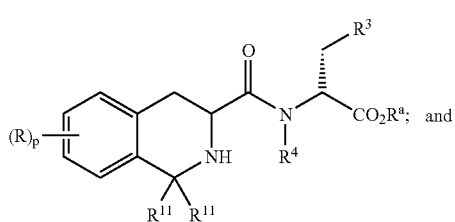

h) coupling the compound of formula 9 with a compound having a formula,

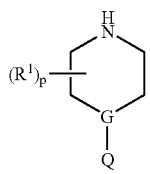

to afford a compound of formula I.

Yet another aspect of the present invention is a process for preparing a compound of formula I:

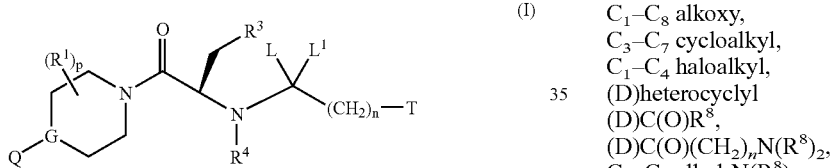

or a pharmaceutically acceptable salts or stereoisomers thereof, wherein
—CLL$^1$-(CH$_2$)$_n$-T is:

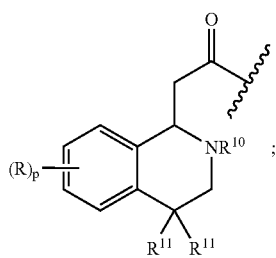

Q represents a moiety:

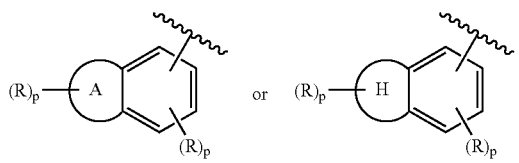

G is CR$^1$ or N;

is a 5- or 6-membered carbocyclyl wherein the carbocyclyl being saturated, partially saturated or aromatic ring, and the carbocyclyl being optionally substituted with one to three substituents independently selected from R;

is a 5- or 6-membered heterocyclyl,
wherein the heterocyclyl being saturated, partially saturated or aromtic ring, provided that when G is carbon, the 5-membered nitrogen containing heterocyclyl does not contain a carbon-carbon double bond in the ring; and
wherein the heterocyclyl being optionally substituted with one to three substituents independently selected from R$^2$;
R is independently:
hydrogen,
hydroxy,
(D)cyano,
halo,
C$_1$–C$_8$ alkyl,
C$_1$–C$_8$ alkoxy,
C$_3$–C$_7$ cycloalkyl,
C$_1$–C$_4$ haloalkyl,
(D)heterocyclyl
(D)C(O)R$^8$,
(D)C(O)(CH$_2$)$_n$N(R$^8$)$_2$,
C$_1$–C$_8$ alkyl-N(R$^8$)$_2$,
(D)OR$^8$,
(D)OCOR$^8$,
(D)OC(O)N(R$^8$)$_2$,
(D)N(R$^8$)$_2$,
(D)NR$^8$C(O)R$^8$,
(D)NR$^8$C(O)OR$^8$,
(D)NR$^8$C(O)N(R$^8$)$_2$,
(D)NR$^8$SO$_2$R$^8$,
(D)SR$^8$,
(D)SOR$^8$,
(D)SO$_2$R$^8$, or
(D)SO$_2$N(R$^8$)$_2$;
R$^1$ is independently:
hydrogen, CONH(C$_1$–C$_8$ alkyl), C$_1$–C$_8$ alkyl, (D)phenyl, (D)C$_3$–C$_7$ cycloalkyl or oxo, provided that oxo is not attached to the same carbon that attached to nitrogen which forms an amide bond when G is N;
R$^2$ is independently:
hydrogen,
C$_1$–C$_8$ alkyl,
C$_3$–C$_7$ cycloalkyl,
C(O)NH$_2$,
C(O)O(C$_1$–C$_6$ alkyl),
C(O)(CH$_2$)$_n$N(C$_1$–C$_6$ alkyl)$_2$,
C(O)-phenyl,
SO$_2$(C$_1$–C$_6$ alkyl),
SO$_2$N(C$_1$–C$_6$ alkyl)$_2$,
SO$_2$-phenyl or
C(O)(C$_1$–C$_6$ alkyl);

$R^3$ is independently: aryl or thienyl;
wherein aryl and thienyl are optionally substituted with one to three substituents selected from the group consisting of:
cyano, halo, $C_1$–$C_8$ alkyl, (D)$C_3$–$C_7$ cycloalkyl, $C_1$–$C_4$ alkoxy, $C_1$–$C_4$ haloalkyl and $C_1$–$C_4$ haloalkyloxy;
$R^4$ is independenly:
hydrogen, $C_1$–$C_8$ alkyl, C(O)$R^8$, C(O)O$R^8$, $C_3$–$C_7$ cycloalkyl or $(CH_2)_nO(C_1$–$C_8$ alkyl), wherein n is 2–8;
each $R^8$ is independently:
hydrogen,
aryl, wherein aryl being phenyl or naphthyl,
$C_1$–$C_8$ alkyl,
$C_1$–$C_4$ alkoxy, or
$(CH_2)_nC_1$–$C_4$ haloalkyl, wherein n is 2–8;
each $R^{10}$ is independently:
hydrogen, $(C_1$–$C_8)$alkyl, C(O)$C_1$–$C_8$ alkyl, aryl, $C_3$–$C_7$ cycloalkyl, or protecting group selected from Boc, CBZ or FMOC;
each $R^{11}$ is independently: hydrogen or $C_1$–$C_8$alkyl;
D is a bond or —$(CH_2)_n$—;
n is 0–8;
p is 0–4; and
q is 0–1;
comprising the steps of:
a) reacting a compound formula 1:

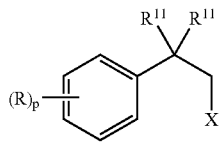

(1)

wherein X is halo, and $R^{11}$ is independently, hydrogen or C1–C4 alkyl, with CNCH$_2$CO$_2$R$^a$ wherein R$^a$ is $C_1$–$C_8$ alkyl or benzyl to afford a compound of formula 2:

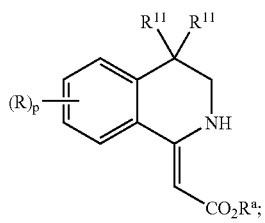

(2)

b) protecting the compound of formula 2 to form the compound of formula 3:

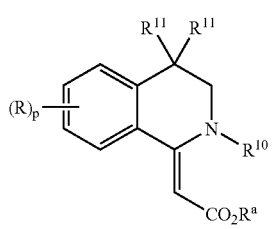

(3)

c) hydrogenating the compound of formula 3 to afford a compound of formula 4:

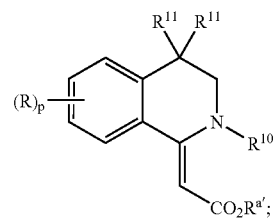

(4)

d) coupling the compound of formula 4 wherein R$^{a'}$ is hydrogen or R$^a$, with a compound of formula 5,

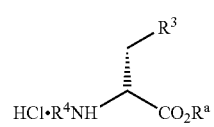

(5)

to afford a compound of formula 6,

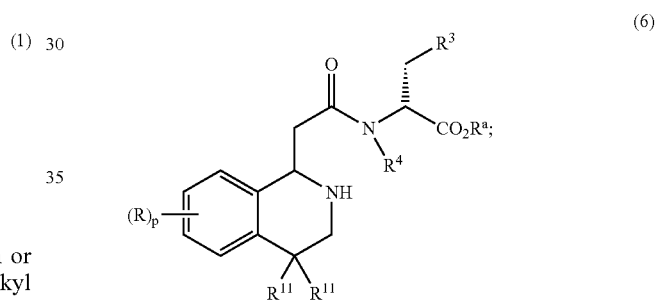

(6)

e) coupling the compound of formula 6 with a compound having a formula,

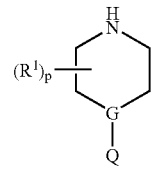

to afford a compound of formula I.

Throughout the instant application, the following terms have the indicated meanings:

The term "5- or 6-membered carbocycly" refers to carbocycly ring that is saturated, partially saturated or aromatic ring. The saturated carbocyclyl ring includes 5-or 6-membered cycloalkyl, which may be optionally substituted with other hydrocarbon substituents. Examples of cycloalkyl are cyclopentyl and cyclohexyl, and cycloalkyl as defined above may be optionally substituted with designated number of substituents as set forth in the embodiment recited above.

The partially saturated carbocycly ring includes 5- or -6 membered cycloalkenyl, which may be optionally substituted with other hydrocarbon substituents. Examples of cycloalkenyl are cyclopentenyl and cyclohexenyl, and cycloalkenyl as defined above may be optionally substituted with designated number of substituents as set forth in the embodiment recited above.

The aromatic carbocycly ring refers to 5- or 6-membered aromatic ring such as phenyl.

The "5- or 6-membered heterocyclyl" refers to a heterocyclic ring that is saturated, partially saturated or aromatic ring (i.e., heteroaryl) containing from one to four heteroatoms selected from N, O or S. The "heterocycly" includes "nitrogen containing heterocyclyl," which contains from one to four nitrogen atoms and optionally further contains one other heteroatom selected from O or S. Heterocyclyl as defined above may be optionally substituted with designated number of substituents as set forth in the embodiment recited above. The examples of 5- or 6-membered heterocyclyl includes, but are not limited to: piperidinyl, pyrrolidinyl, pyrrolinyl, isoxazolyl, oxazolyl, thiazoyl, triazolyl, tetrazolyl, thiadiazolyl, or oxadiazolyl, furanyl, thienyl, thiazolyl, isoxazoyl, imidazolyl, oxazoyl, isoxazolyl, pyrazoyl, pyrrolyl, pyrazinyl, pyridyl, pyrimidyl, and purinyl and the like.

The term "alkyl," unless otherwise indicated, refers to those alkyl groups of a designated number of carbon atoms of either a straight or branched saturated configuration. Examples of "alkyl" includes, but are not limited to methyl, ethyl, n-propyl, isopropyl, n-butyl, isobutyl, sec-butyl and t-butyl, pentyl, hexyl, neopenyl, isopentyl and the like. Alkyl as defined above may be optionally substituted with a designated number of substituents as set forth in the embodiment recited above.

The term "alkenyl" means hydrocarbon chain of a specified number of carbon atoms of either a straight or branched configuration and having at least one carbon-carbon double bond, which may occur at any point along the chain, such as ethenyl, propenyl, butenyl, pentenyl, vinyl, alkyl, 2-butenyl and the like. Alkenyl as defined above may be optionally substituted with designated number of substituents as set forth in the embodiment recited above.

The term "haloalkyl" is an alkyl group of indicated number of carbon atoms, which is substituted with one to five halo atoms selected from F, Br, Cl and I. An example of a haloalkyl group is trifluoromethyl.

The term "alkoxy" represents an alkyl group of indicated number of carbon atoms attached through an oxygen bridge, such as methoxy, ethoxy, propoxy, isopropoxy, butoxy, tert-butoxy, pentoxy, and the like. Alkoxy as defined above may be optionally substituted with a designated number of substituents as set forth in the embodiment recited above.

The term "cycloalkyl" refers to a ring composed of 3 to 7 methylene groups, each of which may be optionally substituted with other hydrocarbon substituents. Examples of cycloalkyl includes, but are not limited to: cyclopropyl, cyclobutyl, cyclopentyl, cyclohexyl and cycloheptyl, and the like. Cycloalkyl as defined above may be optionally substituted with a designated number of substituents as set forth in the embodiment recited above.

The term "halo" refers to fluoro, chloro, bromo and iodo.

The term "haloalkyloxy" represents a haloalkyl group of indicated number of carbon atoms attached through an oxygen bridge, such as $OCF_3$. "Haloalkyloxy" as defined above may be optionally substituted with a designated number of substituents as set forth in the embodiment recited above.

The term "aryl" refers to phenyl, naphthyl, anthracenyl, phenanthrenyl and the like which is optionally substituted with a designated number of substituents as set forth in the embodiment recited above.

The term "heteroaryl" refers to monocyclic or bicyclic aromatic ring of 5- to 10-carbon atoms containing from one to four heteroatoms selected from O, N, or S, and the heteroaryl being optionally substituted with a designated number of substituents as set forth in the embodiment recited above. Examples of heteroaryl are, but are not limited to furanyl, thienyl, thiazolyl, imidazolyl, isoxazoyl, oxazoyl, pyrazoyl, pyrrolyl, pyrazinyl, pyridyl, pyrimidyl, and purinyl, cinnolinyl, benzothienyl, benzotriazolyl, benzoxazolyl, quinoline, isoquinoline and the like.

The "heterocyclyl" is defined as a monocyclic, bicyclic, or tricyclic ring of 5 to 14 carbon atoms which are saturated or partially saturated containing from one to four heteroatoms selected from N, O or S. The "heterocycly" includes "nitrogen containing heterocyclyl," which contains from one to four nitrogen atoms and optionally further contains one other heteroatom selected from O or S. Heterocyclyl as defined above may be optionally substituted with a designated number of substituents as set forth in the embodiment recited above.

A mammal as used in here includes a human and a warm-blooded animal such as a cat, a dog and the like.

The term "composition" or "formulation", as in pharmaceutical composition or formulation, is intended to encompass a product comprising the active ingredient(s), and the inert ingredient(s) that make up the carrier. Accordingly, the pharmaceutical compositions of the present invention encompass any composition made by admixing a compound of the present invention (a compound of formula I) and a pharmaceutically acceptable carrier.

The term "pharmaceutical" when used herein as an adjective means substantially non-deleterious to the recipient mammal.

The term "unit dosage form" refers to physically discrete units suitable as unitary dosages for human subjects and other non-human animals such as warm-blooded animals each unit containing a predetermined quantity of active ingredient (a compound of formula I) calculated to produce the desired therapeutic effect in association with a suitable pharmaceutical carrier.

The term "treating" or "preventing" as used herein includes its generally accepted meanings, i.e., preventing, prohibiting, restraining, alleviating, ameliorating, slowing, stopping, or reversing the progression or severity of a pathological condition, or sequela thereof as described herein.

"Erectile dysfunction" is a disorder involving the failure of a male mammal to achieve erection, ejaculation, or both. Symptoms of erectile dysfunction include an inability to achieve or maintain an erection, ejaculatory failure, premature ejaculation, and the inability to achieve an orgasm. An increase in erectile dysfunction is often associated with age and is generally caused by a physical disease or as a side effect of drug treatment.

"Female sexual dysfunction" encompasses, without limitation, conditions such as a lack of sexual desire and related arousal disorders, inhibited orgasm, lubrication difficulties, and vaginismus.

Because certain compounds of the invention contain an acidic moiety (e.g., carboxy), the compound of formula I may exist as a pharmaceutical base addition salt thereof. Such salts include those derived from inorganic bases such as ammonium and alkali and alkaline earth metal hydroxides, carbonates, bicarbonates and the like, as well as salts derived from basic organic amines such as aliphatic and aromatic amines, aliphatic diamines, hydroxy alkamines, and the like.

Because certain compounds of the invention contain a basic moiety (e.g., amino), the compound of formula I can also exist as a pharmaceutical acid addition salt. Such salts include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, heptanoate, propiolate, oxalate, malonate, succinate, suberate, sebacate, fumarate, maleate, 2-butyne-1,4 dioate, 3-hexyne-2,5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, beta-hydroxybutyrate, glycollate, maleate, tartrate, methanesulfonate, propanesulfonate, naphthalene-1-sulfonate, naphthalene-2-sulfonate, mandelate and the like salts. Preferred salt form of compound of formula I is an acid addition salts, more specifically hydrochloride salt.

Some of the compounds described herein may exist as tautomers such as keto-enol tautomers. The individual tautomers as well as mixtures thereof are encompassed within the scope of the present invention.

Utility

Compounds of formula I are effective as melanocortin receptor modulators, particularly as agonists of the human MC-4 receptor. As melanocortin receptor agonists, the compounds of formula I are useful in the treatment of diseases, disorders or conditions responsive to the activation of one or more of the melanocortin receptors including, but not limited to, MC-1, MC-2, MC-3, MC-4, and MC-5. Diseases, disorders or conditions receptive to treatment with a MC-4 agonist include those mentioned above and those described in WO 00/74679, the teachings of which are herein incorporated by reference. In particular diseases, disorders or conditions receptive to treatment with a MC-4 agonist include obesity or diabetes mellitus, male or female sexual dysfunction, more specifically erectile dysfunction.

When describing various aspects of the present compounds of formula I, the terms "A domain", "B domain" and "C domain" are used below. This domain concept is illustrated below:

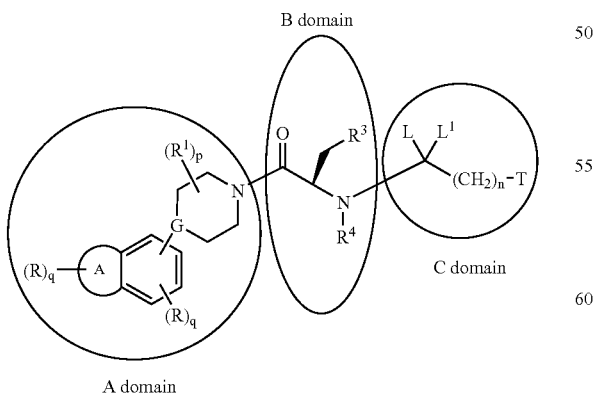

A domain

The following listing provides some of examples "A domain", "B domain" and "C domain" of the compound of formula I. These listings are provided as illustrative purposes and as such are not meant to be limiting.

EXAMPLES OF "A DOMAIN"

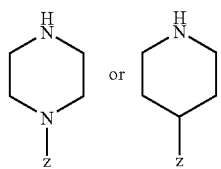

where Z is shown in the table below:

| Z |
| --- |
| 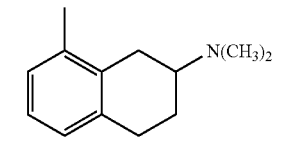 |
| 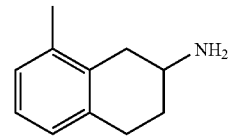 |
| 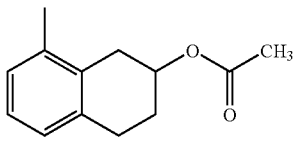 |
| 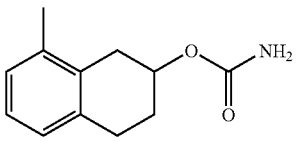 |
| 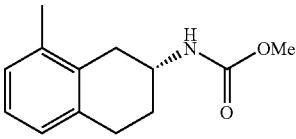 |
| 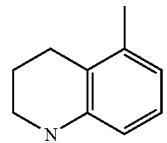 |
| 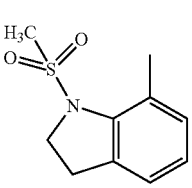 |

-continued
| Z |
|---|
| 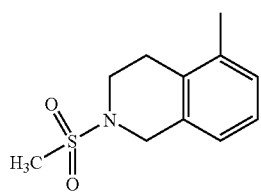 |
| 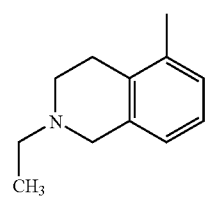 |
| 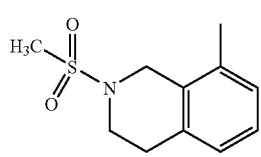 |
| 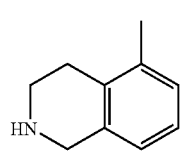 |
| 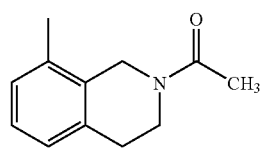 |
| 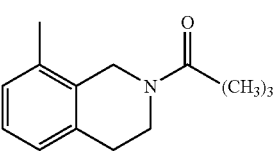 |
| 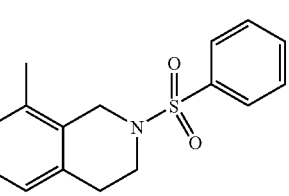 |
| 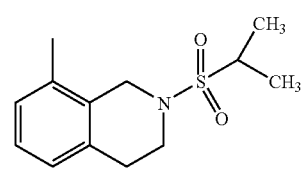 |
| 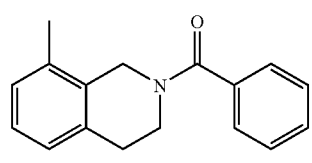 |
-continued
| Z |
|---|
| 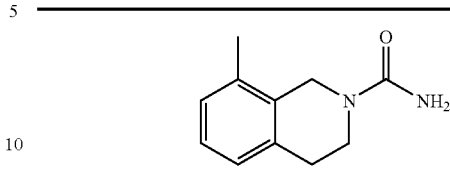 |
| 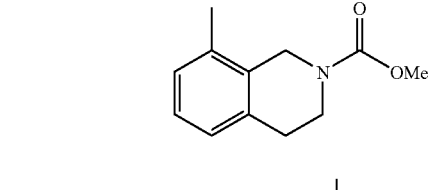 |
| 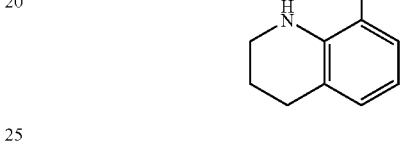 |
| 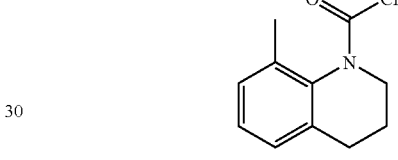 |
| 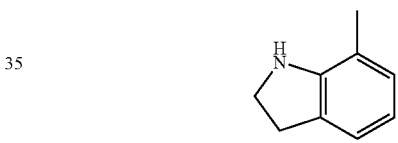 |
| 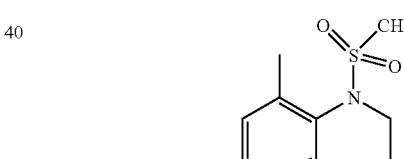 |
| 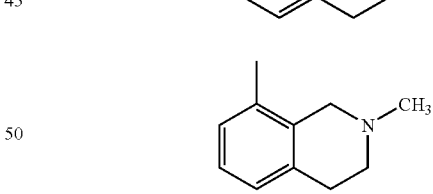 |
EXAMPLES OF "B DOMAIN"
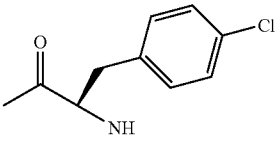

-continued

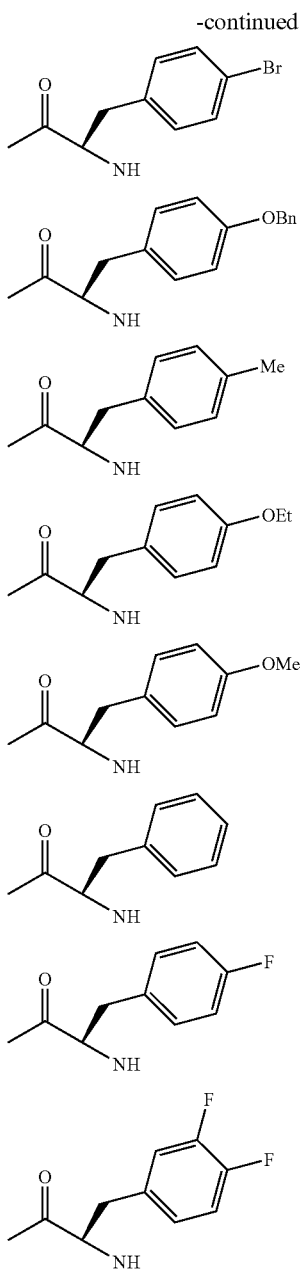

EXAMPLES OF C DOMAIN

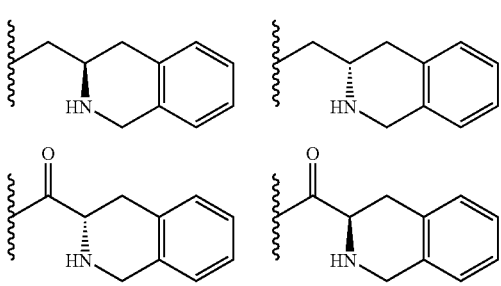

-continued

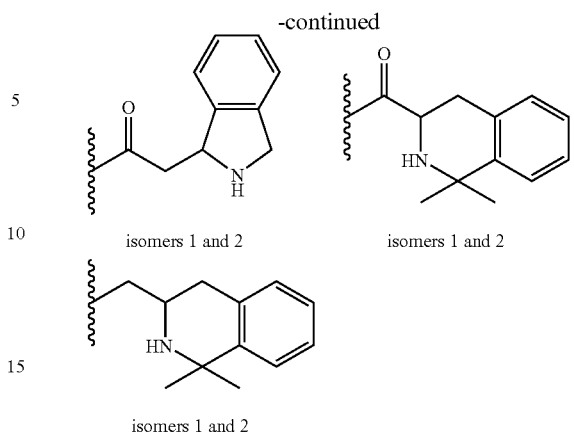

isomers 1 and 2      isomers 1 and 2 isomers 1 and 2

Formulation

The compound of formula I is preferably formulated in a unit dosage form prior to administration. Accordingly the present invention also includes a pharmaceutical composition comprising a compound of formula I and a suitable pharmaceutical carrier.

The present pharmaceutical compositions are prepared by known procedures using well-known and readily available ingredients. In making the formulations of the present invention, the active ingredient (a compound of formula I) is usually mixed with a carrier, or diluted by a carrier, or enclosed within a carrier, which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

Dosage:

The specific dose administered is determined by the particular circumstances surrounding each situation. These circumstances include, the route of administration, the prior medical history of the recipient, the pathological condition or symptom being treated, the severity of the condition/symptom being treated, and the age and sex of the recipient. Additionally, it would be understood that the therapeutic dosage administered can be determined by the physician in the light of the relevant circumstances.

Generally, an effective minimum daily dose of a compound of formula I is about 1, 5, 10, 15, or 20 mg. Typically, an effective maximum dose is about 500, 100, 60, 50, or 40 mg. The suitable dose may be determined in accordance with the standard practice in the medical arts of "dose titrating" the recipient, which involves administering a low dose of the compound initially and then gradually increasing the does until the desired therapeutic effect is observed.

Route of Administration

The compounds may be administered by a variety of routes including the oral, rectal, transdermal, subcutaneous, topical, intravenous, intramuscular or intranasal routes.

Combination Therapy

Compounds of formula I may be used in combination with other drugs that are used in the treatment of the diseases or conditions for which compounds of formula I are useful. Such other drugs may be administered by a route and in an amount commonly used therefore, contemporaneously or sequentially with a compound of formula I. When a compound of formula I is used contemporaneously with one or more other drugs, a pharmaceutical composition containing such other drugs in addition to the compound of formula I is preferred. Accordingly, the pharmaceutical compositions of the present invention include those that also contain one or more other active ingredients in addition to a compound of formula I. Examples of other active ingredients that may be combined with a compound of formula I, either administered separately or in the same pharmaceutical compositions, include but are not limited to:

(a) insulin sensitizers including (i) PPAR-gamma agonists such as the glitazones (e.g., troglitazone, pioglitazone, englitazone, MCC-555, BRL49653 and the like) and compounds disclosed in WO97/27857, WO 97/28115, WO 97/28137 and WO97/27847; (ii) biguanides such as metformin and phenformin;
(b) insulin or insulin mimetics;
(c) sulfonylureas such as tolbutamide and glipizide;
(d) alpha-glucosidase inhibitors (such as acarbose),
(e) cholesterol lowering agents such as (i) HMG-CoA reductase inhibitors (lovastatin, simvastatin and pravastatin, fluvastatin, atorvastatin, and other statins), (ii) sequestrants (cholestyramine, colestipol and a dialkylaminoalkyl derivatives of a cross-linked dextran), (iii) nicotinyl alcohol nicotinic acid or a salt thereof, (iv) proliferator-activater receptor alpha-agonists such as fenofibric acid derivatives (gemfibrozil, clofibrat, fenofibrate and benzafibrate), (v) inhibitors of cholesterol absorption such as beta-sitosterol and acyl CoA:cholesterol acyltransferase inhibitors such as melinamide, (vi) probucol, (vii) vitamin E, and (viii) thyromimetics;
(f) PPAR-delta agonists such as those disclosed in WO97/28149;
(g) antiobesity compounds such as fenfluramine, dexfenfluramine, phentermine, sibutramine, orlistat, and beta-3 adrenergic receptor agonists;
(h) feeding behavior modifying agents such as neuropeptide Y antagonists (e.g., neuropeptide Y5) as disclosed in WO 97/19682, WO 97/20820, WO 97/20821, WO 97/20822 and WO 97/20823;
(i) PPAR-alpha agonists as described in WO 97/36579;
(j) PPAR-gamma antagonists as described in WO97/10813;
(k) serotonin reuptake inhibitors, such as fluoxetine, sertraline and 5HT2C agonists;
(l) growth hormone secretagogues such as MK-0677 and gerelin antagonists; and
(m) agents useful in the treatment of male and/or female sexual dysfunction, such as phosphodiester V inhibitors including sildenafil and ICI-351, and alpha-2 adrenergic receptor antagonists including phentolamine mesylate; and dopamine-receptor agonists such as apomorphine, and MC3R, MCH, His3, leptin and opiods.

Biological Assays

A. Binding Assay:

The radioligand binding assay is used to identify competitive inhibitors of $^{125}$I-NDP-alpha-MSH binding to cloned human MCRs using membranes from stably transfected human embryonic kidney (HEK) 293 cells.

HEK 293 cells transfected with human or rat melanocortinin receptors are grown either as adherent monolayers or suspension culture. Monolayer cells are grown in roller bottle cultures at 37° C. and 5% $CO_2$/air atmosphere in a 3:1 mixture of Dulbecco's modified Eagle medium (DMEM) and Ham's F12 containing 25 mM L-glucose, 100 units/ml penicillin G, 100 microgram/ml streptomycin, 250 nanogram/ml amphoterin B, 300 microgram/ml genticin and supplemented with 5% fetal bovine serum. Monolayer cells are adapted to suspension culture (Berg et al., *Biotechniques* Vol. 14, No. 6, 1993) and are grown in either spinner or shaker flasks (37° C. and 7.5% $CO_2$/air overlay) in a modified DME/F12 medium containing 0.1 mM $CaCl_2$, 2% equine serum and 100 microgram/ml sodium heparin to prevent cell-cell aggregation. Cells are harvested by centrifugation, washed in PBS, and pellets are stored frozen at −80° C. until membrane preparations.

The cell pellets are resuspended in 10 volumes of membrane preparation buffer (i.e., 1 g pellet to 10 ml buffer) having the following composition: 50 mM Tris pH 7.5 @ 4° C., 250 mM sucrose, 1 mM $MgCl_2$, Complete® EDTA-free protease inhibitor tablet (Boehringer Mannheim), and 24 micrograms/ml DNase I (Sigma, St. Louis, Mo.). The cells are homogenized with a motor-driven dounce using 20 strokes, and the homogenate is centrifuged at 38,000×g at 4° C. for 40 minutes. The pellets are resuspended in membrane preparation buffer at a concentration of 2.5–7.5 mg/ml and 1 milliliter aliquots of membrane homogenates are quickly frozen in liquid nitrogen and then stored at −80° C.

Solutions of a compound of formula I (300 picomolar to 30 micromolar) or unlabelled NDP-alpha-MSH (1 picomolar to 100 nanomolar) are added to 150 microliters of membrane binding buffer to yield final concentrations (listed in parentheses). The membrane binding buffer has the following composition: 25 mM HEPES pH 7.5; 10 mM $CaCl_2$; 0.3% BSA). One hundred fifty microliters of membrane binding buffer. containing 0.5–5.0 microgram membrane protein is added, followed by 50 nanomolar $^{125}$I-NDP-alpha-MSH to final concentration of 100 picomolar. Additionally, fifty microliters of SPA beads (5 mg/ml) are added and the resulting mixture is agitated briefly and incubated for 10 hours at r.t. The radioactivity is quantified in a Wallace Trilux Microplate Scintillation counter. $IC_{50}$ values obtained in competition assays are converted to affinity constants ($K_i$ values) using the Cheng-Prusoff equation: $K_i=IC_{50}/(1+D/K_d)$.

B. Functional Assay:

Functional cell based assays are developed to discriminate agonists and antagonists.

Agonist Assay: HEK 293 cells stably expressing a human melanocortin receptor (see e.g., Yang, et al., *Mol-Endocrinol.*, 11(3): 274–80, 1997) are dissociated from tissue culture flasks using a trypsin/EDTA solution(0.25%; Life Technologies, Rockville, Md.). Cells are collected by centrifugation and resuspended in DMEM (Life Technologies, Rockville, Md.) supplemented with 1% L-glutamine and 0.5% fetal bovine serum. Cells are counted and diluted to 4.5×10$^5$/ml.

A compound of formula I is diluted in DMSO ($3\times10^{-5}$ to $3\times10^{-10}$ M final concentrations) and 0.05 volume of compound solution is added to 0.95 volumes of cell suspension; the final DMSO concentration is 0.5%. After incubation at 37° C./5% $CO_2$ for 5 hours, cells are lysed by addition of luciferin solution (50 mM Tris, 1 mM $MgCl_2$, 0.2% Triton-X100, 5 mM DTT, 500 micromolar Coenzyme A, 150 micromolar ATP, and 440 micromolar luciferin) to quantify the activity of the reporter gene luciferase, an indirect measurement of intracellular cAMP production.

Luciferase activity is measured from the cell lysate using a Wallace Victor 2 luminometer. The amount of lumen production which results from a compound of formula I is compared to that amount of lumens produced in response to NDP-alpha-MSH, defined as a 100% agonist, to obtain the relative efficacy of a compound. The $EC_{50}$ is defined as the compound concentration that results in half maximal stimulation, when compared to its own maximal level of stimulation.

Antagonist assay: Antagonist activity is defined as the ability of a compound to block lumen production in response to NDP-alpha-MSH. Concentration-response curves are generated for NDP-alpha-MSH in the absence and presence of a fixed concentration of a solution of a compound of formula I ($10\times K_i$ from binding assays). Suspensions of MCR-expressing cells are prepared and are incubated with NDP-alpha-MSH and compound solutions for 5 hours as described above. The assay is terminated by the addition of luciferin reagent and lumen production is quantified. Antagonist potency is determined from the rightward shift of the $EC_{50}$ value in the absence of a compound of formula I using the equation: $K_b$=Concentration of Antagonist/$[(EC_{50}'/EC_{50})-1]$.

Whole Cell cAMP Accumulation Assay

Compound Preparation

In the agonist assay, compounds are prepared as 10 mM and NDP-alpha-MSH (control) as 33.3 µM stock solutions in 100% DMSO. These are serially diluted in 100% DMSO. The compound plate is further diluted 1:200 in compound dilution buffer (HBSS-092, 1 mM Ascorbic Acid, 1 mM IBMX, 0.6% DMSO, 0.1% BSA). The final concentration range being 10 µM-100 pM for compound and 33.33 nM–0.3 pM for control in 0.5% DMSO. Transfer 20 µl from this plate into four PET 96-well plates (all assays are performed in duplicate for each receptor).

Cell Culture and Cell Stimulation

HEK 293 cells stably transfected with the MC3R and MC4R were grown in DMEM containing 10% FBS and 1% Antibiotic/Antimycotic Solution. On the day of the assay the cells were dislodged with enzyme free cell dissociation solution and resuspended in cell buffer (HBSS-092, 0.1% BSA, 10 mM HEPES) at 1×e6 cells/ml. Add 40 µl of cells/well to the PET 96-well plates containing 20 microliter diluted compound and control. Incubate @ 37° C. in a water bath for 20 minutes. Stop the assay by adding 50 µl Quench Buffer (50 mM Na Acetate, 0.25% Triton X-100).

Radioligand Binding Assays

Radioligand binding assays were run in SPA buffer (50 mM Sodium Acetate, 0.1% BSA). The beads, antibody and radioligand were diluted in SPA buffer to provide sufficient volume for each 96-well plate. To each quenched assay well was added 100 microliter cocktail containing 33.33 microliter of beads, 33.33 microliter antibody and 33.33 microliter $^{125}$I-cAMP. This was based on a final concentration of 6.3 mg/ml beads, 0.65% anti-goat antibody and 61 pM of $^{125}$I-cAMP (containing 25000–30000 CPM) in a final assay volume of 210 microliter. The plates were counted in a Wallac MicroBeta counter after a 12-hour incubation.

The data was converted to pmoles cAMP using a standard curve assayed under the same conditions. The data was analyzed using Activity Base software to generate agonist potencies (EC50) and percent relative efficacy data to NDP-alpha-MSH.

C. In Vivo Food Intake Models:

1) Overnight food intake. Sprague Dawley rats are injected intracerebroventricularly with a test compound in 400 mL of 50% propylene glyco/artificial cerebrospinal fluid one hour prior to onset of dark cycle (12 hours). Food intake is determined using a computerized system in which each rat's food is placed on a computer monitored balance. Cumulative food intake for 16 hours post compound administration is measured.

2) Food intake in diet induced obese mice. Male C57/B16J mice maintained on a high fat diet (60% fat calories) for 6.5 months from 4 weeks of age are dosed intraperitoneally with a compound of formula I. Food intake and body weight are measured over an eight-day period. Biochemical parameters relating to obesity, including leptin, insulin, triglyceride, free fatty acid, cholesterol and serum glucose levels are determined.

D. Rat Ex Copula Assay:

Sexually mature male Caesarian Derived Sprague Dawley (CD) rats (over 60 days old) are used with the suspensory ligament surgically removed to prevent retraction of the penis back into the penile sheath during the ex copula evaluations. Animals receive food and water ad lib and are kept on a normal light/dark cycle. Studies are conducted during the light cycle.

1) Conditioning to Supine Restraint for Ex Copula Reflex Tests. This conditioning takes about 4 days. Day 1, the animals are placed in a darkened restrainer and left for 15–30 minutes. Day 2, the animals are restrained in a supine position in the restrainer for 15–30 minutes. Day 3, the animals are restrained in the supine position with the penile sheath retracted for 15–30 minutes. Day 4, the animals are restrained in the supine position with the penile sheath retracted until penile responses are observed. Some animals require additional days of conditioning before they are completely acclimated to the procedures; non-responders are removed from further evaluation. After any handling or evaluation, animals are given a treat to ensure positive reinforcement.

2) Ex Copula Reflex Tests. Rats are gently restrained in a supine position with their anterior torso placed inside a cylinder of adequate size to allow for normal head and paw grooming. For a 400–500 gram rat, the diameter of the cylinder is approximately 8 cm. The lower torso and hind limbs are restrained with a non-adhesive material (vetrap). An additional piece of vetrap with a hole in it, through which the glans penis will be passed, is fastened over the animal to maintain the perpetual sheath in a retracted position. Penile responses will be observed, typically termed ex copulu genital reflex tests. Typically, a series of penile erections will occur spontaneously within a few minutes after sheath retraction. The types of normal reflexogenic erectile responses include elongation, engorgement, cup and flip. An elongation is classified as an extension of the penile body. Engorgement is a dilation of the glans penis. A cup is defined as an intense erection where the distal margin of the glans penis momentarily flares open to form a cup. A flip is a dorsiflexion of the penile body.

Baseline and/or vehicle evaluations are conducted to determine how and if an animal will respond. Some animals have a long duration until the first response while others are non-responders altogether. During this baseline evaluation, latency to first response time, number and type of responses are recorded. The testing time frame is 15 minutes after the first response.

After a minimum of 1 day between evaluations, these same animals are administered a compound of formula I at 20 mg/kg and evaluated for penile reflexes. All evaluations are videotaped and scored later. Data are collected and analyzed using paired 2 tailed t-tests to compared baseline and/or vehicle evaluations to drug treated evaluations for individual animals. Groups of a minimum of 4 animals are utilized to reduce variability.

Positive reference controls are included in each study to assure the validity of the study. Animals can be dosed by a number of routes of administration depending on the nature of the study to be performed. The routes of administration includes intravenous (IV), intraperitoneal (IP), subcutaneous (SC) and intracerebral ventricular (ICV).

E. Models of Female Sexual Dysfunction:

Rodent assays relevant to female sexual receptivity include the behavioral model of lordosis and direct observations of copulatory activity. There is also a urethrogenital reflex model in anesthetized spinally transected rats for measuring orgasm in both male and female rats. These and other established animal models of female sexual dysfunction are described in McKenna, et al., *Am. J. Physiol*, (Regulatory Integrative Comp. Physiol 30):R1276–R1285, 1991; McKenna, et al., *Pharm. Bioch. Behav.*, 40:151–156, 1991; and Takahashi, et al., *Brain Res.*, 359:194–207, 1985.

Preparation of the Compounds of the Invention

Preparation of the compounds of the present invention may be carried out via sequential or convergent synthetic routes. The skilled artisan will recognize that, in general, the three domains of a compound of formula I are connected via amide bonds. The B and C domains are optionally connected via a reduced or partially reduced amide bond (e.g., via reductive amination). The skilled artisan can, therefore, readily envision numerous routes and methods of connecting the three domains via standard peptide coupling reaction conditions.

The phrase "standard peptide coupling reaction conditions" means coupling a carboxylic acid with an amine using an acid activating agent such as EDC, dicyclohexylcarbodiimide and benzotriazol-1-yloxytris(dimethylamino)phosphonium hexafluorophosphate in a inert solvent such as DCM in the presence of a catalyst such as HOBT. The uses of protective groups for amine and carboxylic acids to facilitate the desired reaction and minimize undesired reactions are well documented. Conditions required to remove protecting groups which may be present can be found in Greene, et al., *Protective Groups in Organic Synthesis*, John Wiley & Sons, Inc., New York, N.Y. 1991.

CBZ, Boc and FMOC protecting groups are used extensively in the synthesis, and their removal conditions are well known to those skilled in the art. For example, removal of CBZ groups can he achieved by catalytic hydrogenation with hydrogen in the presence of a metal such as palladium on activated carbon in a protic solvent such as ethanol. In cases where catalytic hydrogenation is contraindicated by the presence of other potentially reactive functionality, removal of CBZ can also be achieved by treatment with a solution of hydrogen bromide in acetic acid. Removal of Boc protecting groups is carried out in a solvent such as methylene chloride, methanol or ethyl acetate with a strong acid, such as TFA or HCl or hydrogen chloride gas. FMOC protecting groups may be removed by 20% piperdine in DMF.

The compounds of formula I, when they exist as a diastereomeric mixture, may be separated into diastereomeric pairs of enantiomers by fractional crystallization from a suitable solvent such as methanol, ethyl acetate or a mixture thereof. The pair of enantiomers thus obtained may be separated into individual stereoisomers by conventional means by using an optically active acid as a resolving agent. Alternatively, any enantiomer of a compound of the formula I may be obtained by stereospecific synthesis using optically pure starting materials or reagents of known configuration.

The compounds of the present invention can be prepared according to the procedure of the following schemes and examples, which may further illustrate details for the preparation of the compounds of the present invention. The compounds illustrated in the examples are, however, not to be construed as forming the only genus that is considered as the present invention.

In the Schemes, Preparations and Examples below, various reagent symbols and abbreviations have the following meanings:

| | |
|---|---|
| BINAP | 2,2'-Bis(diphenylphosphino)-1,1'-binaphthyl |
| Boc | t-butoxycarbonyl |
| CBZ | benzyloxycarbonyl |
| DCM | dichloromethane |
| DEAD | diethyl azodicarboxylate |
| DIAD | diisopropyl azodicarboxylate |
| DIPEA | diisopropylethylamine |
| DMAP | 4-dimethylamino pyridine |
| DMF | N,N-dimethylformamide |
| DMSO | dimethylsulfoxide |
| eq. | equivalent(s) |
| EDC | 1-(3-dimethylaminopropyl)-3-ethylcarbodiimide HCl |
| ESI-MS | electron spray ion-mass spectroscopy |
| Et | ethyl |
| EtOAc | ethyl acetate |
| FMOC | 9-flurorenylmethyl carbamate |
| HATU | O-(7-azabenzotriazol-1-yl)-N,N,N',N'-tetramethyluronium hexafluorophosphate |
| HOAT: | 1-hydroxy-7-azabenzotriazole |
| HOBT | 1-hydroxybenzotriazole hydrate |
| HPLC | high performance liquid chromatography |
| HIRMS | high resolution mass spectroscopy |
| h(hr) | hour(s) |
| LRMS | low resolution mass spectroscopy |
| Me | methyl |
| Ms | methanesulfonyl |
| NMM | 4-methylmorpholine |
| $Pd_2(dba)_3$ | tris(dibenzylideneacetone)dipalladium(0) |
| Ph | phenyl |
| Phe | phenylalanine |
| Pr | propyl |
| r.t. | room temperature |
| TBAF | tetrabutylammonium fluoride |
| TBS | tertbutyldimethylsilyl |
| TFA | trifluoroacetic acid |
| TEA | triethylamine |
| THF | tetrahydrofuran |
| Tic | 1,2,3,4-tetrahydroisoquinoline-3-carboxylic acid |
| TLC | thin-layer chromatography |

Reaction Scheme 1: Coupling procedures

Procedure 1

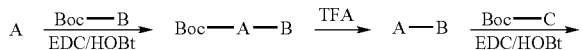

Boc—A—B—C $\xrightarrow{TFA}$ A—B—C

Procedure 2

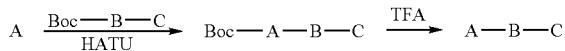

Procedure 3

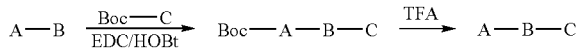

Procedure 4

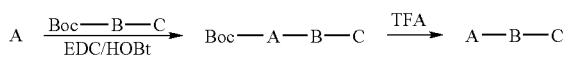

Procedure 5

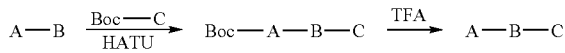

In coupling procedure 1, an appropriate A domain (e.g., piperazine) is coupled to B domain (e.g., D-Boc-p-Cl-Phe-OH) in the presence of EDC/HOBt followed by Boc deprotection. The coupled AB compound is then coupled to an appropriate C domain followed by deprotection of Boc group and salt formation. Alternatively, when C domain is not protected with Boc group, the final compound can be obtained without the deprotection step.

In coupling procedure 2, an appropriate A domain (e.g., piperazine) is coupled to an appropriate BC domain in the presence of HATU followed by deprotection of Boc group and salt formation. Alternatively, when BC domain is not protected with Boc group, the final compound can be obtained without the deprotection step.

In coupling procedure 3, an appropriate AB domain is coupled to an appropriate C domain in the presence of EDC/HOBt followed by deprotection of Boc group and salt formation.

In coupling procedure 4, an appropriate BC domain is coupled to an appropriate A domain in the presence of EDC/HOBT followed by deprotection of Boc group and salt formation. Alternatively, when C domain is not protected with Boc group, the final compound can be obtained without the deprotection step.

In coupling procedure 5, an appropriate AB domain is coupled to an appropriate C domain in the presence of HATU followed by deprotection of Boc group salt formation.

For coupling of A with Boc-B, EDC/HOAT, EDC/HOBT or DCC/HOBT can be used.

Generally, the starting material of Boc-protected piperazine (A domain) can be deprotected in the presence of TFA/$CH_2Cl_2$, HCl/EtOAc, HCl/dioxane, or HCl in MeOH/$Et_2O$ with or without a cation scavenger, such as dimethyl sulfide (DMS) before being subjected to the coupling procedure. It can be freebased before being subjected to the coupling procedure or in some cases used as the salt.

A suitable solvent such as $CH_2Cl_2$, DMF, THF or a mixture of the above solvents can be used for the coupling procedure. Suitable base includes triethyl amine (TEA), diisopropyethyl amine (DIPEA), N-methymorpholine, collidine, or 2,6-lutidine. Base may not be needed when EDC/HOBt is used.

Generally after the reaction is completed, the reaction mixture can be diluted with an appropriate organic solvent, such as EtOAc, $CH_2Cl_2$, or $Et_2O$, which is then washed with aqueous solutions, such as water, HCl, $NaHSO_4$, bicarbonate, $NaH_2PO_4$, phosphate buffer (pH 7), brine or any combination thereof. The reaction mixture can be concentrated and then be partitioned between an appropriate organic solvent and an aqueous solution. The reaction mixture can be concentrated and subjected to chromatography without aqueous workup.

Protecting group such as Boc or CBZ, FMOC, $CF_3CO$ and $H_2$/Pd—C can be deprotected in the presence of TFA/$CH_2Cl_2$, HCl/EtOAc, HCl/dioxane, HCl in MeOH/$Et_2O$, NH3/MeOH, or TBAF with or without a cation scavenger, such as thioanisole, ethane thiol and dimethyl sulfide (DMS). The deprotected amines can be used as the resulting salt or are freebased by dissolving in $CH_2Cl_2$ and washing with aqueous bicarbonate or aqueous NaOH. The deprotected amines can also be freebased by ion exchange chromatography.

The compounds of the present invention can be prepared as salt, such as TFA, hydrochloride or succinate salts by using known standard methods.

Preparation of "A Domain"

The A domains of the present invention, in general, may be prepared from commercially available starting materials via known chemical transformations. The synthesis of certain A domains of the present invention is illustrated in Reaction Scheme 2 below.

Reaction Scheme 2: "A Domain"

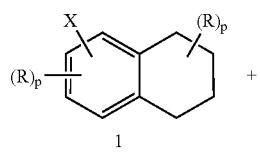

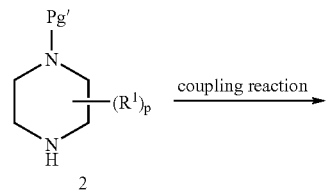

coupling reaction

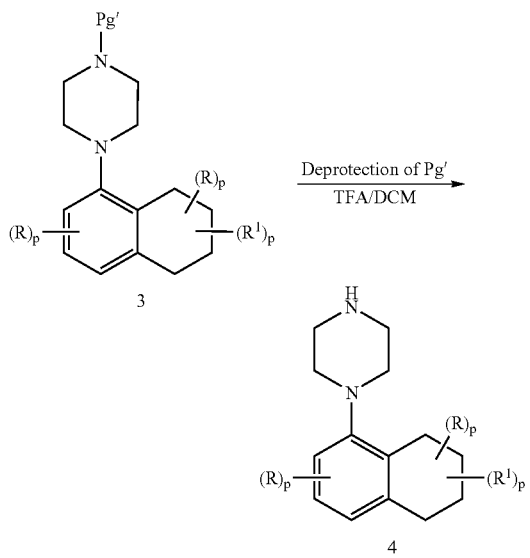

X is halo; and

Pg' is protecting group such as BOC, CBZ or FMOC.

As shown in reaction scheme above, a compound of A domain (4) can be prepared by coupling benzofused carbocyclic compound (1) with piperazine (2) followed by deprotection of compound (3). A domain containing benzofused heterocyclyl can also be prepared in accordance with the reaction scheme 2.

The protected amino acid derivatives corresponding to the B and C domains are, in many cases, commercially available. Other protected amino acid derivatives can be prepared by known literature methods (see Williams, R. M. *Synthesis of Optically Active alpha-Amino Acids*, Pergamon Press: Oxford, 1989). More detailed examples of A Domain preparation are described below.

The present invention also provides a novel process for preparing certain intermediates and/or compounds of the invention as shown in Reaction Schemes 3–5.

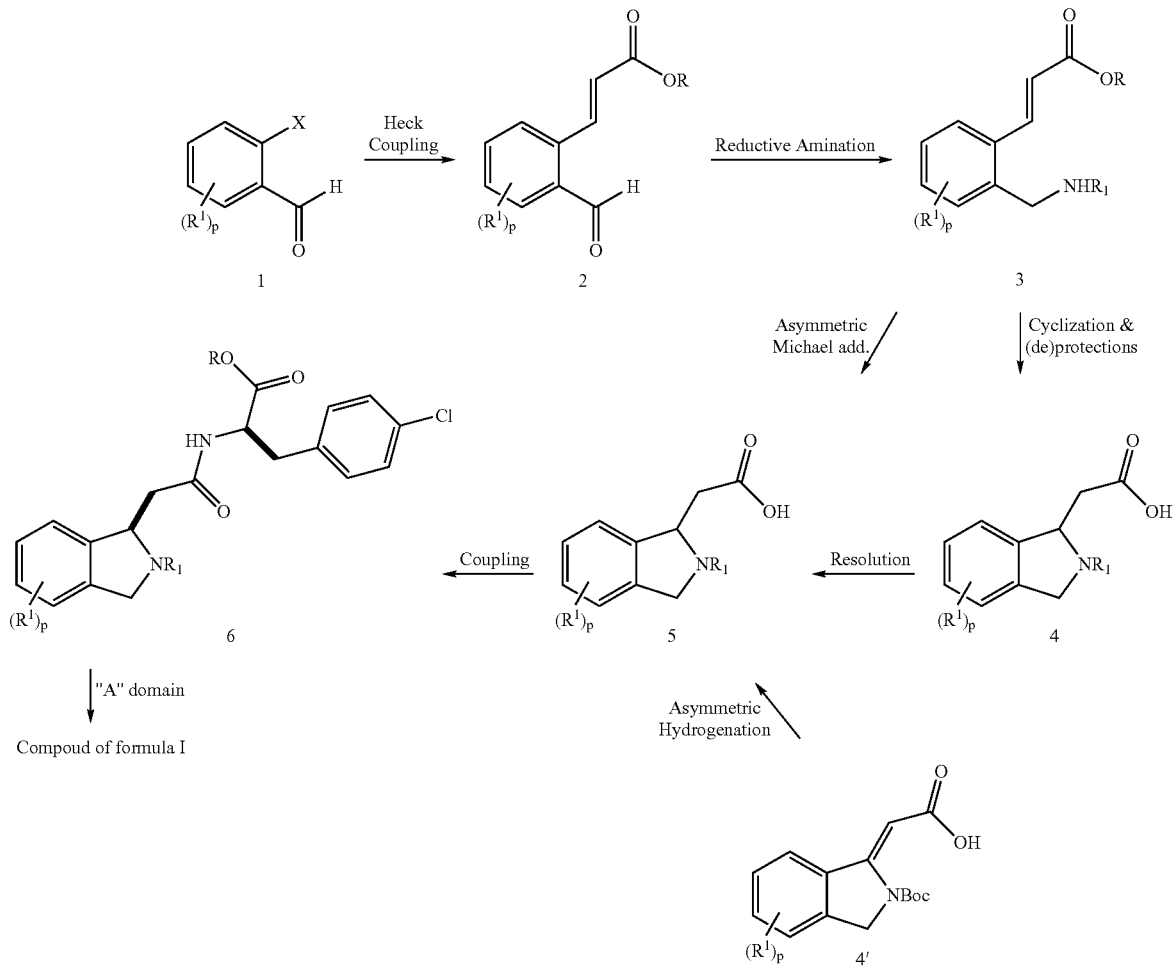

As shown in Reaction Scheme 3, a convergent synthesis of a key intermediate isoindoline (5) via a Heck coupling, followed by a reductive amination, a ring cyclization and a resolution has been developed. Also, alternate asymmetric approaches including asymmetric Michael addition and asymmetric hydrogenation have also been developed to prepare compounds of the invention and/or intermediates thereof.

As shown in Reaction Scheme 3, the isoindoline compounds of the present invention may be prepared from 2-halobenzaldehyde 1 or substituted analog thereof. Preferred starting material is 2-bromobenzaldehyde or substituted analog thereof. Pd-mediated Heck coupling of 2-bromobenzaldehydes 1 with for example, methyl acrylate, provided alpha, beta-unsaturated methyl esters 2, which undergoes reductive amination to give amines, 3 (or carbamates where $R_1$ is for example, Boc). Various Heck coupling reagents and conditions were found suitable to effect the coupling reaction. Suitable catalysts and ligands include $Pd(OAc)_2/PPh_3$, $Pd(OAc)PPh_3/BU_4NBr$, $Pd(PPH_3)_2Cl_2/CUI$, $Pd(OAC)_2/P(O-Tol)_3$. Suitable solvent or solvent systems for the Heck coupling reaction include DMF, toluene and ethyl acetate. More preferred base is triethylamine.

Reductive amination of the aldehyde functionality of 2 to amines is accomplished in good yields by reaction with benzylamine or alpha-methylbenzylamine in acidic conditions, followed by in situ reduction of the incipient imines with $NaCNBH_3$ at about pH 5. Other reducing agents including $Na(OAc)_3BH$ and $NaB_4/H$ may also be used to effect reduction of the incipient imines. Interestingly, the resulting amines immediately cyclized to the isoindoline compounds under the same acidic conditions conditions for the reduction. Direct preparation of compound 4 may also be effected by use of $BocNH_2$ instead of benzylamine in the reductive amination step. Screening of various reducing agents demonstrated that the combination of $Et_3SiH$ and TFA in $CH_3CN$ represents the preferred method for effecting reductive amination using $BocNH_2$.

The N-Boc isoindolinecarboxylic acid 5 may also be prepared from 3 as the carbamate, by an intra-molecular Michael addition and ester hydrolysis. The resolution of the isoindolinecarboxylic acids 4 by crystallization afforded enantio-pure compounds 5.

Two alternate asymmetric approaches have also been developed for the synthesis of isoindolinecarboxylic acid 5 i.e., asymmetric Michael additions and asymmetric hydrogenation. In the asymmetric Michael addition approach, alpha-methylbenzyl amine is used as a chiral auxiliary to induce the enantio-selectivity. In the asymmetric hydrogenation approach, compound 4' could be converted to 5 stereoselectively in the presence of chiral ligands.

Finally the coupling of the isoindolines 5 with the "B" domain piece, i.e., D-Cl-Phe to afford compound 6 ("BC" piece) is accomplished by standard amino acid coupling reactions such as, for example, by the use of EDC or EDCI or other activating agents in the presence of suitable is dimethyl aminopyridine (DMAP). The product (6) is then coupled with an "A" domain piece to afford the target MC4R agonist compound of formula I by coupling reactions known to one of skill in the art.

Preferably, the isoindole or other "C" domain piece is coupled to an "AB" coupled domain piece to form the compound of formula I.

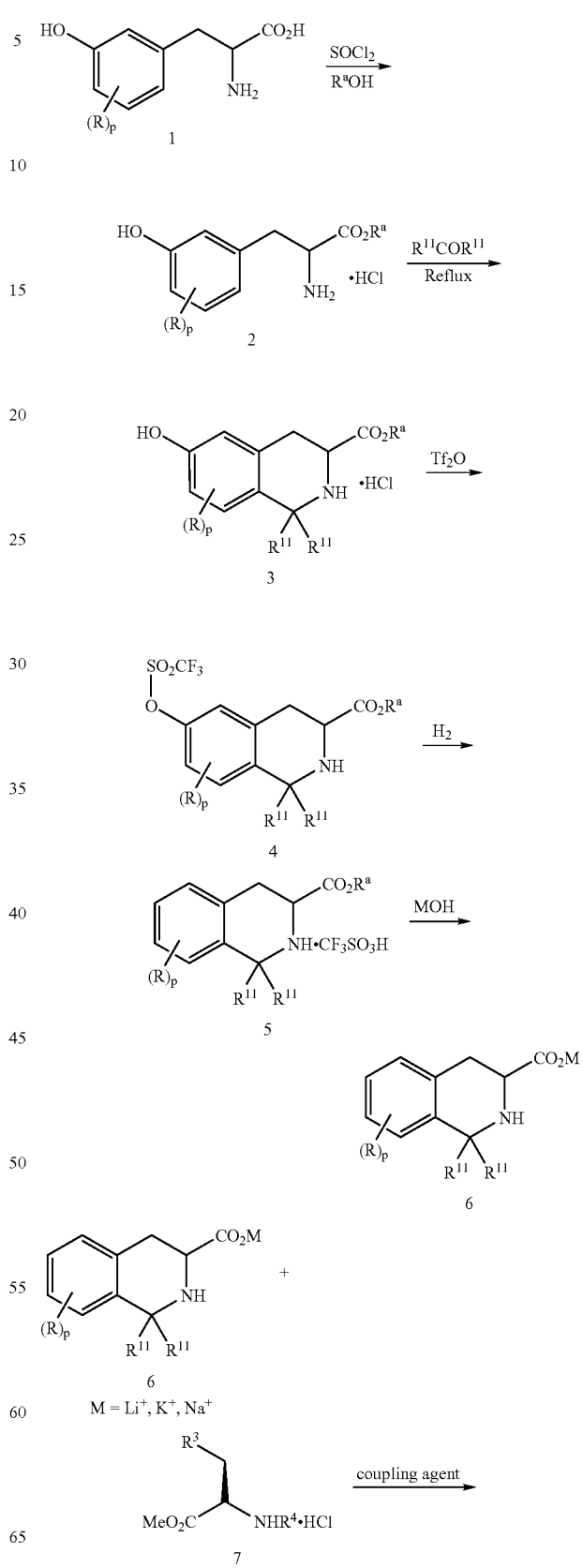

-continued

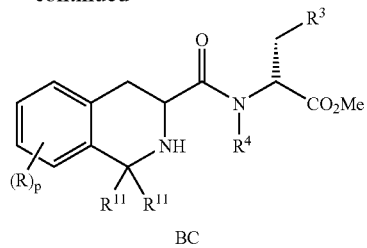

BC

As shown in Reaction Scheme 4, m-tyrosine ester or analogs, including substituted analogs thereof, may be esterified by forming the acid halide followed by nucleophilic displacement of halide by the alkoxy group from an alcohol, i.e., methanol or ethanol. Where thionyl chloride or other halide source is used the product may be isolated as the acid addition salt (2). The resulting ester (2) is subjected to a Pictet-Spengler reaction by heating with a suitable ketone or aldehyde in refluxing conditions. For example, an unsubstantiated isoquinoline backbone (3) may be formed by employing formaldehyde in the pictet-Spengler reaction. On the other hand, a gem-dimethyl substituted isoquinoline wherein $R^{11}$ is methyl, may be formed by using acetone as the ketone source and solvent. Other less reactive substituents may be substituted as the $R^{11}$ group for the practice of the present invention.

The product isoquinoline (3) may be isolated preferably as the acid addition salt. Where m-tyrosine is used as the starting material, the free hydroxyl group is removed first by protection/activation with a good leaving group such as, for example, reaction with triflic anhydride (trifluoromethane sulfonic anhydride) or methanesulfonic acid to form the triflate or mesylate in the presence of a base. The triflate is a preferred group used to set up the compound (3) for deoxygenation because of the extra electron withdrawing effect of the trifluoromethane substituent. The deoxygenation reaction is effected by hydrogenation at pressures of about 50 psi. The product (4) may be isolated as the acid addition salt. The product (4) is hydrolyzed under basic conditions to afford the acid salt. Suitable bases for the above hydrolysis include aqueous sodium hydroxide, potassium hydroxide and sodium lithium hydroxide. The reaction is preferably performed in a mixture of aqueous and organic solvents. An exotherm during addition of base may be regulated (i.e., less than about 35° C.) to avoid overheating or "runaway reactions." The reaction product may be isolated by aqueous work up. Alternatively, the entire mixture may be concentrated and washed with organic solvents to afford the desired product (6) after crystallization.

The product (6) is then reacted with a "B" domain substrate such as, for example, 4-chloro-D-phenylalanine as described previously and in the experimental section. The resulting "BC" combination product is then reacted with an "A" domain piece to form the respective compound of formula I. Alternatively, the product (6) may be reacted with an "AB" domain combination product to afford a compound of formula I.

One of skill is aware that certain protections and deprotections of intermediates in Reaction Scheme 4, to form the carbamate, substituted amine or free amine at the isoquinolinyl nitrogen are possible and contemplated as within the scope of this invention. Unless otherwise specified, reagents and procedures for effecting the reactions described herein are known to one of skill in the art and may be found in general reference texts such as *Advanced Organic Chemistry* by J. March, 5$^{th}$ edition, Wiley Interscience Publishers, New York, N.Y., and references therein.

In an alternate procedure, the isoquinoline product i.e:, compound (3) or (5) including their N-protected analogs may be resolved by reaction with a resolving agent such as for example, L-tartaric acid, dehydroabietylamine or other resolving agents known to one of skill in the art.

Alternatively, asymmetric analogs of product (6) may be prepared by using asymmetric starting materials. For example, L-DOPA may be used in place of m-tyrosine ester in reactions essentially similar to those described and illustrated in Reaction Scheme 4, and in the examples, to afford the asymmetric analog of compound (6).

Tetrahydroisoquinoline acetic acid derivatives may be prepared and utilized as shown in Reaction Scheme 5 below:

Reaction Scheme 5

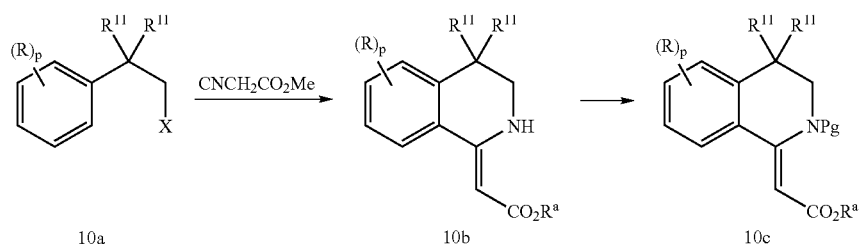

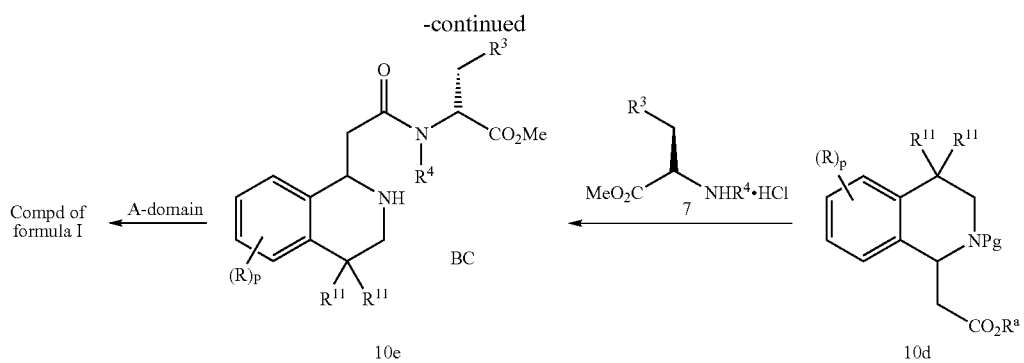

As shown in Reaction Scheme 5, a compound of formula 10a wherein X is halogen, preferably bromo or chloro, and R and $R^{11}$ are as defined previously, and which is obtained commercially or prepared from commercial starting materials is reacted with cyanomethylethylacetate to afford a compound of formula 10b. The compound of formula 10b may be protected as the compound 10c with a suitable protecting group (Pg) and then subjected to hydrogenation conditions including for example asymmetric hydrogenation to form a compound of formula 10d, which may be chiral (depending on hydrogenation conditions, i.e., asymmetric versus non-assymetric hydrogenation). The compound of formula 10d or stereoisomer thereof, is reacted with a B-domain piece such as, for example, 4-chloro-D-phe to afford a BC piece (10e). The compound of formula 10e is then reacted with an A-domain piece to afford a compound of formula I. The details of the specific reaction steps are similar to or analogous to reactions taught herein, and in the experimental section. Furthermore, one of skill in the art is aware of that such intermediate reactions as hydrolysis and deprotection may be necessary to achieve optimum yields in certain steps of the scheme as shown. One of skill in the art is also aware of further common manipulations such as N-alkylation, or N-acylation, and alkylations on the benzene ring to afford other compounds of formula I.

The following describes the detailed examples of A Domain preparation.

Preparation 1A

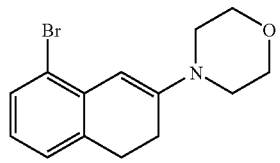

To 8-Bromo-2-tetralone (3.0 g, 13.3 mmol) is added p-toluenesulfonic acid (0.25 g, 1.47 mmol), morpholine (7.43 g, 85.3 mmol), and toluene (25 mL). The mixture is heated at reflux, using a Dean-Stark trap, for about 12 hours. After cooling to r.t. the mixture is concentrated to dryness and the crude enamine (3.9 g) is taken on to the next step with no additional purification.

Preparation 2A

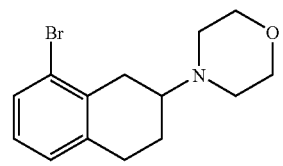

To the compound of Preparation 1A (3.9 g, 13.33 mmol), in methanol (50 mL), is added acetic acid (7.6 mL, 133.3 mmol) followed by careful addition of sodium borohydride (1.0 g, 26.6 mmol). The solution is allowed to stir at r.t. for about two hours. After concentrating to dryness, the remaining residue is taken up in EtOAc (100 mL). The organics are washed with saturated $NaHCO_3$ (100 mL), and the desired product is extracted into 1N HCl (100 mL). The aqueous layer is then made alkaline with 5N NaOH (30 mL) and extracted into EtOAc (100 mL). The organic phase is concentrated to dryness to afford about 1.8 g of the compound 2A (46%). EIS-MS 298.0 [M+1]

Preparation 3A

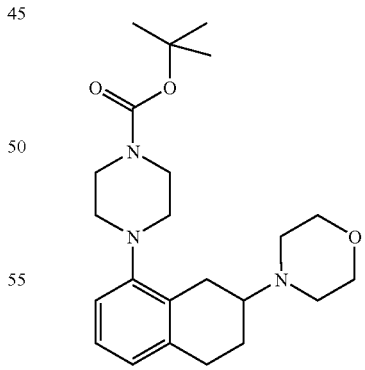

To compound 2A (0.50 g, 1.69 mmol), in toluene (10 mL), is added piperazine-1-carboxylic acid tert-butyl ester (0.314 g, 1.69 mmol), BINAP (0.168 g, 0.27 mmol), Na-t-BuO (0.243 g, 2.53 mmol) and $Pd_2(dba)_3$ (0.124 g, 0.135 mmol). The solution is heated at reflux for about 4 hours, diluted with EtOAc (100 mL), and filtered over a pad of celite. The filtrate is concentrated to dryness. The crude material is purified by flash chromatography ($SiO_2$, eluting with EtOAc to EtOAc-MeOH-TEA, 80:10:10) to afford about 0.65 g of the compound 3A (96%). EIS-MS 402.1 [M+1]

Preparation 4A

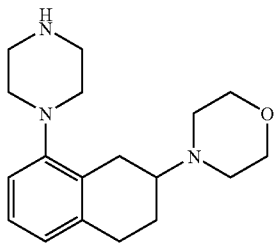

To compound 3A (0.65 g, 1.62 mmol), in DCM (5 mL), is added TFA (5 mL) and the mixture is stirred at r.t. for about 45 minutes. After concentrating to dryness, the resulting residue is taken up with 1N NaOH and the desired "free" amine is extracted into EtOAc (100 mL). The organic extracts are concentrated to dryness to afford about 290 mg of the compound 4A (60%). EIS-MS 302.0 [M+1]

Preparation 5A

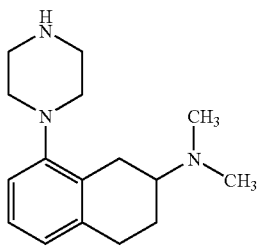

The 2-dimethylamino-8-bromo-1,2,3,4-tetrahydronaphthalene (1.0 g, 3.93 mmol) is prepared by following a substantially similar procedure as described in Preparation 1A and 2A, and from commercially available 1-Boc-piperazine (0.805 g, 4.32 mmol) as described *J. Am. Chem. Soc.*, 118:7215–7216, 1996. The desired product is purified by flash chromatography. Yield: 1.35 g (95%). EIS MS: 360.2 [M+H].

To the Boc-protected compound (1.35 g, 3.75 mmol) is added TFA (5 mL) and DCM (5 mL) and the resulting mixture is stirred at r.t. for about 30 minutes. After concentrating to dryness, the resulting residue is taken up in 1N NaOH and the desired amine extracted into EtOAc (100 mL). The organics are washed with H$_2$O and brine, and then re-concentrated. Yield: 970 mg. EIS-MS: 260.1 [M+H]

The A domain compounds 6A to 11A are prepared from 8-bromo-2-tetralone and an appropriate amine by following the procedure substantially similar to that described in Preparation 4A.

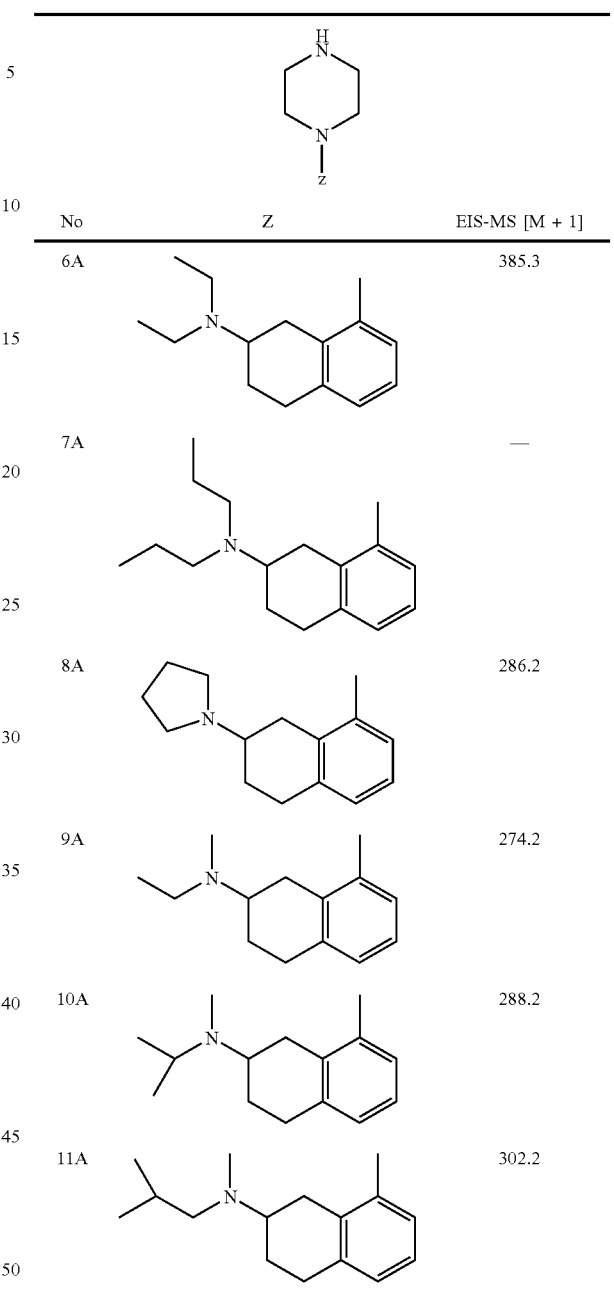

| No | Z | EIS-MS [M + 1] |
|---|---|---|
| 6A | | 385.3 |
| 7A | | — |
| 8A | | 286.2 |
| 9A | | 274.2 |
| 10A | | 288.2 |
| 11A | | 302.2 |

Preparation 12A

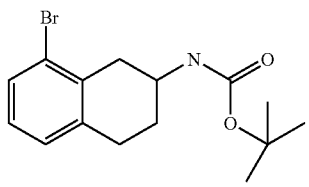

To commercially available 8-bromo-2-aminotetralin (0.85 g, 3.76 mmol) is added Boc$_2$O (0.90 g, 4.13 mmol), K$_2$CO$_3$ (1.03 g, 7.52 mmol) and THF/H₂O (1:1, 25 mL). The mixture is stirred for about 30 minutes and then diluted 10 fold with EtOAc. The organics are washed with saturated NaHCO₃, H₂O, and brine, and then concentrated to dryness. Material is recrystallized from hexanes to afford about 1.2 g of compound 12A (98%). EIS-MS 327.1 [M+1]

Preparation 13A

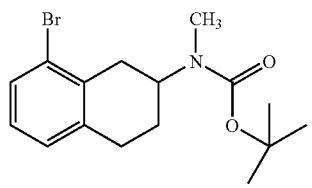

To compound 12A (0.18 g, 0.54 mmol) in THF (3 mL) is added NaH (60% dispersion in oil, 0.03 g, 0.8 mmol). The solution is allowed to stir at r.t. for about one hour. Iodomethane (0.15 g, 1.07 mmol) is then added drop-wise to the solution. The mixture is allowed to stir at r.t. for about 18 hours. This mixture is then diluted 10 fold with EtOAc (30 mL) and washed with water (30 mL). The organic phase is concentrated to dryness to afford about 0.13 g of compound 13A (69%). EIS-MS 340.1 [M+1]

Preparation 14A

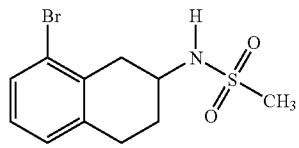

To commercially available 8-bromo-2-aminotetralin (0.26 g, 1.14 mmol) in CH₂Cl₂ (5 mL), is added pyridine (0.28 mL, 3.44 mmol), and methanesulfonyl chloride (0.0.89 mL, 1.14 mmol). The mixture is stirred at r.t. for about 30 minutes and then diluted with EtOAc (50 mL). The organics are washed with H₂O and brine and then concentrated to dryness to afford about 180 mg of compound 14A (52%). EIS-MS 304.9 [M−1]

Preparation 15A

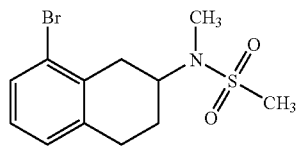

To compound 14A (0.275 g, 0.903 mmol), in THF (5 mL) is added NaH (60% dispersion in oil, 0.038 g, 1.54 mmol).

The solution is allowed to stir at r.t. for about one hour. Iodomethane (0.061 mL, 0.99 mmol) is added drop-wise to the solution. The reaction mixture is allowed to stir at r.t. for about 12 hours. This mixture is then diluted 10 fold with EtOAc (30 mL) and washed with water (30 mL). The organic phase is concentrated to dryness. The desired product is purified by flash chromatography (SiO₂, eluting with 30% EtOAc in Hexanes) to afford about 0.227 g of compound 15A (79%). EIS-MS 320.1 [M+1]

Preparation 16A

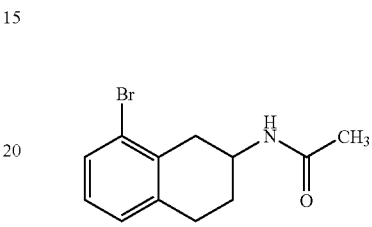

To commercially available 8-bromo-2-aminotetralin (1.5 g, 6.63 mmol) is added Ac₂O (10 mL) and pyridine (10 mL). The mixture is heated at 80° C. for about 4 hours. After cooling to r.t., the mixture is concentrated to dryness and the resulting residue taken up in EtOAc (50 mL). The organics are washed with saturated NaHCO₃, H₂O and brine, and then concentrated to dryness. The product is recrystallized from EtOAc-Hexanes to afford about 1.75 g of compound 16A (98%). EIS-MS 270.1 [M+1]

Preparation 17A

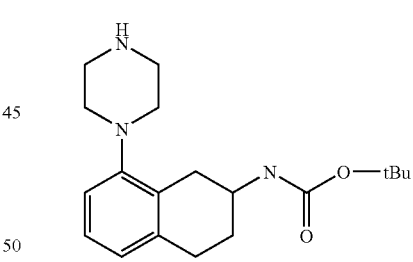

To commercially available 8-bromo-2-aminotetralin (850 mg, 3.76 mmol) is added Boc₂O (900 mg, 4.13 mmol), K₂CO₃ (1.03 g, 7.52 mmol) and THF/H₂O (1:1, 25 mL). The mixture is rapidly stirred for about 30 minutes and then diluted 10 fold with EtOAc. The organics are washed with saturated NaHCO₃, H₂O and brine, and then concentrated to dryness. The material is recrystallized from hexanes. Yield: 1.2 g (98%).

To the compound obtained above (300 mg, 0.920 mmol), piperazine is added (316 mg, 3.68 mmol) by following conditions outlined in *J. Am. Chem. Soc.*, 118:7215–7216 for the coupling. The final compound is purified by flash chromatography (SiO₂ by eluting with 90:5:5, EtOAc-Et₃N-MeOH) to afford about 248 g of compound 17A (81%). EIS-MS: 332.2 [M+1]

Preparation 18A

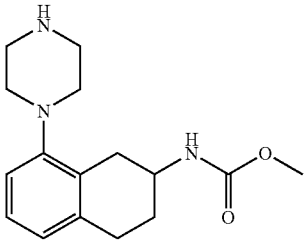

To 2-amino-8-(4-t-butyloxycarbonylpiperazin-1-yl)decalin (75 mg, 0.226 mmol), in DCM (5 mL) is added Et₃N (63 microliters) and methyl chloroformate (17 microliters). The mixture is stirred at r.t. for about 30 minutes and then concentrated to dryness. The resulting residue is taken up in EtOAc (50 mL) and the organics are washed with saturated NaHCO₃, H₂O and brine, and then concentrated to dryness. Desired product is purified by flash chromatography (SiO₂ by eluting EtOAc. Yield: 40 mg (45%). EIS-MS: 390.2 [M+H]

Following the procedure as described in Preparation 5A, the Boc-protected compound from above (40 mg, 0.103 mmol) is deprotected to afford about 26 mg (87%) of compound 18A. EIS-MS: 290.1 [M+H]

Preparation 19A

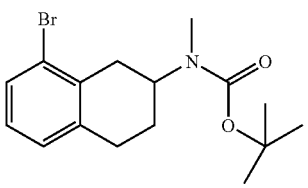

Step 1: To commercially available 8-bromo-2-aminotetralin (0.85 g, 3.76 mmol) is added Boc₂O (0.90 g, 4.13 mmol), K₂CO₃ (1.03 g, 7.52 mmol) and THF/H₂O (1:1, 25 mL). The mixture is stirred for about 30 minutes and then diluted 10 fold with EtOAc. The organics are washed with saturated NaHCO₃, H₂O and brine, and then concentrated to dryness. Material is recrystallized from hexanes yielding an off white solid (1.2 g, 98%). EIS-MS 327.1 [M+1]

Step 2: To the compound from Step 1 (0.18 g, 0.54 mmol) in THF (3 mL) is added NaH (60% dispersion in oil, 0.03 g, 0.80 mmol). The solution is allowed to stir at r.t. for about an hour. Iodomethane (0.15 g, 1.07 mmol) is then added dropwise to the solution. The reaction mixture is allowed to stir at r.t. for about 18 hours. This mixture is then diluted 10 fold with EtOAc (30 mL) and washed with water (30 mL). The organic phase is then concentrated to dryness to afford about 0.13 g of the final compound (69%). EIS-MS 340.1 [M+1]

Preparation 20A

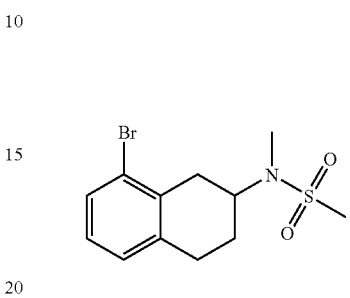

Step 1: To commercially available 8-bromo-2-aminotetralin (0.26 g, 1.14 mmol) in DCM (5 mL) is added pyridine (0.28 mL, 3.44 mmol), and methanesulfonyl chloride (0.0.89 mL, 1.14 mmol). The mixture is stirred at r.t. for about 30 minutes and then diluted with EtOAc (50 mL). The organics are washed with H₂O and brine and then concentrated to dryness. Yield: 180 mg, 52%. EIS-MS 304.9 [M–1]

Step 2: To compound from step 1 (0.275 g, 0.903 mmol), in THF (5 mL) is added NaH (60% dispersion in oil, 0.038 g, 1.54 mmol). The solution is stirred at r.t. for about an hour. Iodomethane (0.061 mL, 0.99 mmol) was then added dropwise to the solution. The mixture is stirred at r.t. for 12 hours. This mixture is then diluted 10 fold with EtOAc (30 mL) and washed with water (30 mL). The organic phase is concentrated to dryness. The desired product is purified by flash chromatography (SiO₂, eluting with 30% EtOAc in Hexanes) to afford about 0.227 g of the final compound (79%). EIS-MS 320.1 [M+1]

Preparation 21A

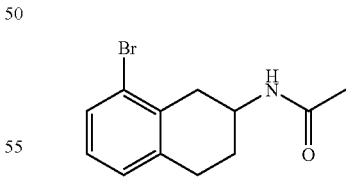

To commercially available 8-bromo-2-aminotetralin (1.5 g, 6.63 mmol) is added Ac₂O (10 mL) and pyridine (10 mL). The mixture is heated at 80° C. for about 4 hours. After cooling to r.t., the mixture is concentrated to dryness and the resulting residue was taken up in EtOAc (50 mL). The organics is washed with saturated NaHCO₃, H₂O and brine and then concentrated to dryness. The product is recrystallized from EtOAc-hexanes to afford about 1.75 g of the final compound (98%). EIS-MS 270.1 [M+1]

Preparation of 19Aa–21Aa

The A domain compounds of 19Aa–21Aa are prepared from the appropriately substituted 8-bromo-2-tetraline and N-Boc-piperazine by following substantially similar procedures as described in Preparations 3 to 4.

| No | Z | EIS-MS [M + 1] |
|---|---|---|
| 19Aa | | 346.2 |
| 20Aa | | 324.1 |
| 21Aa | | 274.1 |

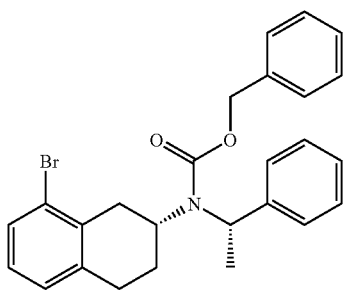

Preparation 22A

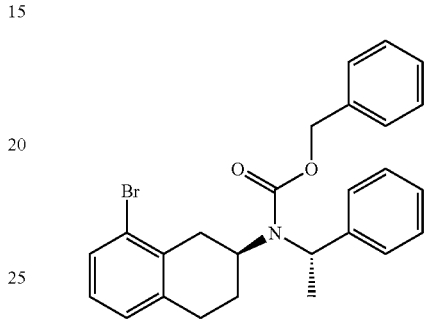

To (15.31 g, 46.35 mmol) of 8-bromo-1,2,3,4-tetrahydro-napthalen-2-yl)-(1-phenyl-ethyl)-amine, whose preparation was described in *J. Med. Chem.* 1993, 36(15), 2066–2074, is added THF (50 mL), $H_2O$ (50 mL), $K_2CO_3$ (12.81 g, 92.71 mmol) and the mixture is cooled to 0° C. Benzyl chloroformate (6.61 mL, 46.35 mmol) is then added and the mixture is allowed to warm to r.t. and stirred for an additional 30 minutes. After diluting with EtOAc (5 fold), the organics are washed with $H_2O$, saturated $NaHCO_3$, brine, and concentrated to dryness. The resulting residue is purified by flash chromatography ($SiO_2$, eluting with 10% EtOAc in Hexanes) to afford about 17.5 g of the final compound (81%). EIS-MS 464.2 [M+1]

Preparation 23A

To (1.54, 4.66 mmol) of 8-bromo-1,2,3,4-tetrahydro-napthalen-2-yl)-(1-phenyl-ethyl)-amine, whose preparation is described in *J. Med. Chem.* 1993, 36(15), 2066–2074, is added THF (10 mL), $H_2O$ (10 mL), $K_2CO_3$ (1.28, 92.71 mmol) and the mixture is cooled to 0° C. Benzyl chloroformate (0.79 mL, 5.59 mmol) is then added and the mixture is allowed to warm to r.t. and stirred for an additional 30 minutes. After diluting with EtOAc (5 fold), the organics are washed with $H_2O$, saturated $NaHCO_3$, brine, and concentrated to dryness. The resulting residue is purified by flash chromatography ($SiO_2$, eluting with 10% EtOAc in Hexanes) to afford about 2.0 g of the final compound (92%). EIS-MS 464.2 [M+1]

Preparation 24A

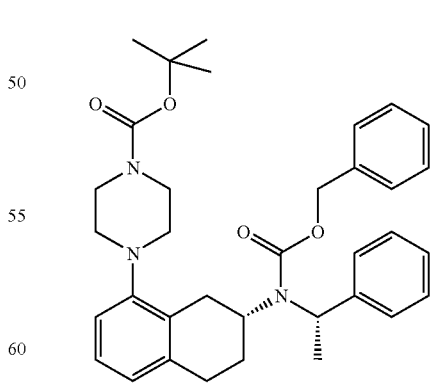

The compound 24A is prepared from the compound 22A (17.5 g, 37.7 mmol) by essentially following the procedure as described in Preparation 3A to afford about 15.86 g (74%). EIS-MS 570.2 [M+1]

Preparation 25A

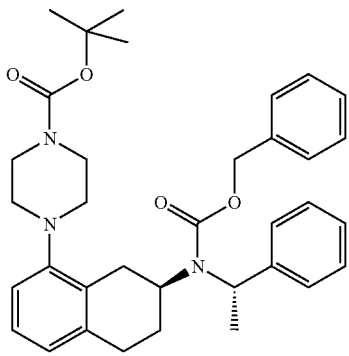

The compound 25A is prepared by essentially following the procedure as described in Preparation 23A to afford about 1.28 g (52%). EIS-MS 570.2 [M+1]

Preparation 26A

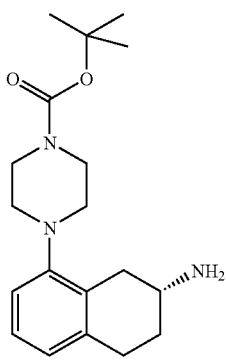

To Pd(OH)$_2$/C (7.5 g), 10% Pd/C (15 g), in EtOH/HOAc (4:1, 125 mL), is added the compound 24A (15.85 g, 27.8 mmol) in EtOH/HOAc (4:1, 125 mL), and the mixture is stirred at r.t. under 1 atm H$_2$ overnight. The catalyst is removed by filtering over a bed of celite and the filtrate is concentrated to dryness. The resulting residue is purified by flash chromatography (SiO$_2$, eluting with 90:5:5, EtOAc-TEA-MeOH) to afford about 6.5 g of the final compound (71%). EIS-MS 332.3 [M+1]

Preparation 27A

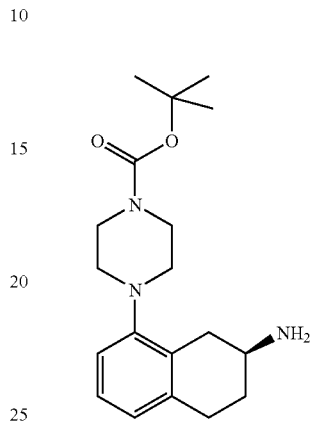

To Pd(OH)$_2$/C (0.6 g), 10% Pd/C (1.28 g), in EtOH/HOAc (4:1, 40 mL), is added the compound 25A (1.28 g, 2.25 mmol) in EtOH/HOAc (4:1, 30 mL), and the mixture is stirred at r.t. under 1 atm H$_2$ overnight. The catalyst is removed by filtering over a bed of celite and the filtrate is concentrated to dryness. The resulting residue is purified by flash chromatography (SiO$_2$, eluting with 90:5:5, EtOAc-TEA-MeOH) to afford about 340 mg of the final compound (46%). EIS-MS 332.3 [M+1]

Preparation 28A

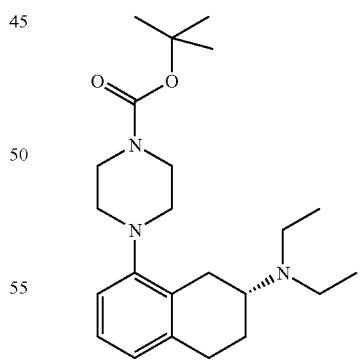

To the compound 26A (2.0 g, 6.03 mmol) is added K$_2$CO$_3$ (4.16 g, 30.16 mmol), ethyl bromide (1.35 mL, 18.09 mmol) and DMF (1 mL). The mixture is stirred at r.t. for about 24 hours and then diluted 10 fold with EtOAc. The organics are washed with H$_2$O, brine and concentrated to dryness. The resulting residue is purified by flash chromatography (SiO$_2$, eluting with 98:1:1, EtOAc-TEA-MeOH) to afford about 1.86 g of the final compound (80%). EIS-MS 388.4 [M+1]

Preparation 29A

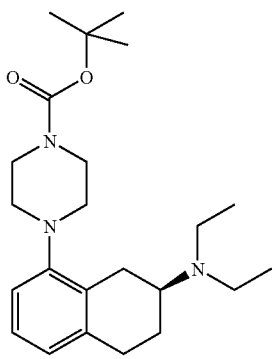

Compound 29A is prepared from the compound 27A by following the procedure as described in Preparation 28A. EIS-MS 388.4 [M+1]

Preparation 30A

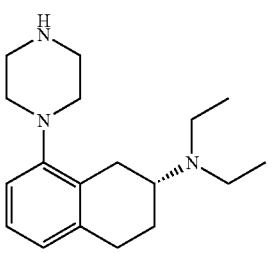

To the compound 28A (0.35 g, 0.903 mmol) in DCM (5 mL) is added TFA (5 mL), and the mixture is stirred at r.t. for about 45 minutes. After concentrating to dryness, the resulting residue is taken up with 1N NaOH and the desired "free" amine is extracted into EtOAc (100 mL). The organic extracts are concentrated to dryness to afford about 230 mg of the final compound (89%). EIS-MS 288.2 [M+1]

Preparation 31A

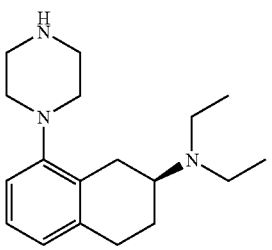

Compound 31A is prepared from the compound 29A by following a substantially similar procedure as described in Preparation 30A. EIS-MS 288.2 [M+1]

Preparation 32A

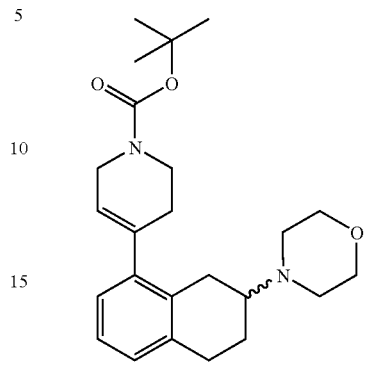

To the compound 2A (0.725 g, 2.45 mmol), in DMF (20 mL), is added 1-2(H)-pyridine-carboxylic acid, 3,6-dihydro-4-(4,4,5,5-tetramethyl-1,3,2-dixoaborolan-2-yl)-1,1-dimethyl ethyl ester (0.909 g, 2.94 mmol, *Tet. Lett.*, 41:3705–3708, 2000), dichloro(1,1'-bis(diphenylphosphino)ferrocene)palladium (II) DCM adduct (0.108 g, 0.147 mmol), and $K_2CO_3$ (1.02 g, 7.35 mmol). The reaction is heated to about 90° C. overnight. The mixture is cooled, diluted with DCM and filtered through celite. The filtrate is concentrated to dryness and the resulting residue is taken up in EtOAc (50 mL). The organics are washed with $H_2O$, brine, and concentrated to dryness. The desired product is purified by flash chromatography ($SiO_2$, eluting with 100% EtOAc to EtOAc-TEA-MeOH, 80:10:10) to afford about 624 mg of the final compound (64%). EIS-MS 399.2 [M+1]

Preparation 33A

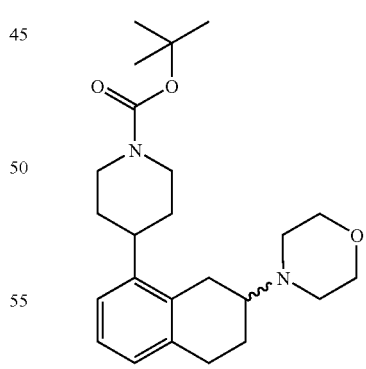

To the compound 32A (0.62 g, 1.57 mmol) in EtOH (20 mL) is added a slurry of 10% Pd/C (0.62 g) in EtOH (20 mL). The mixture is stirred rapidly under $H_2$ (1 atm) for about 2 hours. The reaction mixture is filtered over a pad of celite and washed with EtOAc (100 mL). The filtrate concentrated to dryness to afford about 0.58 g of the final compound (83%). EIS-MS 401.3 [M+1]

Preparation 34A

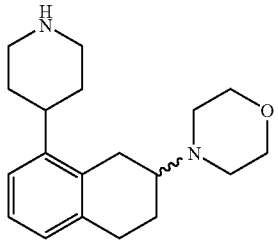

To the compound 33A (0.50 g, 1.25 mmol) in DCM (3 mL) is added TFA (3 mL), and the mixture is stirred at r.t. for about 45 minutes. After concentrating to dryness, the resulting residue is taken up with 1N NaOH and the desired "free" amine extracted into EtOAc (50 mL). The organic extracts are concentrated to dryness to afford about 300 mg of the final compound (81%). EIS-MS 301.2 [M+1]

The A domain 35A–42A are prepared from using appropriate 8-bromo-2-tetralin (described in Preparation 1A and 2A) by following a substantially similar procedures as described in Preparations 32A–34A.

| No | Z | (EIS)-MS [M + 1] |
|---|---|---|
| 35A | 8-methyl-tetralin-2-yl N(Et)(Et) | 287.2 |
| 36A | 8-methyl-tetralin-2-yl N(n-Pr)(n-Pr) | 315.3 |
| 37A | 8-methyl-tetralin-2-yl N(Me)(Me) | — |
| 38A | 8-methyl-tetralin-2-yl N(Me)(SO₂CH₃) | 323.1 |
| 39A | 8-methyl-tetralin-2-yl NH(SO₂CH₃) | 309.1 |
| 40A | 8-methyl-tetralin-2-yl N(Me)(iPr) | 287.2 |
| 41A | 8-methyl-tetralin-2-yl NH-C(O)CH₃ | 273.1 |
| 42A | 8-methyl-tetralin-2-yl pyrrolidinyl | 285.2 |

Preparation 43A

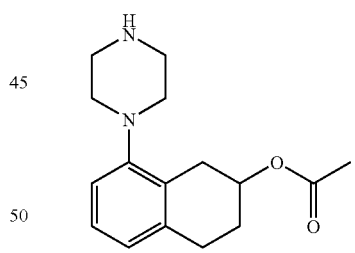

Step 1: 8-Bromo-2-hydroxytetralin is prepared from 8-bromo-2-tetralone (3.0 g, 13.3 mmol) as described in *J. Org. Chem.*, 56(19):5564–5566, 1991. The desired product is purified by flash chromatography (Silica gel 60, eluting with 25% EtOAc in Hexanes) to afford about 2.7 g (90%). EIS-MS: 228 [M+H].

Step 2: To 8-bromo-2-hydroxytetralin (2.0 g, 8.81 mmol) is added TBSCl (1.39 g, 9.25 mmol), imidazole (1.19 g, 17.6 mmol) and DMF (20 mL). The mixture is stirred at r.t. for about 5 hours and then diluted 10 fold with EtOAc. The organics are washed with H₂O and brine, and then concentrated to dryness to afford about 2.5 g (83%).

Step 3: 1-Boc-piperazine is coupled to the TBS-protected alcohol from above (2.49 g, 7.29 mmol) as described in *J.*

*Org. Chem.*, 61:7240–7241, 1996. The desired product is purified by MPLC to afford about 1.6 g (50%). EIS-MS: 447.3 [M+H].

Step 4: To the coupled product (810 mg, 1.81 mmol), in THF (10 mL), is added tetrabutylammonium fluoride (1.0M in THF, 3.6 mL, 3.6 mmol) and the reaction mixture stirred at r.t. for about 18 hours. The mixture is diluted 10 fold with EtOAc, and the organics are washed with saturated NaHCO$_3$, H$_2$O and brine, and then concentrated to dryness to give about 540 mg of 1-t-butyloxycarbonyl-4-(2-hydroxytetralin-8-yl)piperazine (90%). EIS-MS: 332.2 [M+H].

Step 5: To compound of Step 4 (96 mg, 0.288 mmol) is added Ac$_2$O (5 mL) and pyridine (5 mL). The mixture is stirred at 80° C. for about 1.5 hours and then allowed to cool to r.t. After concentrating to dryness, the resulting residue is taken up in EtOAc (100 mL) and the organics are washed with H$_2$O and brine, and then concentrated to dryness to give about 75 mg of Boc-protected compound (70%). EIS-MS: 375.2 [M+H].

Step 6: To the compound of step 5 (75 mg, 0.200 mmol) is added TFA (4 mL) and DCM (4 mL). The resulting mixture is stirred at r.t. for about 1 hour and then concentrated to dryness. The resulting residue is taken up in H$_2$O at pH 10 (1N NaOH) and the desired amine is extracted into EtOAc (50 mL). The organics are washed with H$_2$O and brine and then concentrated to dryness. EIS-MS: 275.2 [M+H].

Preparation 44A

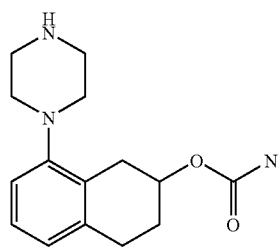

The Boc-protected compound is prepared from 1-t-butyloxycarbonyl-4-(2-hydroxytetralin-8-yl)piperazine (107 mg, 0.321 mmol) as described in *J. Chem. Perk. Trans. 1*, 4:377–382, 1996 (85 mg, 71%). EIS-MS: 376.2 [M+H].

The final compound is prepared from the Boc-protected analogue (80 mg, 0.213 mmol) by following the procedure as described in Preparation 5A to afford about 58 mg (100%) of the final compound. Ion spray MS: 276.1 [M+H].

Preparation 45A

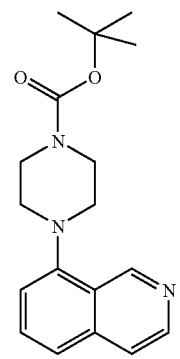

The 8-bromoisoquinoline (3.18 g, 15.28 mmol), piperazine (3.29 g, 38.21 mmol), Pd$_2$(dba)$_3$ (696 mg, 0.76 mmol), BINAP (1.43 g, 2.29 mmol) and sodium tert-butoxide (2.06 g, 21.39 mmol) are dissolved in toluene (80 mL), and the mixture is heated to 90° C. for about 16 hours. The mixture is allowed to cool to r.t. and filtered across celite and concentrated. The residue is purified by silica gel chromatography, which is then dissolved in DCM (100 mL). Excess BOC anhydride is added to the mixture while stirring. The mixture is allowed to react for about 2 hours and then concentrated. The product is purified by chromatography on silica gel to afford about 3.97 g of the final compound (83%). EIS-MS 214.2 [M-BOC].

Preparation 46A

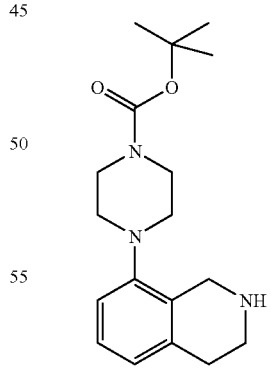

The compound 45A (1.2 g, 3.83 mmol) is dissolved in a slurry of PtO$_2$ (1 g) in isopropanol (150 mL), and pressurized to 45 psi with hydrogen gas overnight. The slurry is filtered and concentrated to dryness. The resultant oil is purified by flash chromatography on silica gel to afford about 920 mg of the final compound (76%). EIS-MS 318.1 [M+1]

Preparation 47A

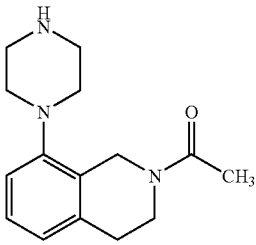

The compound 46A (150 mg, 0.47 mmol) is dissolved in acetic anhydride (4 mL) and TEA (1 mL) is added. The mixture is stirred for about 4 hours. The mixture is then diluted with water and DCM (50 mL/50 mL) and the pH is adjusted to about 10 with 1M NaOH. The organic fraction is concentrated to dryness, and the resulting residue purified by flash chromatography on silica gel. The product is stirred in 1:1 TFA/DCM (10 mL) for about 2 hours. The mixture is concentrated to dryness and the resulting residue is subjected to SCX ion exchange chromatography followed by flash chromatography on silica gel to give about 113 mg of the final product (93%). EIS-MS 260.1 [M+1]

Preparation 48A

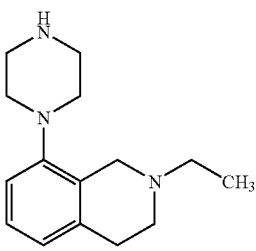

The compound 47A (337 mg, 1.38 mmol) is dissolved in THF (10 mL) and lithium aluminum hydride (210 mg, 5.5 mmol) is added as a slurry in THF (5 mL). The mixture is stirred for about 4 hours at reflux. The reaction is worked up with water and the organics are washed with 1N NaOH and then concentrated to dryness. The resulting residue is purified by flash chromatography on silica gel to give about 226 mg of the final product (67%). EIS-MS 246.2 [M+1]

Preparation 49A

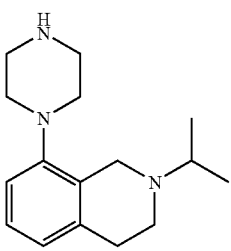

To the compound 46A (250 mg, 0.79 mmol) in DCM (3.6 mL) is added acetone (0.11 mL, 1.5 mmol), sodium triacetoxyborohydride (469 mg, 2.21 mmol) and acetic acid (0.272 mL, 4.74 mmol), and the mixture is stirred at r.t. for about 24 hours. The mixture is diluted with DCM (50 mL) and washed with 1M NaOH. The organic fraction is concentrated and purified by silica gel chromatography, and the product stirred in 1:1 TFA/DCM (10 mL) for about 2 hours. The reaction is concentrated and the resulting residue is subjected to SCX ion exchange chromatography followed by silica gel chromatography to give about 182 mg of the final compound (89%). EIS-MS 260.1 [M+1]

Preparation 50A

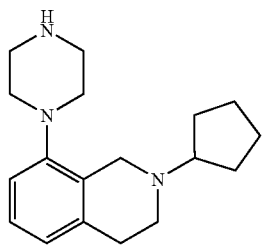

To the compound 46A (250 mg, 0.79 mmol) in DCM (3.6 mL) is added cyclopentanone (0.133 mL, 1.5 mmol), sodium triacetoxyborohydride (469 mg, 2.21 mmol) and acetic acid (0.272 mL, 4.74 mmol), and the reaction is stirred at r.t. for about 24 hours. The reaction is diluted with DCM (50 mL) and washed with 1M NaOH. The organic fraction is concentrated and purified by silica gel chromatography, and the product stirred in 1:1 TFA/DCM (10 mL) for about 2 hours. The reaction is concentrated, and the resulting residue is subjected to SCX ion exchange chromatography followed by silica gel chromatography to give about 162 mg of the final product (79%). EIS-MS 286.2 [M+1]

Preparation 51A

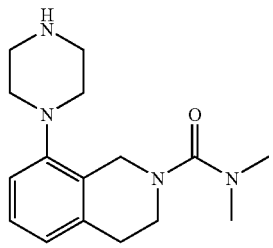

To the compound 46A (400 mg, 1.26 mmol) in DCM (10 mL) is added dimethylcarbamyl chloride (0.329 mL, 3.78 mmol) and TEA (1.05 mL, 7.56 mmol), and the reaction is stirred at r.t. for about 16 hours. The mixture is diluted with DCM (50 mL) and washed with 1M NaOH. The organic fraction is concentrated and purified by silica gel chromatography, and the product is stirred in 1:1 TFA/DCM (10 mL) for about 2 hours. The reaction is concentrated, and the residue subjected to SCX ion exchange chromatography followed by silica gel chromatography to give about 371 mg of the final product. EIS-MS 289.1 [M+1]

Preparation 52A

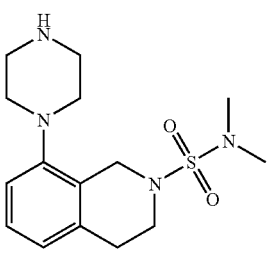

To the compound 46A (400 mg, 1.26 mmol) in DCM (10 mL) is added dimethylsulfamoyl chloride (0.406 mL, 3.78 mmol) and TEA (1.05 mL, 7.56 mmol), and the mixture is stirred at r.t. for about 16 hours. The mixture is diluted with DCM (50 mL) and washed with 1M NaOH. The organic fraction is concentrated and purified by silica gel chromatography, and the product stirred in 1:1 TFA/DCM (10 mL) for about 2 hours. The mixture is concentrated, and the residue subjected to SCX ion exchange chromatography followed by silica gel chromatography to give about 422 mg of the final product. EIS-MS 325.1 [M+1]

Preparation 53A

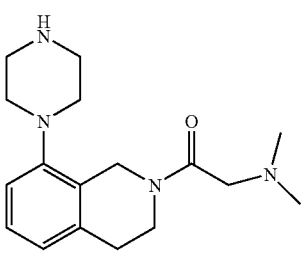

To the compound 46A (400 mg, 1.26 mmol) in DCM (10 mL) is added N,N-dimethyl glycine (130 mg, 1.26 mmol), EDC (242 mg, 1.26 mmol), HOBT (170 mg, 1.26 mmol) and DIPEA (0.44 mL, 1.26 mmol), and the mixture is stirred at r.t. for about 16 hours. The mixture is diluted with DCM (50 mL) and washed with 1M NaOH. The organic fraction is concentrated and purified by silica gel chromatography, and the product is stirred in 1:1 TFA/DCM (10 mL) for about 2 hours. The reaction is concentrated, and the residue is subjected to SCX ion exchange chromatography followed by silica gel chromatography to give about 348 mg of the final product (91%). EIS-MS 303.2 [M+1]

Preparation 54A

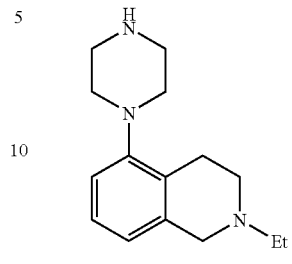

Step 1: 5-Bromoisoquinoline (250 mg, 1.2 mmol) is dissolved in toluene (5 mL). To the solution is added piperazine (258 mg, 3.0 mmol), $Pd_2dba_3$ (55 mg, 0.06 mmol), BINAP (112 mg, 0.18 mmol), and sodium t-butoxide (162 mg, 1.68 mmol). The mixture is degassed and then heated to 90° C. for about 12 hours. The reaction is allowed to cool to r.t., diluted with diethyl ether and filtered through celite. The filtrate is concentrated, and the dark residue is chromatographed on silica gel to give about 160 mg of 5-(piperazin-1-yl)isoquinoline (63%). EIS-MS: Found 214.0 (M+1).

Step 2: 5-(Piperazin-1-yl)isoquinoline is dissolved in DCM, and $Boc_2O$ (620 mg, 2.84 mmol) is added in one portion. The reaction mixture is stirred at r.t. for about 4 hours under nitrogen and concentrated under vacuum. The residue is purified by chromatography on silica gel to give about 201 mg of 5-(4-t-butyloxycarbonylpiperazin-1-yl)isoquinoline (92%).

Step 3: The compound of Step 2 (200 mg, 0.64 mmol) is dissolved in absolute ethanol (50 mL), and Pt/C 10% catalyst (200 mg) is added. The mixture is pressurized to 45 psi under hydrogen and shaken for about 4 hours at r.t. The mixture is filtered over celite, concentrated and chromatographed on silica gel to give about 68 mg of 5-(4-t-butyloxycarbonylpiperazin-1-yl)-2-ethyl-1,2,3,4-tetrahydroisoquinoline (30%).

Step 4: The compound of Step 3 (68 mg, 0.196 mmol) is dissolved in DCM (1.5 mL) and TFA (1.5 mL) and the mixture is stirred for about 1.5 hours. The mixture is concentrated to an oil, which is then purified to afford about 50 mg of the final compound.

Preparation 55A

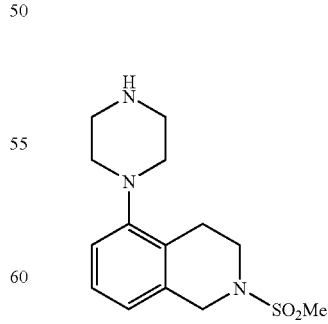

5-(4-t-Butyloxycarbonylpiperazin-1-yl)-1,2,3,4-tetrahydroisoquinoline is treated to the methyl sulfonylation and then deprotection as described in Steps 2 and 3 of Preparation 70A to afford about 45 mg of the final compound (80%).

Preparation 56A

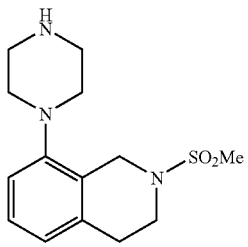

Step 1: 8-(Piperazin-1-yl)isoquinoline is prepared from 8-bromoisoquinoline and piperazine using the coupling procedure as described in Step 1 of Preparation 54A to afford about 270 mg (88%). EIS-MS 214.0 M+1

Step 2: 8-(Piperazin-1-yl)isoquinoline (250 mg, 1.17 mmol) is dissolved in DCM (15 mL). Boc$_2$O (1.02 g, 4.69 mmol) is added in one portion. The mixture is stirred for about 2 hours at r.t. and then concentrated. The residue is chromatographed on silica gel to give about 327 mg of 8-(4-t-butyloxycarbonyl-piperazin-1-yl)isoquinoline (89%).

Step 3: The compound of Step 2 (2.8 g, 8.93 mmol) is dissolved in isopropanol (120 mL), and platinum oxide (1 g) is added. The mixture is pressurized to 45 psi under hydrogen and allowed to react for about 12 hours. The mixture is filtered, concentrated and chromatographed to give about 1.98 g of 8-(4-t-butyloxycarbonyl-piperazin-1-yl)-1,2,3,4-tetrahydroisoquinoline (70%).

Step 4: The compound of Step 3 is treated to the methyl sulfonylation and deprotection as described in Preparation 70A to afford about 100 mg of the final compound (77%). EIS-MS 296.1 M+1

Preparation 57A

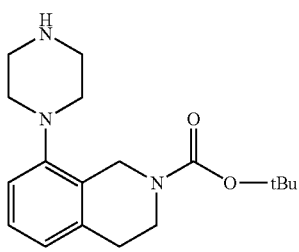

Step 1: 8-(Piperazin-1-yl)isoquinoline (250 mg, 1.17 mmol) is placed in DCM (5 mL) with pyridine (283 microliters, 3.51 mmol), and trifluoroacetic anhydride (182 microliters, 1.29 mmol) is added dropwise for about 5 minutes. The mixture is stirred at r.t. for about 4 hours and then diluted with DCM and washed with water. The water is extracted with diethyl ether, and the organic extracts are combined, dried, filtered and concentrated to afford a crude mixture containing 8-(4-trifluoroacetyl-piperazin-1-yl)isoquinoline, which is carried forward without further purification. EIS-MS 310.3 M+1

Step 2: The mixture from Step 1 is dissolved in isopropanol (75 mL), and Pt/C 10% (200 mg) is added. The mixture is pressurized to 45 psi for about 12 hours and then filtered and concentrated. The residue is purified via chromatography on silica gel to give about 35 mg of 8-(4-trifluoroacetyl-piperazin-1-yl)-1,2,3,4-tetrahydroisoquinoline.

Step 3: The compound of Step 2 (35 mg, 0.14 mmol) is dissolved in DCM (5 mL), and Boc$_2$O (46 mg, 0.14 mmol) is added. The mixture is stirred under nitrogen at r.t. for about 2 hours. The mixture is then concentrated in vacuo and plug filtered on silica gel. The filtrate is dissolved in a 2M methanolic solution of ammonia (5 mL) and stirred at r.t. under nitrogen overnight. The mixture is evaporated to dryness to afford about 45 mg of the final product.

Preparation 58A

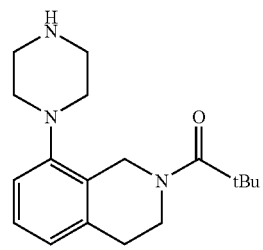

8-(4-t-butyloxycarbonyl-piperazin-1-yl)-1,2,3,4-tetrahydroisoquinoline (150 mg, 0.47 mmol) is dissolved in DCM (5 mL), and Et$_3$N (786 microliters, 3.76 mmol) is added. To the stirred system is added pivaloyl chloride (232 microliters, 1.88 mmol) by syringe under nitrogen. The mixture is stirred for about 3 hours at r.t. and then concentrated under vacuum. Chromatography on silica gel afforded the Boc-protected compound, which is dissolved in DCM (2.5 mL) and TFA (2.5 mL) and stirred at r.t. for about 3 hours. The solution is concentrated and the residue is purified by SCX chromatography to afford about 44 mg of the final compound (31%).

Preparation 59A

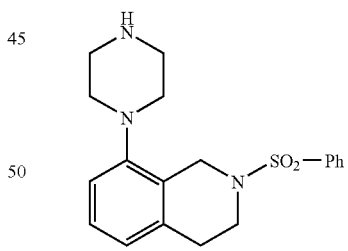

8-(4-t-butyloxycarbonyl-piperazin-1-yl)-1,2,3,4-tetrahydroisoquinoline (127 mg, 0.40 mmol) is dissolved in DCM (5 mL), and Et$_3$N (446 microliters, 3.2 mmol) is added. To the stirred mixture is added phenyl sulfonyl chloride (204 microliters, 1.6 mmol) by syringe under nitrogen. The mixture is stirred for about 4 hours and then concentrated under vacuum. Chromatography on silica gel affords the Boc-protected product. The protected product is taken up in DCM (2.5 mL) and TFA (2.5 mL) and the resulting mixture is stirred for about 2 hours. The mixture is concentrated and the residue is purified by SCX chromatography to afford about 119 mg of the final compound (83%). EIS-MS 358.1 [M+1]

Preparation 60A

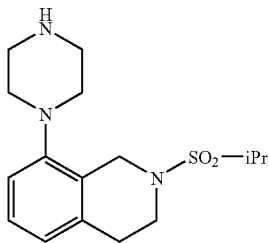

8-(4-t-butyloxycarbonyl-piperazin-1-yl)-1,2,3,4-tetrahydroisoquinoline (127 mg, 0.40 mmol) is dissolved in DCM (5 mL), and Et$_3$N (446 microliters, 3.2 mmol) added. To the stirred solution is added isopropyl sulfonyl chloride (180 microliters, 0.6 mmol) by syringe under nitrogen. The mixture is then stirred for about 4 hours and concentrated under vacuum. Chromatography on silica gel afforded the Boc-protected product, which is taken up in DCM (2.5 mL) and TFA (2.5 mL) and stirred for about 3 hours. The solution is concentrated and the residue is purified by SCX chromatography to afford about 57 mg of the final compound (44%). EIS-MS 322.1 [M+1]

Preparation 61A

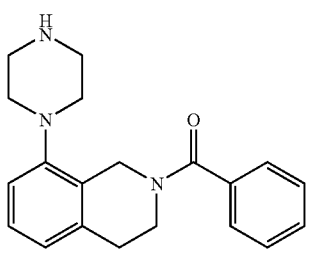

8-(4-t-butyloxycarbonyl-piperazin-1-yl)-1,2,3,4-tetrahydroisoquinoline (127 mg, 0.40 mmol) is dissolved in DCM (5 mL), and Et$_3$N (446 microliters, 3.2 mmol) added. To the stirred solution is added benzoyl chloride (186 microliters, 1.6 mmol) by syringe under nitrogen. The mixture is then stirred for about 4 hours and concentrated under vacuum. Chromatography on silica gel afforded the Boc-protected product, which is taken up in DCM (2.5 mL) and TFA (2.5 mL) and stirred for about 3 hours. The mixture is concentrated and the residue is purified by SCX chromatography to afford about 104 mg of the final compound (82%). EIS-MS 322.1 (M+1).

Preparation 62A

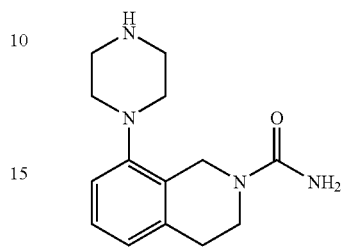

8-(4-t-butyloxycarbonyl-piperazin-1-yl)-1,2,3,4-tetrahydroisoquinoline (250 mg, 0.79 mmol) is dissolved in acetonitrile (5 mL) and DMF (2 mL). To the stirred solution is added sodium cyanate (103 mg, 1.58 mmol). The mixture is heated to 75° C. for about 2 hours and allowed to cool to r.t., which is then stirred for an additional 48 hours. After adding TFA (122 microliters, 1.58 mmol), the mixture is stirred for another hour, which is then concentrated and chromatographed. The resulting product is dissolved in DCM (2 mL) and TFA (2 mL) and stirred for about an hour. The product is concentrated and purified by SCX chromatography to afford about 113 mg of the final compound (55%). EIS-MS 261.1 (M+1)

Preparation 63A

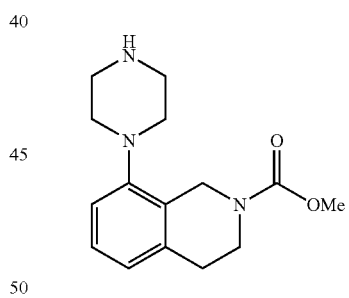

8-(4-t-butyloxycarbonyl-piperazin-1-yl)-1,2,3,4-tetrahydroisoquinoline (250 mg, 0.79 mmol) is dissolved in DCM (5 mL), and Et$_3$N (661 microliters, 4.74 mmol) is added. To the stirred system is added methyl chloroformate (183 microliters, 2.37 mmol) by syringe under nitrogen. The mixture is stirred for about 2 hours and then concentrated under vacuum. The residue is partitioned between DCM and aqueous sodium bicarbonate solution. Chromatography on silica gel of the concentrated organic layer afforded the Boc-protected product, which is taken up in DCM (2.5 mL) and TFA (2.5 mL) and stirred for about 3 hours. The product is concentrated and purified by SCX chromatography to afford about 113 mg of the final compound (52%). EIS-MS 276.1 [M+1]

Preparation 64A

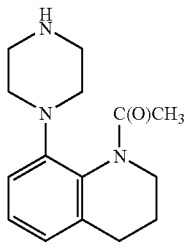

Step 1: 8-(Piperazin-1-yl)quinoline is prepared from 8-bromoquinoline and piperazine as described in Step 1 of Preparation 54A to afford about 490 mg (95%). EIS-MS 207.8 (M+1).

Step 2: 8-(Piperazin-1-yl)quinoline (490 mg, 2.3 mmol) is dissolved in DCM (30 mL), and Boc$_2$O (2 g, 9.2 mmol) is added in one portion. The mixture is stirred for about 2 hours at r.t. and then concentrated. The residue is purified to give about 644 mg of 8-(4-t-butyloxycarbonylpiperazin-1-yl)quinoline (89%).

Step 3: The compound of Step 2 (280 mg, 0.89 mmol) is dissolved in EtOH (70 mL), and Pt/C 10% (300 mg) is added. The mixture is pressurized to 45 psi under hydrogen and reacted for about 4 hours. The mixture is filtered over celite and concentrated. The residue is purified to afford about 266 mg of 8-(4-t-butyloxycarbonylpiperazin-1-yl)-1,2,3,4-tetrahydroquinoline (94%). EIS-MS 318.1 [M+1]

Step 4: The compound of Step 3 (300 mg, 0.95 mmol) is dissolved in acetic anhydride (5 mL) and stirred for about 3 hours at r.t. The mixture is diluted with water and DCM (50 mL/50 mL) and then sodium hydroxide (5M) is added. The organic fraction is concentrated, and the residue is taken up in DCM (2.5 mL) and TFA (2.5 mL), which is then stirred for about an hour. The mixture is concentrated and purified by SCX chromatography to afford about 33 mg of the final compound (13%). EIS-MS 260.2 [M+1]

Preparation 65A

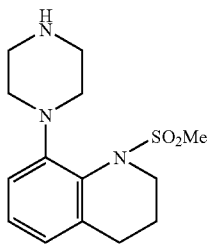

8-(4-t-butyloxycarbonylpiperazin-1-yl)-1,2,3,4-tetrahydroquinoline (200 mg, 0.63 mmol) is dissolved in pyridine (5 mL), and methane sulfonyl chloride (1.86 mL, 12.61 mmol) is added. The mixture is stirred for about 4 hours at r.t., which is then concentrated under vacuum and purified via silica gel chromatography. The Boc-protected product is dissolved in DCM (2.5 mL) and TFA (2.5 mL) and then stirred for about 1.5 hours. The product is concentrated and purified by SCX chromatography to afford about 58 mg of the final compound (31%). EIS-MS: Found 296.1 [M+1]

Preparation 66A

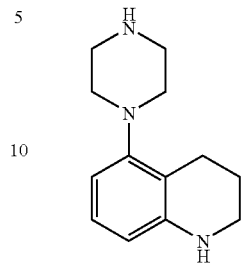

5-Aminoquinoline (5 g, 34.7 mmol) is dissolved in HBr 48% (15 mL) and water (15 mL) and then cooled to 0° C. A solution of NaNO$_2$ (2.5 g, 36.2 mmol) in water (15 mL) is added over about 10 minutes. The mixture is stirred for about 30 minutes at 0° C. and then at r.t. for about 1.5 hours. The mixture is transferred to an addition funnel and 75° C. solution of CuBr is added over 30 minutes. The mixture is stirred for about 30 minutes and then allowed to cool to r.t., which is then stirred for another 2 hours. The mixture is cooled to 0° C. and adjusted to pH of about 14 with 5N NaOH. The solution is filtered, and the solids are washed with DCM. The aqueous layer is extracted with DCM (2×200 mL), and the organic fractions are combined and concentrated. The residue is chromatographed on silica gel to give about 1.6 g of 5-bromoquinoline (22%).

5-Bromoquinoline is converted to 5-(piperazin-1-yl)quinoline by coupling procedure as described in Step 1 of Preparation 54A to afford about 430 mg of the product (84%).

5-(piperazin-1-yl)quinoline (430 mg, 1.98 mmol) is placed in DCM (25 mL), and Boc$_2$O (1.73 g, 7.92 mmol) is added in one portion. The mixture is stirred for about 2 hours, and then concentrated and purified by SCX chromatography. The Boc-protected product is dissolved in isopropanol (75 mL), and Pt/C 5% (400 mg) is added. The mixture is pressurized to 45 psi under hydrogen and shaken for about 4 hours. The mixture is filtered through celite and the product is isolated via chromatography. The material is placed in DCM (10 mL) and TFA (1 mL), and then stirred for about 2 hours. The product is concentrated and purified by SCX chromatography to afford about 45 mg of the final compound (11%).

Preparation 67A

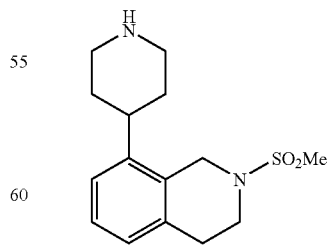

Step 1: 8-Bromoisoquinoline (300 mg, 1.44 mmol) is dissolved in DMF (8.7 mL). To the solution is added Boc-piperidine boronic ester (405 mg, 1.31 mmol), dichloro (1,1'-bis(diphenylphosphino)ferrocene)palladium (II)

dichloromethane adduct (58 mg, 0.079 mmol) and potassium carbonate (544 mg, 3.93 mmol). The mixture is heated to about 90° C. overnight and cooled, which is then diluted with DCM and filtered through celite. The filtrate is concentrated under vacuum to remove DCM and partitioned between EtOAc (100 mL), hexanes (100 mL) and water (100 mL). The organic fraction is concentrated and chromatographed on silica gel to give about 298 mg of 8-(1-t-butyloxycarbonyl-1,2,5,6-tetrahydropyridin-4-yl)isoquinoline (73%). EIS-MS 311.2 M+1

Step 2: The compound of Step 1 (298 mg, 0.96 mmol) is dissolved in isopropanol (100 mL), and platinum oxide is added (500 mg). The mixture is pressurized to 45 psi under hydrogen and shaken overnight. The mixture is filtered, concentrated and chromatographed on silica gel to give about 232 mg of 8-(1-t-butyloxypiperidin-4-yl)-1,2,3,4-tetrahydroisoquinoline (76%). EIS-MS 317.2 M+1

Step 3: The compound of Step 2 (232 mg, 0.73 mmol) is treated to the methyl sulfonylation and then deprotected as described in Preparation 70A. The crude product is concentrated and purified by SCX chromatography to afford about 125 mg of the final product (58%). EIS-MS. 295.1 (M+1)

Preparation 68A

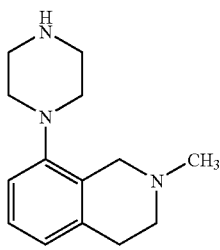

8-Bromoisoquinoline and 1-Boc-piperazine are coupled as described in Step 1 of Preparation 54A. Formaldehyde (0.095 ml, 1.2 mmol, 38% aqueous solution), sodium triacetoxyborohydride (374 mg, 1.8 mmol) in glacial acetic acid (0.23 ml, 3.8 mmol) and 1,2-dichloroethane (3 ml) are added to a slurry of the coupled compound (200 mg, 0.63 mmol). The mixture is stirred for about 16 hours at r.t. under nitrogen, and then 1N NaOH is added. The mixture is diluted with ether (25 ml) and then washed with brine. The ether extract is concentrated under vacuum to give oil. The oil is dissolved in 3 ml of DCM and 1 ml of TFA. The mixture is stirred at r.t. overnight, and then concentrated under vacuum and loaded onto a 10 gram SCX (cation exchange resin). The product is eluted with 2M $NH_3$ in methanol and concentrated under vacuum to afford about 138 mg of the final compound (89%).

Preparation 69A 7-(Piperazin-1-yl)indole

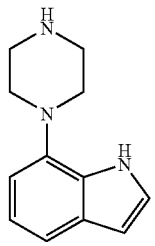

The Boc protected indole (200 mg, 1.5 mmol) prepared from 7-bromoindole and N-Boc piperazine as described in Step 1 of Preparation 54A is dissolved in DCM (1 mL). TFA (1 mL) is added and the mixture is stirred at r.t. for about an hour. The mixture is then concentrated to oil, which is taken up in methanol and freebased via SCX purification to afford about 164 mg (54%) of the final compound.

Preparation 70A

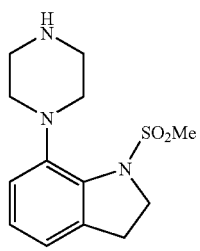

Step 1: 7-(4-t-Butyloxycarbonylpiperazin-1-yl)indole (200 mg, 0.67 mmol) is dissolved in acetic acid (4 mL). To the solution, sodium cyanoborohydride (84 mg, 1.33 mmol) is added. The reaction mixture is stirred for about 2 hours at r.t. The mixture is then diluted with DCM and NaOH (1M) is added. The organic layer is separated, dried and concentrated. The residue is chromatographed on the silica gel and the product containing fractions are combined to give about 93 mg of the 7-(4-t-butyloxycarbonylpiperazin-1-yl)-2,3-dihydroindole (46%).

Step 2: To the compound of Step 1 (94 mg, 0.31 mmol) dissolved in DCM (5 mL), TEA (259 microliters, 1.86 mmol) is added while stirring. Methane sulfonyl chloride (91 microliters, 0.62 mmol) is added by syringe under nitrogen and the mixture is stirred for about an hour at r.t. The mixture is concentrated under vacuum, and the residue is purified on silica gel to give the Boc protected compound (85 mg, 71%).

Step 3: The compound of Step 3 is dissolved in a 1:1 TFA/DCM solution (4 mL) for deprotection, and the mixture is stirred for about 1.5 hour at r.t. The product is concentrated to oil, which is then subjected to SCX purification to afford about 53 mg of the final compound (85%).

Preparation 71A

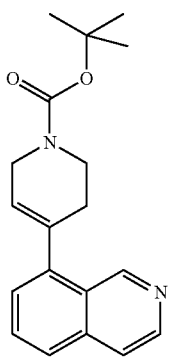

The 1-2 (H)-pyridine-carboxylic acid, 3,6-dihydro-4-(4,4,5,5-tetramethyl-1,3,2-dixoaborolan-2-yl)-1,1-dimethyl ethyl ester (1.35 g, 4.37 mmol, *Tet. Lett.*, 41:3705–3708, 2000), 8-bromoisoquinoline (1 g, 4.8 mmol), dichloro(1,1'bis(diphenylphosphino)ferrocene)palladium (II) DCM adduct (193 mg, 0.263 mmol) and potassium carbonate (1.8 g, 13.1 mmol) are dissolved in DMF (29 mL), degassed and heated at 90° C. for about 4 hours. The reaction is cooled to r.t., diluted with DCM (100 mL) and filtered over celite. The filtrate is concentrated to dryness. The resulting residue is partitioned between 600 mL of 1:1 EtOAc/hexanes and water (200 mL). The organic phase is concentrated and purified by silica gel chromatography to give about 1.07 g of the final product (79%).

Preparation 72A

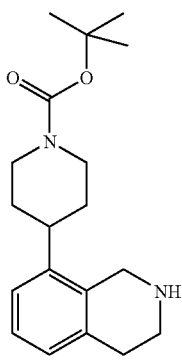

The compound 71A (1.05 g, 3.38 mmol) is dissolved in a slurry Of PtO$_2$ (1 g) in isopropanol (150 mL), and pressurized to 50 psi with hydrogen overnight. The mixture is filtered, concentrated and purified by silica gel chromatography to give about 1.07 g of the final product. EIS-MS 317.2 [M+1]

Preparation 73A

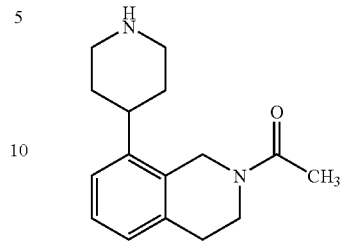

The compound 72A (530 mg, 1.73 mmol) is dissolved in acetic anhydride (10 mL) and TEA (3 mL) is added. The mixture is stirred for about 16 hours, and then concentrated and dissolved in a 1:1 mixture of DCM/TFA (10 mL). The mixture is stirred for about 2 hours and then concentrated. The resulting residue is subjected to SCX ion exchange chromatography followed by silica chromatography to give about 218 mg of the final product (49%). EIS-MS 259.1 [M+1]

Preparation 74A

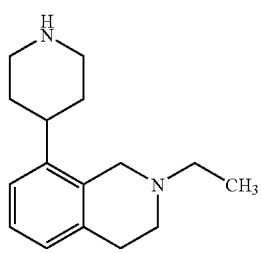

The compound 73A (287 mg, 1.11 mmol) is dissolved in THF (10 mL) and lithium aluminum hydride (169 mg, 4.44 mmol) is added as a slurry in THF (5 mL). The mixture is stirred for about 4 hours at reflux. The reaction is worked up with water, washed with 1M NaOH and purified by silica gel chromatography to give about 215 mg of the final product (79%). EIS-MS 245.2 [M+1]

Preparation 75A

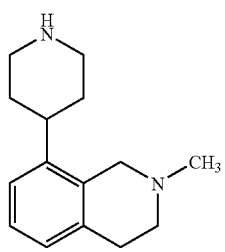

The compound 72A (530 mg, 1.67 mmol) is dissolved in dichloromethane (10 mL) to which is added formaldehyde 38% (8.8 mL, 3.34 mmol), sodium triacetoxyborohydride (1.06 g, 5.02 mmol) and acetic acid (0.6 mL). The mixture is stirred at r.t. for 24 hours. The mixture is diluted with DCM (50 mL) and washed with 1M NaOH. The organic fraction is concentrated and purified by silica gel chromatography. The product is then stirred in 1:1 TFA/DCM (10 mL) for about 2 hours. The reaction is concentrated, and the resulting residue is subjected to SCX ion exchange chromatography followed by silica gel chromatography to give about 171 mg of the final product (44%). EIS-MS 231.2 [M+1]

Preparation 76A

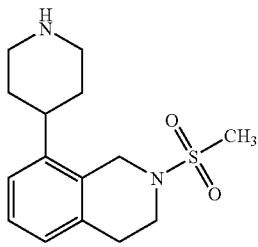

To the compound 72A (225 mg, 0.71 mmol) in DCM (10 mL) is added TEA (1.2 mL, 8.6 mmol) and methane sulfonyl chloride (0.329 mL, 4.3 mmol), and the mixture is stirred at r.t. for about 3 hours. The mixture is diluted with DCM (50 mL) and washed with 1M NaOH. The organic fraction is concentrated and the resulting residue is stirred in 1:1 TFA/DCM (10 mL) for about 2 hours. The mixture is concentrated, and the residue is subjected to SCX ion exchange chromatography followed by silica gel chromatography to give about 125 mg of the final product (60%). EIS-MS 295.0 [M+1]

Preparation 77A

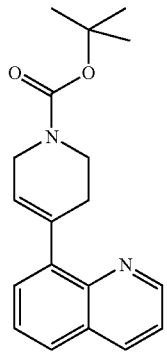

To 1-2 (H)-pyridine-carboxylic acid, 3,6-dihydro-4-(4,4,5,5-tetramethyl-1,3,2-dixoaborolan-2-yl)-1,1-dimethyl ethyl ester (500 mg, 1.62 mmol, *Tet. Lett.*, 41:3705–3708, 2000) in DMF (9 mL) is added 8-bromoquinoline (370 mg, 1.78 mmol), dichloro(1,1'bis (diphenylphosphino)ferrocene) palladium (II) DCM adduct (71 mg, 0.097 mmol) and potassium carbonate (672 mg, 4.86 mmol), and the mixture is degassed and heated at 90° C. for about 4 hours. The mixture is then cooled to r.t., diluted with DCM (100 mL) and filtered over celite. The filtrate is concentrated to dryness. The mixture is partitioned between 1:1 EtOAc/hexanes (600 mL) and water (200 mL). The organic phase is concentrated to dryness, and the resulting residue purified by flash chromatography to give about 230 mg of the final product (74%). EIS-MS 311.1 [M+1]

Preparation 78A

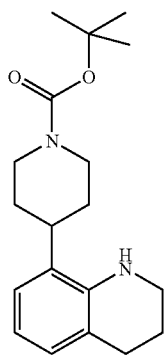

To the compound 77A (270 mg, 0.87 mmol) in acetic acid (4 mL) is added sodium cyanoborohydride (110 mg, 1.75 mmol), and the mixture is stirred for about 4 hours. The mixture is diluted with DCM (100 mL) and made basic with 5N NaOH solution. The organic phase is dried and concentrated, and the resulting residue is dissolved in a slurry of 5% Pt/C (500 mg) in isopropanol (150 mL). The mixture is pressurized to 50 psi with hydrogen overnight. The mixture is filtered, concentrated and purified by silica gel chromatography to give about 175 mg of the final product (65%).

Preparation 79A

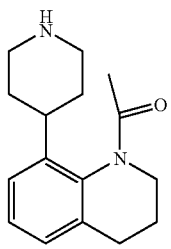

To compound 78A (175 mg, 0.55 mmol) is added acetic anhydride (10 mL) and pyridine (3 mL), and the mixture is stirred for about 16 hours. After concentrating to dryness, the resulting residue is dissolved in a 1:1 mixture of DCM/TFA (10 mL) and stirred for about 2 hours, which is then concentrated to dryness. The resulting residue is subjected to SCX ion exchange chromatography followed by silica gel chromatography to give about 39 mg of the final product (27%). EIS-MS 259.1 [M+1]

Preparation 80A

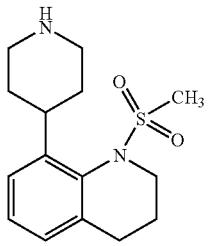

To the compound 78A (555 mg, 1.58 mmol) in pyridine (15 mL) is added methane sulfonyl chloride (2 mL). The mixture is stirred for about 16 hours at r.t. and concentrated, which is then dissolved in a 1:1 mixture of DCM/TFA (10 mL). The mixture is stirred for about 2 hours. After concentrating, the resulting residue is subjected to SCX ion exchange chromatography followed by silica chromatography to give about 218 mg of the final product (47%). EIS-MS 295.1 [M+1]

Preparation of "C Domain"

Preparation 1C

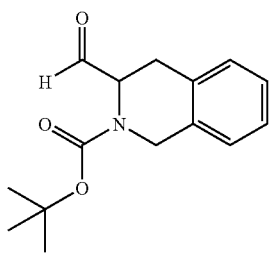

Boc-D-Tic-OH (4.50 g, 16 mmol), methoxymethylamine hydrochloride (1.56 g, 16 mmol), HOBT (2.43 g, 18 mmol), EDC (3.45 g, 18 mmol), DMAP (200 mg, 1.6 mmol), DIPEA (4.2 ml) and THF (150 ml) are combined, and the resulting mixture is stirred for about 18 hours at r.t. The mixture is stripped to dryness, and the resulting residue is taken up in ethyl acetate and then washed with aqueous HCl (1N), aqueous sodium bicarbonate and brine, which is then dried over sodium sulfate. The solvent is removed and the residue is chromatographed on normal phase (ethylacetate/hexanes 1:1) to give about 3.89 g of Boc-D-Tic-NMeOMe (Weinreb amide).

Lithium aluminum hydride (1.0M in THF, 7.2 ml, 7.19 mmol) is slowly added to the Weinreb amide (1.84 g, 5.75 mmol) in THF (50 ml) at 0° C. The mixture is stirred at 0° C. for another 15 minutes. Aqueous KHSO$_4$ (1.37 g in 29 ml H$_2$O) is slowly added followed by diethyl ether. The organic layer is separated, and the aqueous layer is extracted with diethyl ether. The organic phases are combined and washed with aqueous 1M HCl, saturated aqueous NaHCO$_3$ solution and brine, which is then dried over Na$_2$SO$_4$. Removal of solvent affords about 1.44 g of the epimerized compound. EIS-MS: MH$^+$ 262 [M+1]

Preparation 2C

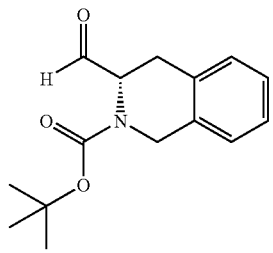

The above compound was prepared from Boc-L-Tic-OH as described in Preparation 3C below, except that the Weinreb amide was made by a similar procedure to that described in *Synthesis*, 676, 1983.

Preparation 3C

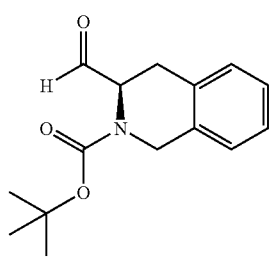

Boc-D-Tic-OH (14.9 g, 53.7 mmol), methoxymethylamine hydrochloride (5.24 g, 53.7 mmol), EDC (11.3 g, 59.1 mmol); HOBT (7.98 g, 59.1 mmol), DIPEA (9.83 ml, 59.1 mmol) and THF (500 ml) are combined, and the resulting mixture is stirred for about 18 hours at r.t. under nitrogen. The mixture is stripped to dryness, and the residue is taken up in ethyl acetate. The resulting mixture is washed with 1M HCl, saturated NaHCO$_3$ and brine, and then dried. Solvent is removed and the residue is chromatographed on normal phase using 1:1 ethylacetate/hexane to give about 12.3 g of Boc-D-Tic-NMeOMe (Weinreb amide).

Lithium aluminum hydride (1.0M in THF, 5.1 ml, 5.00 mmol) is slowly added to the Weinreb amide (1.28 g, 4.00 mmol) in THF (35 ml) at 0° C. The mixture is stirred at 0° C. for another 15 minutes. Aqueous KHSO$_4$ (970 mg in 20 ml H$_2$O) is slowly added followed by diethyl ether. The organic layer is separated, and the aqueous layer is extracted with diethylether. The organic phases are combined and washed with aqueous 1M HCl, saturated aqueous NaHCO$_3$ and brine, which is then dried over Na$_2$SO$_4$. Removal of solvent affords about 780 mg of the final compound. EIS-MS: MH$^+$ 262 [M+1]

Preparation 4C

1-Methoxycarbonylmethyl-1,3-dihydro-isoindole-2-carboxylic acid tert-butyl ester

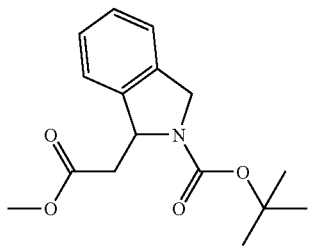

Step A: (2-Bromo-benzyl)-carbamic acid tert-butyl ester

To a mixture of 125.0 g (561.8 mmol) of 2-bromobenzylamine hydrochloride and 170.7 g (1236.0 mmol) of potassium carbonate in 300 mL of 50% THF/water is added 134.9 g (618.0 mmol) of di-tert-butyl dicarbonate in four portions over 20 minutes. The mixture is stirred at r.t. for about 16 hours and then diluted with 300 mL of ethyl acetate and 300 mL of water. The organic portion is separated and the aqueous portion is extracted three times with 200 mL each of ethyl acetate. The combined ethyl acetate portions are washed once with 250 mL of 10% aqueous sodium bisulfate. The organic portion is dried (MgSO4), filtered and concentrated to dryness to afford about 161 g Step A compound.

Step B: 3-[2-(tert-Butoxycarbonylamino-methyl)-phenyl]-acrylic acid methyl ester To compound of Step A (161.0 g, 561.8 mmol) in DMF (800 mL) is added methyl acrylate (58.0 g, 674.2 mmol), TEA (170.5 g, 1685.4 mmol) and dichlorobis(triphenylphosphine)palladium(II) (7.9 g, 11.2 mmol). The mixture is heated at 80° C. for about 32 hours. The mixture is cooled, diluted with 1000 mL of EtOAc and washed with 10% aqueous sodium bisulfate. The aqueous portion is extracted three times with EtOAc and the combined organics are dried (Na₂SO₄) and concentrated to dryness. The residue is dissolved in a small amount of DCM and filtered through 7 inch of silica gel in a 2 L sintered glass funnel eluting with 25% EtOAc/hexanes. The eluent is concentrated to dryness and recrystallized from EtOAc/hexanes to afford about 116.9 g (71%) of Step B compound.

Step C: To a 0° C. solution of (116.9 g, 401.2 mmol) material from Step B in DCM (800 mL) is added 200 mL of TFA dropwise over 15 minutes. After removing the cooling bath, the mixture is stirred for about 2.5 hours and then concentrated to dryness. The residue is dissolved in 500 mL of DCM and saturated aqueous sodium bicarbonate is slowly added until the mixture is slightly basic. The organic portion is separated and the aqueous portion is extracted two times with DCM. The combined organic portions are dried (Na₂SO₄) and concentrated to dryness. The residue is dissolved in 800 mL of DCM and DIPEA (57.0 g, 441.4 mmol) is added. To the mixture is added di-tert-butyl dicarbonate (96.3 g, 441.4 mmol) in five portions over 45 minutes and then stirred at room temperature for 16 h. The mixture is washed with 10% aqueous sodium bisulfate, and the organic portion is separated and the aqueous portion is extracted two times with DCM. The combined organic extracts are dried ((Na₂SO₄) and concentrated to dryness. The resulting residue is dissolved in a small amount of DCM and filtered through 7 inch silica gel in a 2 L sintered glass funnel eluting with 25% EtOAc/hexanes. The eluent is concentrated to dryness and the enantiomers are separated by chiral chromatography. The first eluting isomer is labeled as isomer #1 and the second eluting is labeled as isomer #2, which affords about 52.6 g (45%) of the final compound (isomer 2). EIS-MS 292 [M+1]

Preparation 5C

1-Carboxymethyl-1,3-dihydro-isoindole-2-carboxylic acid tert-butyl ester

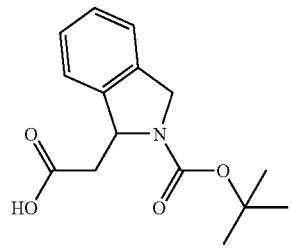

To the compound 4C (52.6 g, 180.5 mmol) in MeOH (500 mL) is added 1N NaOH (199 mL, 199.0 mmol). The mixture is stirred at r.t. for about 48 hours and then concentrated to dryness. The resulting residue is dissolved in water (300 mL) and extracted with diethyl ether (2×). The aqueous portion is acidified to pH 2 with 10% aqueous sodium bisulfate and extracted with EtOAc. The combined organic extracts are dried (MgSO₄) and concentrated to dryness to afford about 49.8 g of the final compound (99%). EIS-MS 276 [M−1].

Preparation 6C

1-Carboxymethyl-3,4-dihydro-1H-isoquinoline-2-carboxylic acid tert-butyl ester, lithium salt

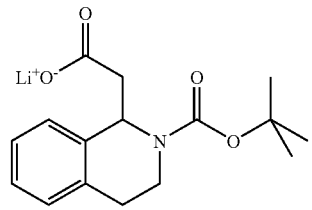

Step A: (1,2,3,4-Tetrahydro-isoquinolin-1-yl)-acetic acid methyl ester

To Boc-tetrahydoisoquinoline-1-acetic acid (100.4 g, 520.0 mmol) in MeOH (200 mL) is added 400 mL of 2.3 M HCl in methanol. The mixture is stirred overnight and then concentrated to dryness. The resulting residue is dissolved in EtOAc and washed with saturated sodium bicarbonate and brine, which is then dried (Na₂SO₄) and concentrated to dryness to afford about 109.5 g (100%) of the ester. EIS-MS 206 [M+1]

Step B: 1-Methoxycarbonylmethyl-3,4-dihydro-1H-isoquinoline-2-carboxylic acid tert-butyl ester To a 0° C. solution of compound from Step A (50.5 g, 240.0 mmol) in THF (250 mL) is added di-tert-butyl dicarbonate (59.3 g, 270.0 mmol) in THF (50 mL) dropwise. After stirring for about 45 minutes, the mixture is concentrated to dryness. The resulting residue is dissolved in EtOAc and washed with saturated sodium bicarbonate and brine, which is then dried ($Na_2SO_4$) and concentrated to dryness. Chiral chromatography of the residue affords both enantiomers, the first eluting isomer being labeled as isomer 1 and the second as isomer 2. EIS-MS 306 [M+1]

Step C: To a solution of compound B from Step B (10.2 g, 33.4 mmol) in dioxane (220 mL) is added a solution of lithium hydroxide monohydrate (1.67 g, 39.8 mmol) in water (110 mL) portion wise while maintaining a temperature below 30° C. The mixture is stirred for about 16 hours and then concentrated to dryness, which gives about 11.2 g of the final compound. EIS-MS 292 [M+1]

Preparation 7C (2-isopropyl-2,3-dihydro-1H-isoindol-1-yl)-acetic acid

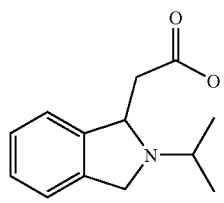

Step A: (2,3-dihydro-1H-isoindol-1-yl)-acetic acid methyl ester

To the compound prepared in Preparation C1 (11.75 g., 40.41 mmol) in DCM (50 mL) was added TFA (50 mL) dropwise. After about 2 hours, the mixture was concentrated to dryness and the resulting residue was partitioned with saturated aqueous sodium bicarbonate (200 mL) and EtOAc (300 mL). The organic portion was separated and the aqueous layer was extracted with DCM (4×500 mL). The combined DCM extracts were combined, dried ($Na_2SO_4$), and concentrated to dryness to afford about 3.97 g (51%).

Step B: (2-isopropyl-2,3-dihydro-1H-isoindol-1-yl)-acetic acid methyl ester

To the compound obtained from Step A (0.50 g, 2.61 mmol) in dichloroethane (46 mL) was added acetone (1.76 mL, 24.01 mmol) and sodium triacetoxyborohydride (2.48 g., 11.74 mmol). After 6 hours, the mixture was diluted with 1.0N NaOH (100 mL), and the organic portion was separated. The aqueous layer was extracted with DCM (3×100 mL). The combined DCM extracts were dried ($MgSO_4$) and concentrated to dryness to afford about 0.60 g (99%). EIS-MS 235 [M+1].

Step C: To the compound of Step B (0.53 g., 2.30 mmol) in MeOH (5.1 mL) was added 1.0N NaOH (2.53 mL, 2.53 mmol). After two days, the solution was concentrated to dryness. The resulting residue was diluted with 1.0N HCl and water was loaded onto a strong cation exchange resin. The resin was washed with water, THF/water (1:1) and then water. The product was then eluted from the resin with pyridine/water (1:9). The eluent was concentrated to dryness to afford about 0.43 g (85%) of the final compound. EIS-MS 220 [M+1].

Preparation 8C (2-Methyl-2,3-dihydro-1H-isoindol-1-yl)-acetic acid

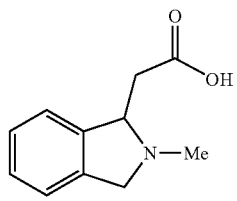

Step A: (2-Methyl-2,3-dihydro-1H-isoindol-1-yl)-acetic acid methyl ester

The compound from preparation C1 was deprotected with TFA in a manner similar to preparation 3C of Step A. To the deprotected compound (0.50 g, 2.61 mmol), in dichloroethane (46 mL), was added 37% aqueous formaldehyde solution (1.80 mL, 24.01 mmol) and sodium triacetoxyborohydride (2.48 g., 11.74 mmol). After 3 days, the mixture was diluted with 1.0N NaOH (100 mL). The organic portion was separated and the aqueous layer was extracted with DCM (3×100 mL). The combined DCM extracts were dried ($Na_2SO_4$) and concentrated to dryness. The resulting residue was purified by flash chromatography ($SiO_2$, eluting with 100% EtOAc) affording about 0.43 g (79%) of the alkylated isoindole. EIS-MS 206 [M+1].

Step B: To the compound of Step A (0.34 g., 1.66 mmol) in MeOH (3.7 mL) was added 1.0N NaOH (1.82 mL, 1.82 mmol). After 2 days, the solution was concentrated to dryness. The resulting residue was diluted with 1.0N HCl and water was then loaded onto a strong cation exchange resin. The resin was washed with water, THF/water(1:1) and water, and the product was eluted from the resin with pyridine/water(1:9). The eluent was concentrated to dryness to afford about 0.31 g (98%) of the final compound. EIS-MS 192 [M+1].

Preparation 9C (2-Butyl-2,3-dihydro-1H-isoindol-1-yl)-acetic acid methyl ester

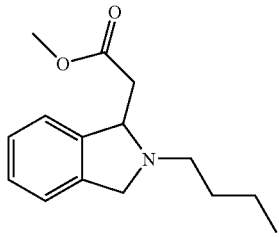

The compound from preparation C1 was deprotected with TFA in a manner similar to preparation 3C of Step A. To the deprotected compound (0.50 g, 2.61 mmol) and butryaldehyde (2.16 mL, 24.01 mmol) in dichloroethane (46 mL) was added sodium triacetoxyborohydride (2.48 g., 11.74 mmol). After reacting about 3 hours, the mixture was diluted with 1.0 N NaOH (100 mL) and partitioned. The aqueous layer was extracted with DCM (3×75 mL). The DCM layers were combined, dried over sodium sulfate, filtered and concentrated under reduced pressure to give a brown residue. The residue was purified via silica gel chromatography (eluent: ethyl acetate/hexanes (1:3). The purified fractions were combined and concentrated to give the title compound as a brown oil (0.51 g, 77%). MS ES 249.2 (M+H)

Preparation 10C (2-Butyl-2,3-dihydro-1H-isoindol-1-yl)-acetic acid

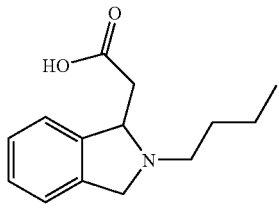

To a solution containing the compound 7C (0.47 g, 1.89 mmol) in methanol (4.2 mL) was added 1.0 N NaOH (2.08 mL, 2.08 mmol). After reacting about 2 hours, the solution was concentrated under reduced pressure. The residue was diluted with 1.0 N HCl, and water was loaded onto a strong cation exchange resin. The resin was washed with water and THF/water (1:1), and the product was eluted from the resin with pyridine/water (1:9). The pyridine washes were concentrated under reduced pressure, and azeotroped with acetone to give the title compound as brown solids (0.28 g., (64%)) MS ES 234.19 (M+H)

Preparation 11C

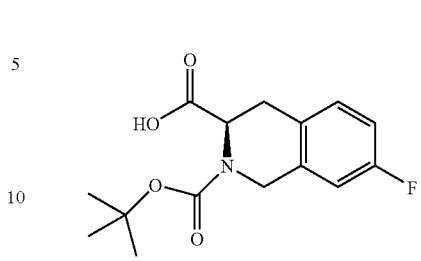

Step A: To a solution of N-Boc-4-Fluoro-D-Phe (2.37 g, 8.366 mmol) in methanol, 3 mL of concentrated sulfuric acid was added. The mixture was heated to reflux overnight and then concentrated in vacuo. MS M+1 198.1

Step B: To an ice cold mixture of 1.65 g (8.367 mmol) of compound from Step A, 1.353 mL of pyridine and ethyl chloroformate (0.848 mL, 8.869 mmol) is added slowly with stirring for about 30 minutes giving white solid. The mixture was partitioned between water and ethyl acetate. The aqueous layer was extracted with EtOAc (2×). The combined organic solution was dried over $MgSO_4$, filtered, and concentrated in vacuo to give about 2.17 g of yellow oil (96%). MS M+1 270.1.

Step C: A mixture containing 2.17 g (8.06 mmol) of the compound from Step B, paraformaldehyde (0.254 g, 8.46 mmol), and 10 mL of 3:1 glacial acetic acid/conc. sulfuric acid was stirred at r.t. for about 48 hours. The mixture was partitioned between water and ethyl acetate. The aqueous layer was extracted with EtOAc (3×). The combined EtOAc solution was dried over magnesium sulfate, filtered, and concentrated in vacuo. The desired product was purified by column chromatography eluting with 25% EtOAc in Hexane to give about 1.31 g (58%) of colorless oil. MS: M+1 282.1

Step D: A solution of 1.31 g (4.656 mmol) of material from Step C in 20 mL of 5N HCl was heated to reflux for about 24 hours. The solution was concentrated in vacuo. The resulting white solid was washed with ether to afford about 0.87 g (81%). MS M+1 196.1.

Step E: To a solution of 0.87 g (3.755 mmol) of material from Step D in 20 ml of 1:1 dioxane/water, di-t-butyl-dicarbonate (0.901 g, 4.131 mmol) and 2.355 mL (16.90 mmol) of TEA were added. The mixture was allowed to stir at r.t. overnight. The mixture was diluted with EtOAc, and the separated aqueous layer was extracted with EtOAc (3×). The combined organic solution was dried over magnesium sulfate, filtered and concentrated in vacuo to give about 0.64 g (58%)of the final compound. MS M−1 294.1.

Preparation 12C

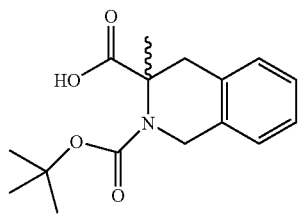

Step A: By following a procedure of Preparation 28C, Step A and 1.0 g (5.58 mmol) of □-methyl-DL-phenylanaline, about 1.4 g of ester was prepared. MS M+1 194.1

Step B: By following a procedure of Preparation 28C, Step B and 1.08 g (5.59 mmol) of material from Step A, about 1.48 g (100%) of product was prepared. MS M+1 266.1

Step C: By following a procedure of Preparation 28C, Step C and 1.48 g (5.59 mmol) of material from Step B, about 1.55 g (100%) of product was prepared. MS M+1 278.1

Step D: By following a procedure of Preparation 28C, Step D and 1.55 g (5.59 mmol) of material from Step C, about 1.33 g of product was prepared. MS M+1 192.1

Step E: By following a procedure of Preparation 28C, Step E and 1.33 g (5.84 mmol) of material from Step D, about 1.70 g (100%) of the final compound was prepared. MS M+1 292.2

Preparation 13C

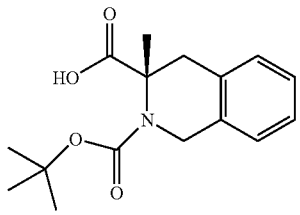

Step A: By following a procedure of Preparation 28C, Step A and 2.0 g (11.16 mmol) of □-methyl-D-phenylanaline, about 2.15 g of ester was prepared. MS M+1 194.1

Step B: By following a procedure of Preparation 28C, Step B and 2.15 g (11.16 mmol) of material from Step A, about 1.46 g (49%) of product was prepared. MS M+1 266.1

Step C: By following a procedure of Preparation 28C, Step C and 1.46 g (5.503 mmol) of material from Step B, about 0.74 g (48%) of product was prepared. MS M+1 278.1

Step D: By following a procedure of Preparation 28C, Step D and 0.74 g (2.67 mmol) of material from Step C, about 0.54 g (89%) of product was prepared. MS M+1 192.1

Step E: By following a procedure of Preparation 28C, Step E and 0.54 g (2.37 mmol) of material from Step-D, about 0.54 g (78%) of the final compound was prepared. MS M+1 292.2

Preparation 14C

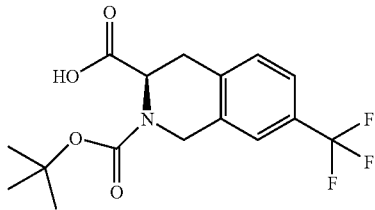

Step A: By following a procedure of Preparation 28C, Step A and 0.65 g (1.95 mmol) of N-Boc-4-trifluoromethyl-D-phenylanaline, about 0.48 g of ester was prepared. MS M+1 248.0

Step B: By following a procedure of Preparation 28C, Step B and 0.48 g (1.95 mmol) of material from Step A, about 0.60 g (96%) of product was prepared. MS M+1 320.1

Step C: By following a procedure of Preparation 28C, Step C and 0.6 g (1.879 mmol) of material from Step B, about 0.37 g (59%) of product was prepared. MS M+1 332.1

Step D: By following a procedure of Preparation 28C, Step D and 0.37 g (1.117 mmol) of material from Step C, about 0.11 g (35%) of product was prepared. MS M+1 246.1

Step E: By following a procedure of Preparation 28C, Step E and 1.11 g (0.391 mmol) of material from Step D, about 0.234 g (>100%) of the final compound is prepared. MS M−1 344.1

Preparation 15C lithium; (2-methyl-1,2,3,4-tetrahydro-isoquinolin-1-yl)-acetate

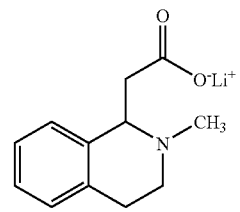

Step 1: (1,2,3,4-Tetrahydro-isoquinolin-1-yl)-acetic acid methyl ester

The material from Preparation of 13C Step 2 (9.98 g, 32.7 mmol) was mixed with 500 mL cold 4M HCl/dioxane and stirred at r.t. for about an hour. The mixture was concentrated in vacuo. The residue was dissolved in ethyl acetate and then washed with saturated sodium bicarbonate and brine. The organic portion was dried ($Na_2SO_4$), filtered and concentrated in vacuo to afford about 6.9 g (100%) of the title compound. EIS-MS: 206 (M+1).

Step 2: (2-methyl-1,2,3,4-tetrahydro-isoquinolin-1-yl)-acetic acid methyl ester

To a solution of material from Step 1 (6.71 g, 32.0 mmol) in 175 mL of dichloroethane was added 37% aqueous formaldehyde (22.6 mL, 300 mmol). After about 10 minute, sodium triacetoxyborohydride (31.2 g, 147.0 mmol) was added in 2 to 3 g portions with some cooling to maintain ambient temperature. The mixture was stirred for about 16 hours and DCM and water was added. The mixture was adjusted to pH 9–10 with 5N sodium hydroxide. The organic layer was separated, washed with brine, and then dried ($Na_2SO_4$) and concentrated in vacuo. Chromatography (silica gel, 5% (2N ammonia in methanol)/DCM) of the residue afforded about 6.9 g (96%) of the title compound. EIS-MS: 220 (M+1).

Step 3: To a solution of material from Step 2 (4.45 g, 18.9 mmol) in 120 mL dioxane was added lithium hydroxide monohydrate (1.02 g, 22.7 mmol) in 65 mL water in portions keeping the temperature below 30° C. After about 16 hours, the mixture was concentrated in vacuo to afford about 8.12 g of the final compound. EIS-MS: 206 (M+1).

Preparation 16C 1,1-Dimethyl-6-methoxy-1,2,3,4-tetrahydroisoquinoline-3-carboxylic acid ethyl ester

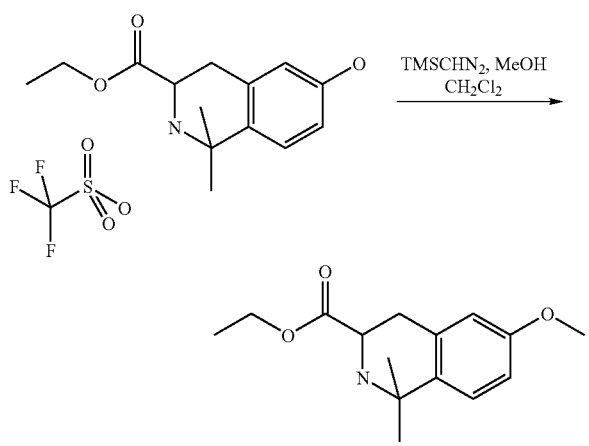

To a solution of the triflate salt of 1,1-dimethyl-1,2,3,4-tetrahydroisoquinoline-3-carboxylic acid ethyl ester (1.5 g, 3.76 mmol, 1.0 eq.) in MeOH (20 mL) and CH$_2$Cl$_2$ (2 mL) at 0° C. was added a solution of (trimethylsilyl)diazomethane (2.0 M in hexane, 3.7 mL, 2.0 eq.). The resulting mixture was warmed to r.t. and stirred overnight, and then the solution was concentrated. Purification by flash chromatography (125 g SiO$_2$ linear gradient, 40 mL/min, 1:1 EtOAc/hexane for 33 minutes) afforded about 900 mg of the final compound (96%). LRMS (electrospray): 250.2 (M+1).

"B Domain" and "C Domain" Combination

Preparation 1BC

3-[2-(4-Chloro-phenyl)-1-methoxycarbonyl-ethylcarbamoyl]-3,4-dihydro-1H-isoquinoline-2-carboxylic acid tert-butyl ester (N-Boc-D-Tic-4-Cl-D-phe-OH)

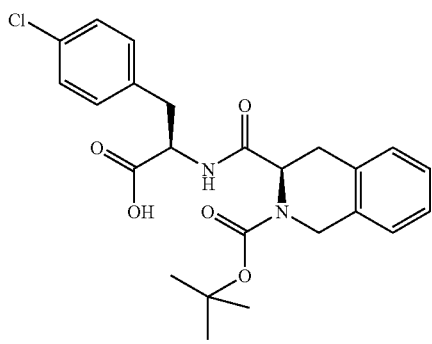

Step A: To a 0° C. solution of 4-Cl-D-Phe methyl ester (23.8 g, 111.0 mmol), Boc-D-Tic (30.8 g, 111.0 mmol) and 4-DMAP (75 mg, 0.61 mmol) in 200 mL of DCM is added EDC (30.8 g, 111.0 mmol) and the mixture is stirred for about 20 minutes. The ice bath is removed and the mixture is stirred at r.t. for about 4 hours. After washing with water (4×200 mL), the combined aqueous portions are back extracted with DCM (2×200 mL). The combined organic portions are washed with brine, dried (MgSO$_4$) and concentrated to dryness. The desired product is purified by flash chromatography (SiO$_2$, eluting with 35% EtOAc in Hexanes) to afford about 43.0 g (83%) of the ester. EIS MS 473 [M+1]

Step B: To the compound of Step A (43.0 g, 91.0 mmol) in MeOH (170 mL) at 0° C. is added 1N NaOH (227.0 mL, 227.0 mmol) dropwise. After about 20 minutes, the ice bath was removed and the mixture is stirred at r.t. for about 3 hours. The mixture is concentrated to dryness, and the resulting residue is suspended in 200 mL of water. The aqueous layer is adjusted to about pH 1 with 5 N HCl and then extracted with EtOAc (4×200 mL). The combined organics are dried (MgSO$_4$) and concentrated to dryness yielding about 39.0 g (93%) of the final compound. EIS-MS 459 [M+1]

Preparation 2BC

Boc-L-Tic-4-Cl-D-phe-OH

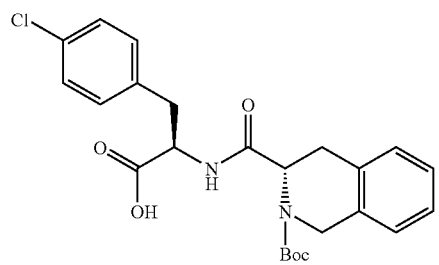

Boc-L-Tic-4-Cl-D-phe-OMe is prepared as described in Preparation 1BC of Step A. $^1$HNMR(DMSO) (two rotamers observed) δ8.40(d, 1H), 8.32(d, 0.5 H), 7.32(d, 2H), 7.25(d, 0.5H), 7.18(d, 2H), 7.00–7.16(m, 4.5H), 6.88(m, 2H), 4.74 (m, 0.5H), 4.27–4.60(m, 4.5H), 3.58(s, 3H), 3.56(s, 1.5H), 2.60–3.07(m, 6H), 1.42(s, H), 1.21(s, 9H). MS(ES) 473.0 (M$^+$), 471.1(M$^-$).

Boc-L-Tic-4-Cl-D-phe-OH is converted to Boc-L-Tic-4-Cl-D-phe-OH—OH according to the procedure described in Preparation 1BC of Step B. $^1$H NMR (DMSO) (Two rotamers observed) δ7.98 (d, 1H), 7.72 (d, 0.5 H), 6.90–7.41 (m, 16H), 4.0–4.70 (m, 8.5H), 2.60–3.20 (m, 8.5H), 1.32–1.41 (m, 19H). MS(ES) 459.1 m/z(M$^+$), 457.1(M$^-$).

Preparation 3BC

1-{[1-Carboxy-2-(4-chloro-phenyl)-ethylcarbamoyl]-methyl}-1,3-dihydro-isoindole-2-carboxylic acid tert-butyl ester

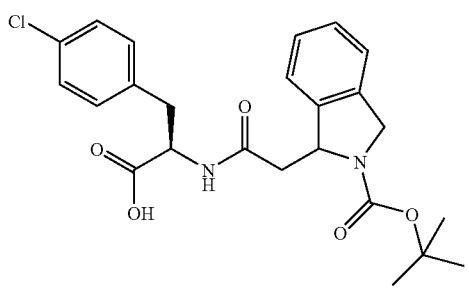

Step A: To a suspension of 4-Cl-D-Phe methyl ester hydrochloride (40.4 g, 161.5 mmol) in DCM (250 mL), is added saturated aqueous sodium bicarbonate (250 mL) and the mixture is stirred at r.t. for about one hour. The organic portion is separated and the aqueous portion is extracted with DCM (2×). The combined organic portions are dried ($Na_2SO_4$) and concentrated to dryness. To the free amine in DCM (400 mL) at 0° C. is added the compound 5C (isomer 2, 44.8 g, 161.5 mmol), EDC (31.0 g, 161.5 mmol) and 4-DMAP (2.0 g, 16.1 mmol). The reaction mixture is stirred at 0° C. for about 30 minutes and then stirred for another 5 hours at r.t. The mixture is then washed with saturated aqueous sodium bicarbonate (200 mL) and 10% aqueous sodium bisulfate (200 mL). The mixture is dried ($Na_2SO_4$) and concentrated to afford about 76.4 g (100%) of the ester. EIS-MS 471 [M−1].

Step B: To the ester from Step A (76.4 g, 161.5 mmol) in MeOH (760 mL) is added 1 N NaOH (242.0 mL, 242.0 mmol), and the mixture is heated at 50° C. for about 4 hours. The mixture is stirred for another 16 hours at r.t. After concentrating to dryness, the resulting residue is taken up in 500 mL of water and washed with diethyl ether (2×). The aqueous portion is acidified to pH 2 with 10% aqueous sodium bisulfate and extracted with EtOAc (4×200 mL). The combined organic extracts are dried ($MgSO_4$) and concentrated to dryness. The resulting solid is suspended in hexane and then filtered and dried to afford about 67.7 g (91%) of the final compound. EIS-MS 457 [M−1].

Preparation 4BC

Lithium; 2-[(2-tert-butoxycarbonyl-1,2,3,4-tetrahydro-isoquinolin-3-ylmethyl)-amino]-3-(4-chloro-phenyl)-propionate

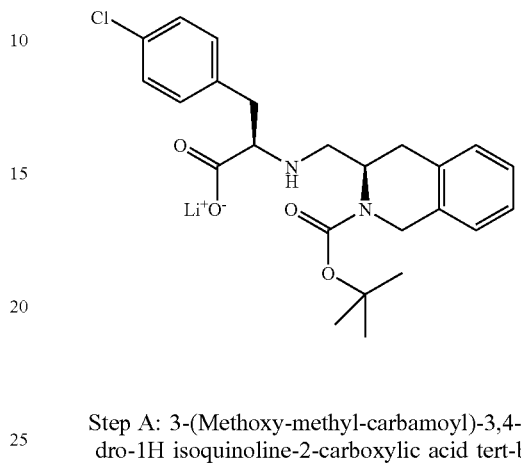

Step A: 3-(Methoxy-methyl-carbamoyl)-3,4-dihydro-1H isoquinoline-2-carboxylic acid tert-butyl ester To Boc-D-1,2,3,4-tetrahydroisoquinoline carboxylic acid (14.9 g, 53.7 mmol) in THF (500 mL) is added N,O-dimethylhydroxylamine hydrochloride (5.24 g, 53.7 mmol), EDC (11.3 g, 59.1 mmol), HOBT (7.98 g, 59.1 mmol) and DIPEA (9.83 mL, 56.4 mmol). The mixture is stirred for about 16 hours at r.t. under nitrogen and then concentrated to dryness. The resulting residue is taken up in EtOAc, washed with 1M HCl, saturated sodium bicarbonate and brine, and dried ($Na_2SO_4$). After concentrating to dryness, the resulting residue is purified by flash chromatography ($SiO_2$, eluting with 1:1 EtOAc/hexane) to give about 12.3 g (71%) of the ester. EIS-MS 321 [M+1]

Step B: 3-Formyl-3,4-dihydro-1H-isoquinoline-2-carboxylic acid tert-butyl ester

To a 0° C. solution of material from Step A (1.28 g, 4.00 mmol) in THF (30 mL) is slowly added 1.0 M LAH (in THF, 5.1 mmol, 5.1 mmol). The reaction mixture is stirred at 0° C. for another 15 minutes. To the mixture is slowly added 20 mL of 5% aqueous potassium hydrogensulfate, and the mixture is extracted with $Et_2O$ (2×). The combined organic portions are washed with 1M HCl, saturated sodium bicarbonate and brine. The mixture is dried ($Na_2SO_4$) and concentrated to dryness yielding about 0.78 g (75%). EIS-MS 262 [M+1]

Step C: 3-{[2-(4-Chloro-phenyl)-1-methoxycarbonyl-ethylamino]-methyl}-3,4-dihydro-1H-isoquinoline-2-carboxylic acid tert-butyl ester To a 0° C. solution of 4-Cl-D-Phe methyl ester (6.27 g, 25.1 mmol) and sodium acetate (8.23 g, 100.0 mmol) in 850 ml dry MeOH is added material from Step B (9.8 g, 37.6 mmol) in 50 ml MeOH. The mixture is stirred for about 15 minutes and then sodium cyanoborohydride (2.37 g, 37.6 mmol) is added. The cooling bath is removed, and the mixture is stirred for about 16 hours at r.t. The mixture is concentrated to dryness and the resulting residue is taken up in water and 1 mL of 1M HCl. The mixture is extracted with EtOAc and organics are washed with saturated sodium bicarbonate, brine, dried ($Na_2SO_4$), and concentrated to dryness. The resulting residue is purified by flash chromatography ($SiO_2$, eluting with 2:1 hexane/EtOAc) to afford about 8.62 g (75%). EIS-MS 459 [M+1]

Step D: To a 12° C. solution of material from Step C (1.11 g, 2.42 mmol) in dioxane (15 ml) is added a solution of lithium hydroxide (0.10 g, 2.42 mmol) in water (7.5 mL). The mixture is stirred for about 16 hours at r.t. and then concentrated to dryness to afford about 1.08 g (100%) of the final compound. EIS-MS 445 [M+1]

Preparation 5BC 3-(4-Chloro-phenyl)-2-[(1,1-dimethyl-1,2,3,4-tetrahydro-isoquinoline-3-carbonyl)-amino]-propionic acid methyl ester

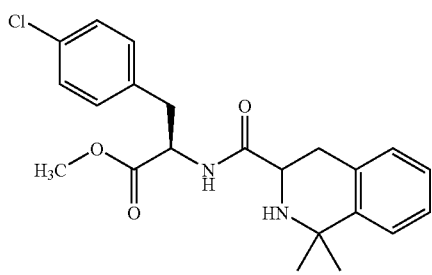

To 1,1-dimethyl tic (240 mg, 1.17 mmol) in $CH_2Cl_2$/DMF (1:1) is added 4-Cl-D-Phe methyl ester (322 mg, 1.28 mmol), HOBT (197 mg, 1.46 mmol), DIPEA (0.81 mL, 44.68 mmol) and EDC (280 mg, 1.46 mmol). The mixture is stirred at r.t. overnight. The mixture is diluted with EtOAc (100 mL) and the organics are washed with saturated aqueous $NaHCO_3$, brine, dried ($Na_2SO_4$), and concentrated to dryness. Purification and separation of the diastereomers is accomplished by flash chromatography (35 g $SiO_2$, linear gradient, 40 mL/min 10–50% EtOAc/hexane for 25 minutes and 50% EtOAC/hexane for 7 minutes) to afford about 117 mg of the final compound (25%). LRMS (ESI+): 401.1 (M+H).

Preparation 6BC 3-(4-Chloro-phenyl)-2-[(1,1-dimethyl-1,2,3,4-tetrahydro-isoquinoline-3-carbonyl)-amino]-propionic acid

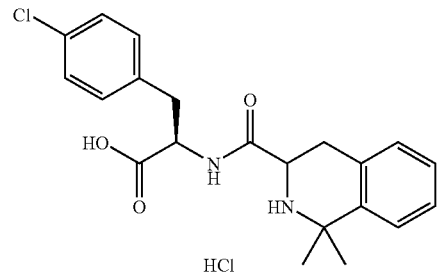

To the compound 5BC (5.95 g, 14.88 mmol) in a 1:1 mixture of THF/$H_2O$ (50 mL) is added lithium hydroxide hydrate (0.75 g, 17.87 mmol). The reaction is stirred at r.t. for about 18 hours. The mixture is then concentrated to dryness. The resulting residue is dissolved in water (50 mL) and adjusted to acidic with 1N HCl (25 mL) and then washed with $Et_2O$ (100 mL). The aqueous layer is evaporated to dryness to afford about 6.18 g (98%) of the final compound. EIS-MS 387 [M+1]

Preparation 7BC lithium; 2-[(2-tert-butoxycarbonyl-1,2,3,4-tetrahydro-isoquinolin-3-ylmethyl)-amino]-3-(4-chloro-phenyl)-propionate

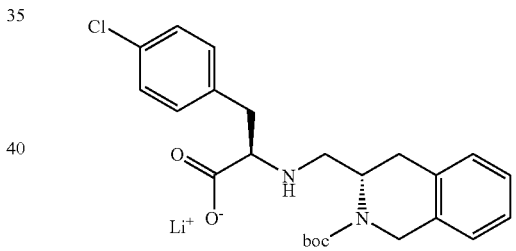

The above compound was Prepared in a manner similar to the preparation 4BC above except that Boc-L-1,2,3,4-tetrahydroisoquinoline carboxylic acid was used.

Preparation 8BC

Preparation of Lithium 2-[(2-tert-butoxycarbonyl-1,2,3,4-tetrahydro-isoquinolin-3-ylmethyl)-methyl-amino]-3-(4-chloro-phenyl)-propionate

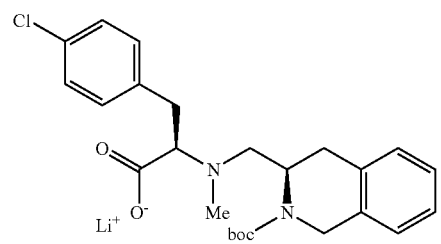

Step A: To a solution of 3-{[2-(4-Chloro-phenyl)-1-methoxycarbonyl-ethylamino]-methyl}-3,4-dihydro-1H-isoquinoline-2-carboxylic acid tert-butyl ester from preparation 3BC Step C (0.60 gm, 1.31 mmol) in anhydrous methanol, was added sodium acetate (0.54 gm, 6.54 mmol). The solution was brought to pH 5–6 with 3–4 drops of glacial acetic acid. Aqueous formaldehyde (37% by wt., 0.49 mL) was added. The solution was put under a nitrogen atmosphere and cooled to 0° C. After about 15 minutes, sodium cyanoborohydride (0.25 gm, 3.92 mmol) was added and rinsed into the reaction with anhydrous methanol (5 mL). The mixture was stirred at r.t. overnight, and then concentrated in vacuo and reconstituted in aqueous sodium bicarbonate and ethyl acetate. After separation of phases, the aqueous phase was extracted with ethyl acetate (2×), and all organics were combined, dried (magnesium sulfate), filtered, and concentrated to an opaque white oil (0.64 gm). Chromatography (0 to 20% ethyl acetate in hexane) gave about 0.6 g of methylated product as a clear oil (97%). MS (m/z, ES+): 473.2.

Step B: A solution of LiOH.H$_2$O (0.05 gm, 1.27 mmol) in distilled water (4 mL) was added to a solution of the material from Step A in 1,4-dioxane (8 mL), and the reaction was cooled slightly in an ice water bath. The mixture was stirred under a nitrogen atmosphere at r.t. overnight. An additional 1.5 eq. of LiOH.H$_2$O (0.08 gm) were added as an aqueous solution (4 mL), and the mixture was stirred at r.t. over the weekend. The mixture was concentrated, and then combined with THF and concentrated (3×) to help dry the material. The resulting foam was dried at r.t. overnight in a vacuum oven to give about 0.67 g of final compound as a white foam (114%). MS (m/z, ES+): 459.2.

Preparation 9BC lithium 2-[(2-tert-butoxycarbonyl-1,2,3,4-tetrahydro-isoquinolin-3-ylmethyl)-(2-methoxy-ethyl)-amino]-3-(4-chloro-phenyl)-propionate

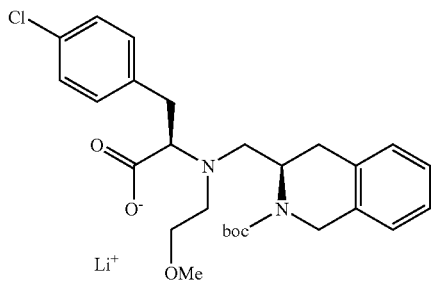

Step A: To a solution of methoxyacetaldehyde (0.15 gm, 2.03 mmol), 3-{[2-(4-Chloro-phenyl)-1-methoxycarbonyl-ethylamino]-methyl}-3,4-dihydro-1H-isoquinoline-2-carboxylic acid tert-butyl ester from preparation 3BC Step C (0.31 gm, 0.68 mmol) in acetonitrile was added sodium triacetoxyborohydride (0.72 gm, 3.38 mmol). After stirring overnight under a nitrogen atmosphere at r.t., additional acetaldehyde (0.25 gm) dissolved in acetonitrile and sodium triacetoxyborohydride (0.21 gm) was added, and the mixture was stirred for about 8.5 hours. The mixture was quenched at r.t. with 5N NaOH (5 mL). The aqueous phase was separated from the organic and extracted with ethyl acetate (4×). The combined organics were washed with a brine solution, and then dried, filtered and concentrated. Chromatography (gradient of ethyl acetate in hexane, 0 to 12%) gives about 0.23 g of 3-{[[2-(4-Chloro-phenyl)-1-methoxycarbonyl-ethyl]-(2-methoxy-ethyl)-amino]-methyl}-3,4-dihydro-1H-isoquinoline-2-carboxylic acid tert-butyl ester as a yellow oil (70%). MS (m/z, ES+): 517.2.

Step B: To a solution of the material from Step A in 1,4-dioxane was added a solution of lithium hydroxide monohydrate (0.05 gm, 1.11 mmol) in distilled water (2 mL). The mixture was stirred overnight at r.t. and then concentrated to a white residue. Addition of THF and concentration (3×) gives the lithium carboxylate as a foam. The foam was dried overnight under vacuum to afford about 0.25 g of crude solids (109%). MS (m/z, ES+): 503.3.

Preparation 10BC

1-{[1-Carboxy-2-(4-chloro-phenyl)-ethylcarbamoyl]-methyl}-1,3-dihydro-isoindole-2-carboxylic acid tert-butyl ester

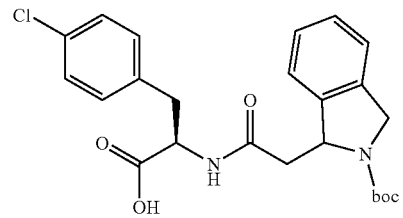

Step A: To a suspension of 4-Cl-D-Phe-OMe hydrochloride (40.4 g, 161.5 mmol) in DCM (250 mL) was added saturated aqueous sodium bicarbonate (250 mL), and the mixture was stirred at r.t. for about 1 hour. The organic portion was separated and the aqueous portion was extracted with DCM (2×). The combined organic portions were dried (Na$_2$SO$_4$) and concentrated to dryness. To the free amine, in DCM (400 mL) at 0° C., was added 1-Carboxymethyl-1,3-dihydro-isoindole-2-carboxylic acid tert-butyl ester from preparation 2C (isomer 2, 44.8 g, 161.5 mmol), EDC (31.0 g, 161.5 mmol) and 4-DMAP (2.0 g, 16.1 mmol). The mixture was stirred at 0° C. for about 30 minutes whereupon the cooling bath was removed and the mixture was stirred for another 5 hours at r.t. The mixture was then washed with saturated aqueous sodium bicarbonate (200 mL) and 10% aqueous sodium bisulfate (200 mL), and then dried (Na$_2$SO$_4$) and concentrated to dryness to afford about 76.4 g (100%) of the ester. EIS-MS 471 [M−1].

Step B: To the ester from Step A (76.4 g, 161.5 mmol) in MeOH (760 mL) was added 1 N NaOH (242.0 mL, 242.0 mmol), and the mixture was heated at 50° C. for 4 hours and then stirred for another 16 hours at r.t. After concentrating to dryness, the resulting residue was taken up in 500 mL of water and washed with diethyl ether (2×). The aqueous portion was acidified to pH 2 with 10% aqueous sodium bisulfate and extracted with EtOAc (4×200 mL). The combined organic extracts were dried (MgSO$_4$) and concentrated to dryness. The resulting solid was suspended in hexanes, filtered, and dried to afford about 67.7 g (91%) of the final compound. EIS-MS: 457 [M−1].

Preparation 11BC

1-{[1-Carboxy-2-(4-methoxy-phenyl)-ethylcarbamoyl]-methyl}-1,3-dihydro-isoindole-2-carboxylic acid tert-butyl ester

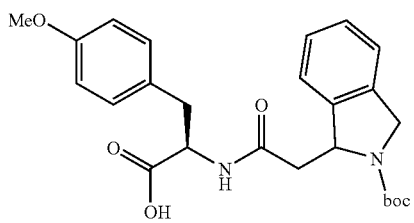

Step 1: To a solution of p-methoxy-D-Phe-OMe (1.72 g, 8.23 mmol) dissolved in THF (45 mL) and 1-carboxymethyl-1,3-dihydro-isoindole-2-carboxylic acid tert-butyl ester (2.51 g, 9.05 mmol) was added HOBT (1.22 g, 9.05 mmol), EDC (1.73 g, 9.05 mmol) and DIPEA (1.6 mL, 9.05 mmol). The reaction was stirred overnight at r.t. and then concentrated. The mixture was washed with 1M HCl, dilute NaHCO₃ and brine, and then dried with sodium sulfate. The mixture was chromatographed on silica gel eluting with 3% 2M NH₃ in MeOH/CH₂Cl₂ giving about 2.58 g as white solids. Mass MH⁺ 469

Step 2: The white solid from Step 1 (2.58 g, 5.5 mmol) was dissolved in dioxane (37 mL) and lithium hydroxide hydrate (0.35 g, 8.3 mmol) dissolved in H₂O (19 mL) was added. The mixture was stirred for about 2.5 hours at r.t. and then concentrated. Ethyl acetate was added and the mixture was treated with 1M HCl, which was then washed with brine and concentrated to afford about 2.56 g of the final free acid. LRMS (ESI+): 455 (M+1)

Preparation 12BC

1-[1-Carboxy-2-(4-chloro-phenyl)-ethylcarbamoyl]-1,3-dihydro-isoindole-2-carboxylic acid tert-butyl ester

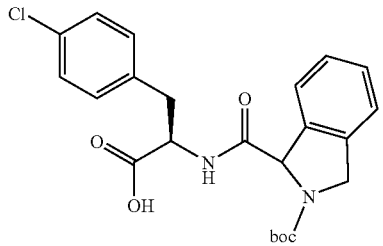

Step 1: About 2.0 g (7.60 mmol) of (R,S)-Boc-1,3-dihydro-2H isoindole carboxylic acid was dissolved in 100 ml THF and about 2.28 g (9.12 mmol) of 4-Cl-D-phe-methylester HCl, 1.25 g (9.12 mmol) of HOBT, 1.75 g (9.12 mmol) of EDC, and 1.6 ml (9.12 mmol) of DIEA were added. The mixture was stirred overnight at r.t., concentrated to dryness, washed with 1M HCl, dilute NaHCO₃ and brine, and then dried over sodium sulfate. The material was chromatographed on silica gel by eluting with ethyl acetate/hexane 1:2 to give about 1.05 g of isomer 1 and about 0.82 g of isomer 2, and about 1.61 g mixture of isomers 1 and 2. Mass MH⁺ 459

Step 2: About 0.82 g (1.79 mmol) of the isomer 2 obtained in Step 1 was dissolved in 11 ml of dioxane and 0.11 g (2.68 mmole) of LiOH-hydrate in 5.5 ml of H₂O was added. The mixture was stirred for about 4 hours at r.t. and then concentrated to dryness. Ethyl acetate was added, and the solution was washed with 1M HCl and brine, and then concentrated to dryness affording about 0.75 g of the free acid. Mass: 445 (MH⁺).

EXAMPLES

Example 1

3-(4-chloro-phenyl)-2-[(1,1-dimethyl-1,2,3,4-tetrahydroisoquinoline-3-carbonyl)-amino]-propionic acid

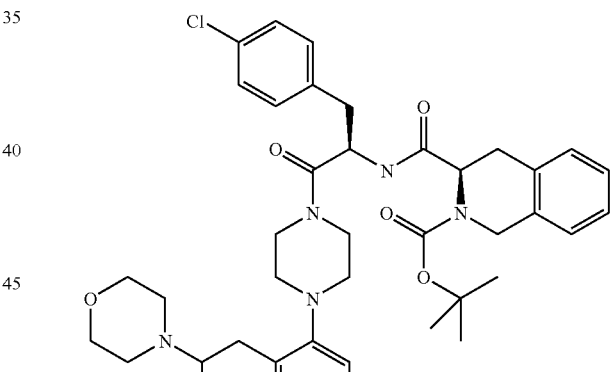

To compound 4A (0.441 g, 0.96 mmol), in DCM (8 mL) and DMF (2 mL), is added compound 1BC (0.289 g, 0.96 mmol), DIPEA (1.6 mL, 9.60 mmol), and HATU (0.365 g, 0.96 mmol). The mixture is stirred at r.t. overnight and then concentrated to dryness. The resulting residue is taken up in EtOAc (50 mL), and the organics are washed with saturated NaHCO₃, H₂O and brine, and then concentrated to dryness. The desired product is purified by flash chromatography (SiO₂, eluting with EtOAc-TEA-MeOH, 98:1:1 to 90:5:5) to afford about 0.60 g of the final compound (84%). EIS-MS 742.3 [M+1]

Example 2

1,2,3,4-Tetrahydro-isoquinoline-3-carboxylic acid {1-(4-chloro-benzyl)-2-[4-(7-morpholin-4-yl-5,6,7,8-tetrahydro-naphthalen-1-yl)-piperazin-1-yl]-2-oxo-ethyl}-amide

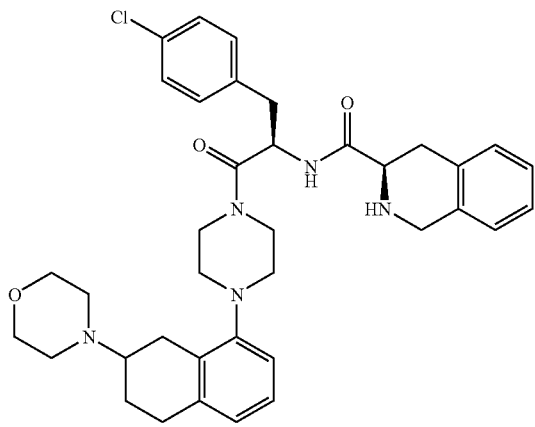

To compound of Example 1 (0.596 g, 0.803 mmol), in DCM (5 mL), is added TFA (5 mL) and the mixture is stirred at room temperature for about 5 minutes. After concentrating to dryness, the resulting residue is triturated with Et₂O, and the resulting solid is collected by filtration and dried to afford about 0.52 g of the final compound (91%). EIS-MS 642.2 [M+1]

Example 3

1,2,3,4-Tetrahydro-isoquinoline-3-carboxylic acid {1-(4-chloro-benzyl)-2-[4-(7-dimethylamino-5,6,7,8-tetrahydro-naphthalen-1-yl)-piperazin-1-yl]-2-oxo-ethyl}-amide; trifluoroacetate

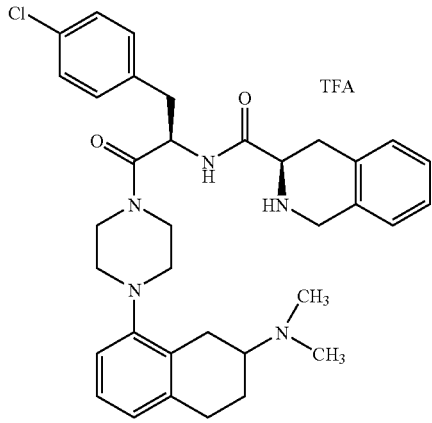

Step 1: To the A domain compound described in Preparation 1A (917 mg, 3.75 mmol) is added N-Boc-D-Tic-4-Cl-D-Phe-OH (1.7 g, 3.75 mmol), HATU (1.43 g, 3.75 mmol), DIPEA (1.3 mL, 7.5 mmol), CH₂Cl₂ (10 mL) and DMF (3 mL). The mixture is stirred at r.t. for 12 hours and then diluted with EtOAc (15 fold). The organics are washed with saturated NaHCO₃, H₂O and brine, and then concentrated to dryness. The resulting residue is purified by flash chromatography (Silica gel 60, eluting with EtOAc) and then used in Step 2 below (917 mg, 35%). Ion spray MS: 770.2 [M+].

Step 2: To the compound of Step 1 (917 mg, 1.30 mmol) in CH₂Cl₂ (10 mL) is added TFA (8 mL), and the mixture is stirred at r.t. for about 30 minutes. After concentrating to dryness, the resulting residue is triturated with Et₂O, and the TFA salt is collected via filtration and dried under vacuum to afford about 920 mg of the final compound (85%). Ion spray MS: 600.2 [M+].

Examples 4–18

The compounds of examples 4–18 are prepared from using appropriate A domain and the compound 1BC (Preparation 1BC) by following a substantially similar procedure as described in Examples 1 and 2.

| No | Z | EIS-MS [M + 1] |
|---|---|---|
| 4 | diethylamino-tetrahydronaphthalenyl | 625.2 |
| 5 | dipropylamino-tetrahydronaphthalenyl | 656.2 |
| 6 | pyrrolidinyl-tetrahydronaphthalenyl | 626.2 |
| 7 | N-methyl-N-ethylamino-tetrahydronaphthalenyl | 614.2 |

-continued

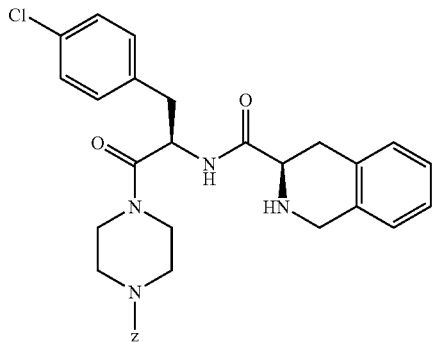

| No | Z | EIS-MS [M + 1] |
|----|---|----------------|
| 8 | (N-isopropyl, N-methyl 8-methyl-tetrahydronaphthalen-2-yl amine) | 628.2 |
| 9 | (N-isobutyl, N-methyl 8-methyl-tetrahydronaphthalen-2-yl amine) | 642.3 |
| 10 | (N-methyl 8-methyl-tetrahydronaphthalen-2-yl amine) | 586.1 |
| 11 | (N-methyl, N-methanesulfonyl 8-methyl-tetrahydronaphthalen-2-yl amine) | 664.2 |
| 12 | (N-acetyl 8-methyl-tetrahydronaphthalen-2-yl amine) | 614.1 |
| 13 | (8-methyl-tetrahydronaphthalen-2-yl amine) | 572.2 |
| 14 | (8-methyl-tetrahydronaphthalen-2-yl acetate) | 615.2 |
| 15 | (8-methyl-tetrahydronaphthalen-2-yl carbamate) | 615.2 |

-continued

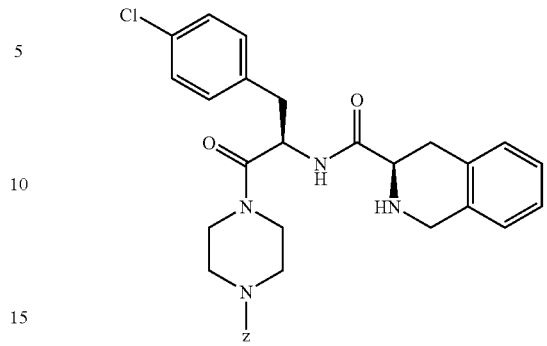

| No | Z | EIS-MS [M + 1] |
|----|---|----------------|
| 16 | (methyl carbamate of 8-methyl-tetrahydronaphthalen-2-yl amine) | 630.2 |
| 17 | (N,N-diethyl 8-methyl-tetrahydronaphthalen-2-yl amine) | 629.1 |
| 18 | (N,N-diethyl 8-methyl-tetrahydronaphthalen-2-yl amine) | 629.1 |

Example 19

3-{1-(4-chloro-phenyl)-2-[4-(7-morpholin-4-yl-5,6,7,8-tetrahydro-naphthalen-1-yl)-piperidin-1-yl]-2-oxo-ethylcarbamoyl}-3,4-dihydro-1H-isoquinolin-2-carboxylic acid tert-butyl ester

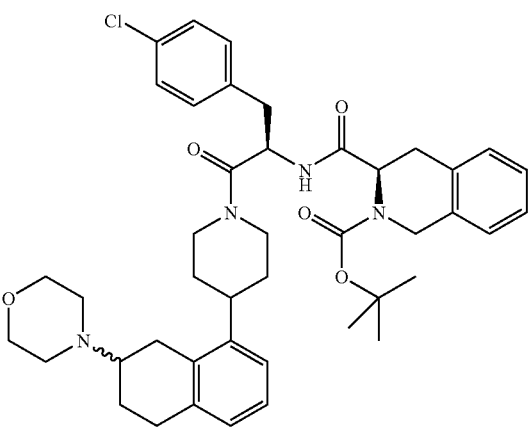

To the compound 34A (0.351 g, 0.779 mmol), in DCM (8 mL) and DMF (2 mL), is added compound 1BC (0.234 g, 0.779 mmol), DIPEA (1.36 mL, 7.79 mmol), and HATU (0.296 g, 0.779 mmol). The mixture is stirred at r.t. overnight and then concentrated to dryness. The resulting residue is taken up in EtOAc (50 mL) and the organics washed with saturated NaHCO₃, H₂O, brine, and concentrated to dryness. The desired product is purified by flash chromatography (SiO₂, eluting with 100% EtOAc to EtOAc-TEA-MeOH, 90:5:5) to afford about 0.46 g of the final product (79%). EIS-MS 741.3 [M+1]

Example 20

1,2,3,4-Tetrahydro-isoquinoline-3-carboxylic acid {1-(4-chloro-benzyl)-2-[4-(7-morpholin-4-yl-5,6,7,8-tetrahydro-naphthalen-1-yl)-piperidin-1-yl]-2-oxo-ethyl}-amide To compound prepared in Example 19 (0.42 g, 0.567 mmol), in DCM (3 mL), is added TFA (3 mL) and the mixture is stirred at room temperature for about 45 minutes. After concentrating to dryness, the resulting residue is triturated with Et₂O, and the resulting solid is collected by filtration and dried to afford about 0.47 g of the final product (94%). EIS-MS 641.2 [M+1]

Examples 21–29

The compounds of examples 21–29 are prepared from the appropriate A domain and the compound 1BC by following a substantially similar procedure as described in Examples 19 and 20.

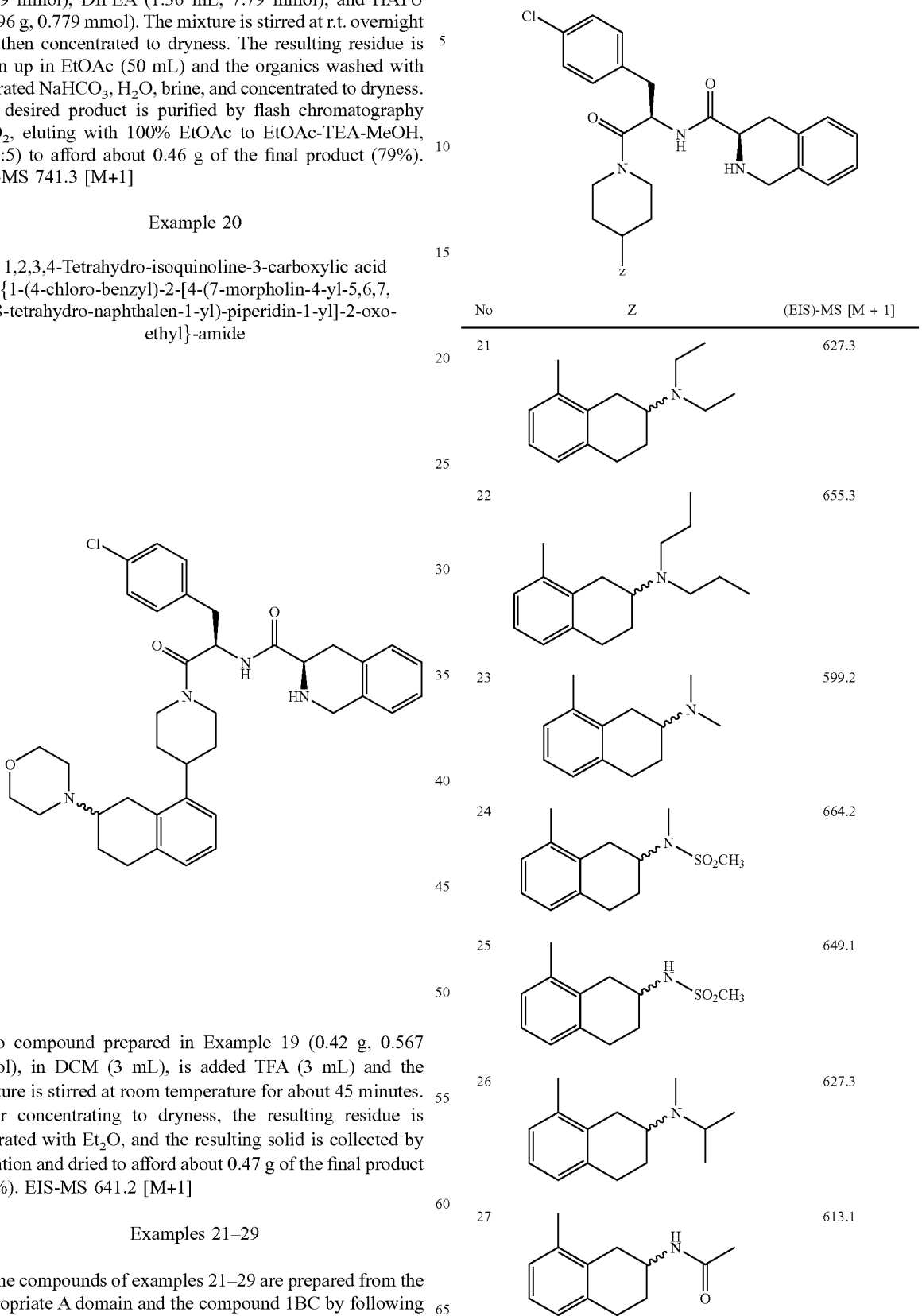

| No | Z | (EIS)-MS [M + 1] |
|---|---|---|
| 21 | | 627.3 |
| 22 | | 655.3 |
| 23 | | 599.2 |
| 24 | | 664.2 |
| 25 | | 649.1 |
| 26 | | 627.3 |
| 27 | | 613.1 |

| | | |
|---|---|---|
| 28 | 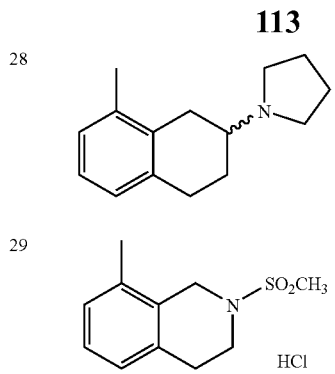 | 625.2 |
| 29 | 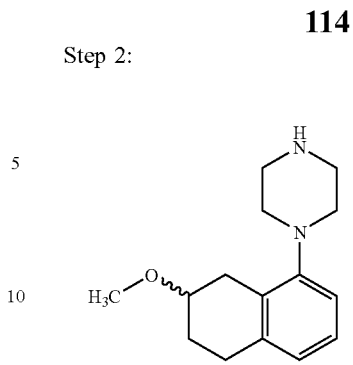 | 635.1 |

Example 30

1,2,3,4,-tetrahtdro-isoqunoline-3-carboxylic acid{1-(4-chlorobenzyl)-2-[4-(7-methoxy-5,6,7,8-tetrahydro-naphthalen-1yl)-piperazin-1-yl]-2-oxo-ethyl}amide

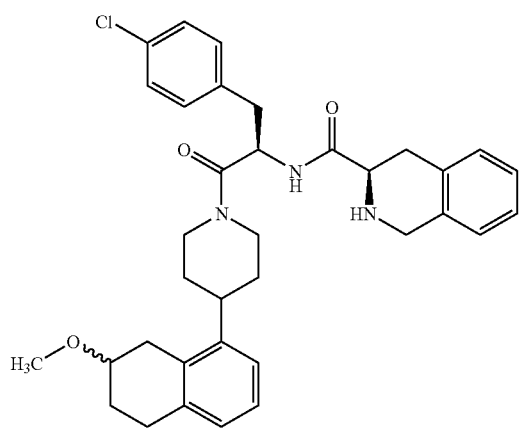

Step 1:

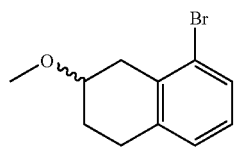

To 8-Bromo-2-hydroxytetralin (1.07 g, 4.71 mmol), prepared from 8-bromo-2-tetralone by essentially following the procedure outlined in *J. Org. Chem.*, 56(19): 5564–5566, 1991, in THF (5 mL), is added NaH (60% dispersion in oil, 330 mg, 8.24 mmol) and the mixture is stirred at r.t. for about 30 minutes. Iodomethane (367 microliters, 5.89 mmol) was then added and after about an hour the mixture is quenched by the cautious addition of H$_2$O (10 mL) and the desired product is extracted into EtOAc (50 mL). The organic extracts are concentrated to dryness and the desired methyl ether is purified by flash chromatography (SiO$_2$, eluting with toluene) to afford about 0.94 g of the final product (83%). EIS-MS 242.1 [M+1]

Step 2:

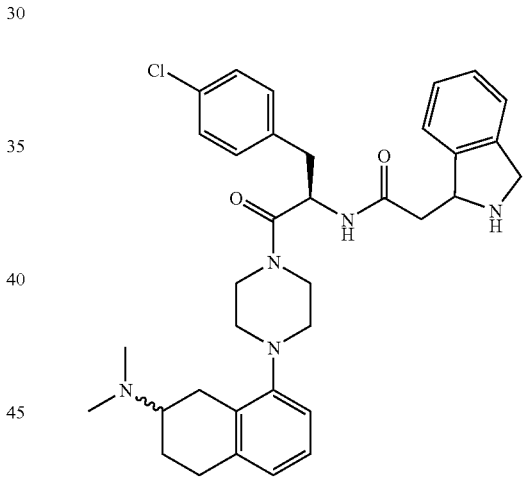

The A domain compound is prepared from the compound of Step 1 and N-Boc-piperazine by following substantially similar procedure as described in Preparation 3A and 4A. EIS-MS 247.2 [M+1]

The final compound of Example 31 is prepared by coupling the compound of step 2 and the compound 1BC by following substantially similar procedure as described in Examples 19 and 20. EIS-MS 587 [M+1]

Example 31

N-{1-(4-chloro-benzyl)-2-[4-(7-dimethylamino-5,6,7,8-tetrahydro-naphthalen-1-yl)-piperazin-1-yl]-2-oxo-ethyl}-2-(2,3-dihydro-1H-isoindol-1-yl)-acetamide

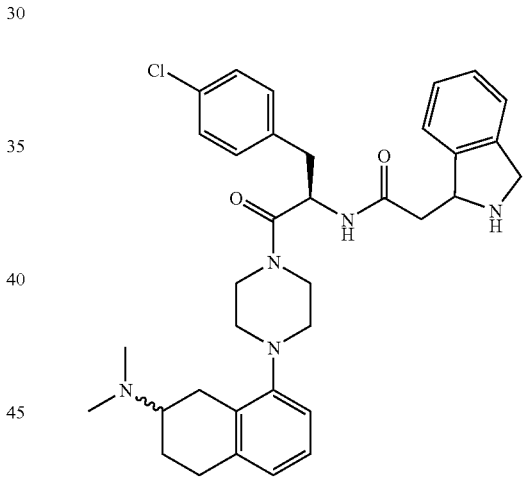

Step 1:

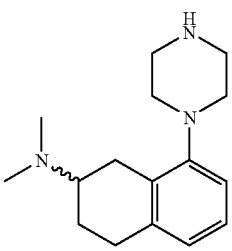

The Boc-protected title compound is prepared from 2-dimethylamino-8-bromo-1,2,3,4-tetrahydronaphthalene (European Patent Application 91–304047, 1.0 g, 3.93 mmol) and commercially available 1-Boc-piperazine (0.805 g, 4.32 mmol) by following the conditions outlined in *J. Am. Chem.*

Soc., 118:7215–7216, 1996. The desired product is purified by flash chromatography (SiO₂, eluting with 98:1:1, EtOAc-TEA-MeOH) to afford about 1.35 g (95%). EIS-MS 360.2 [M+1] To the Boc-protected compound (1.35 g, 3.75 mmol) is added TFA (5 mL) and DCM (5 mL) and the resulting mixture is stirred at r.t. for about 30 minutes. After concentrating to dryness the resulting residue is taken up in 1N NaOH and the desired amine is extracted into EtOAc (100 mL). The organics are washed with H₂O, brine, and re-concentrated to afford about 970 mg (quantitative). EIS-MS 260.1 [M+1]

Step 2:

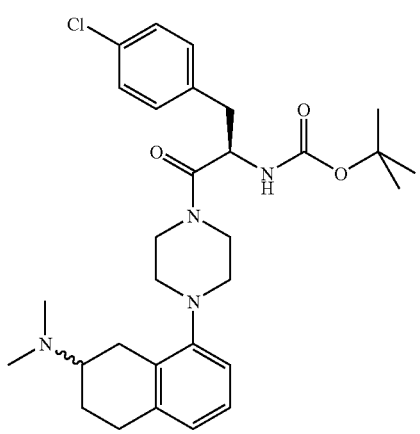

To the compound of Step 1 (0.68 g, 2.62 mmol) is added N-Boc-4-Cl-D-Phe (0.785 g, 2.62 mmol), EDC (0.553 g, 2.88 mmol), 4-DMAP (catalytic), DCM (4 mL), and DMF (1 mL). The mixture is stirred at r.t. for about one hour and then diluted with EtOAc (50 mL). The organics are washed with saturated NaHCO₃, H₂O, brine and concentrated to dryness. The resulting residue is purified by flash chromatography (SiO₂, eluting with EtOAc-TEA-MeOH, 90:5:5). EIS-MS 541.2 [M+1]

Step 3:

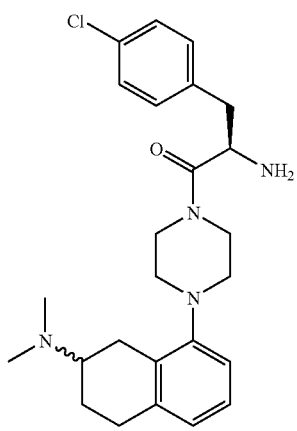

To the compound of Step 2 (1.41 g, 2.62 mmol), in DCM (5 mL), is added TFA (5 mL) and the mixture is stirred at r.t. for about 45 minutes. After concentrating to dryness, the resulting residue is taken up with 1 N NaOH and the desired "free" amine is extracted into EtOAc (100 mL). The organic extracts are concentrated to dryness to afford about 1.1 g (96%). EIS-MS 441.2 [M+1]

Step 4:

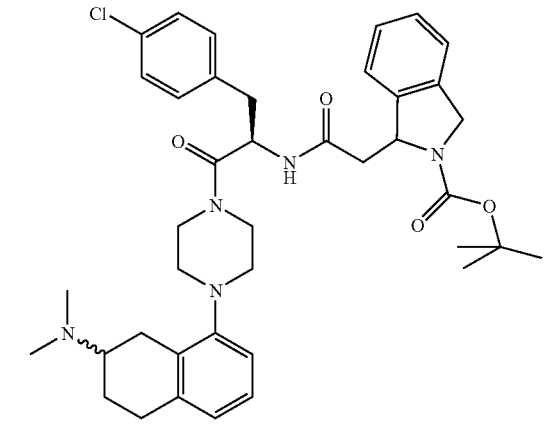

To the compound of Step 3 (0.279 g, 0.632 mmol) is added compound 5C (isomer 2, 0.175 g, 0.632 mmol), EDC (0.133 g, 0.695 mmol), 4-DMAP (catalytic), and DCM (6 mL). The mixture is stirred at r.t. for about an hour and then diluted with EtOAc (50 mL). The organics are washed with saturated NaHCO₃, H₂O, brine, and concentrated to dryness. The resulting residue is purified by flash chromatography (SiO₂, eluting with EtOAc-TEA-MeOH, 90:5:5) to afford 430 mg (97%). EIS-MS 700.2 [M+1]

Step 5: To the compound of Step 4 (0.430 g, 0.614 mmol), in DCM (5 mL), is added TFA (5 mL) and the mixture is stirred at r.t. for about 45 minutes. After concentrating to dryness, the resulting residue is triturated with Et₂O, and the resulting solid is collected by filtration and dried to afford about 0.325 g of the final product (74%). EIS-MS 600.2 [M+1]

Example 32

N-{1-(4-Chloro-benzyl)-2-oxo-2-[4-(7-pyrrolidin-1-yl-5,6,7,8-tetrahydro-naphthalen-1-yl)-piperazin-1-yl]-ethyl}-2-(2,3-dihydro-1H-isoindol-1-yl)-acetamide

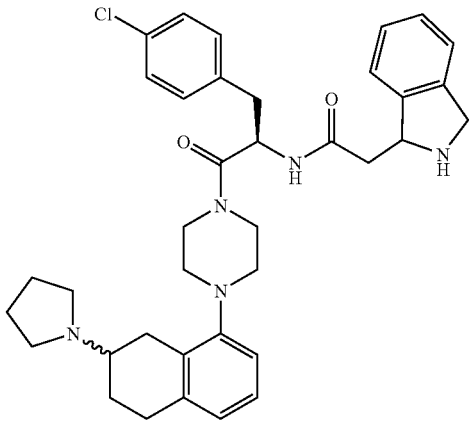

Example 32 is prepared from the compound 8A by following a substantially similar procedure as described in Example 31. EIS-MS 624.4 [M−1].

Example 33

3-(4-Chloro-phenyl)-1-[4-(7-dimethylamino-5,6,7,8-tetrahydro-naphthalen-1-yl)-piperazin-1-yl]-2-[(1,2,3,4-tetrahydro-isoquinolin-3-ylmethyl)-amino]-propan-1-one

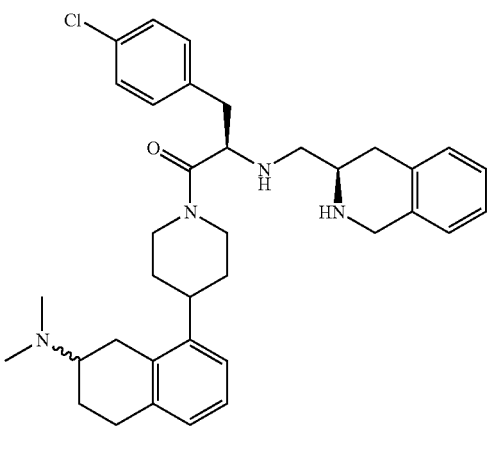

Step 1:

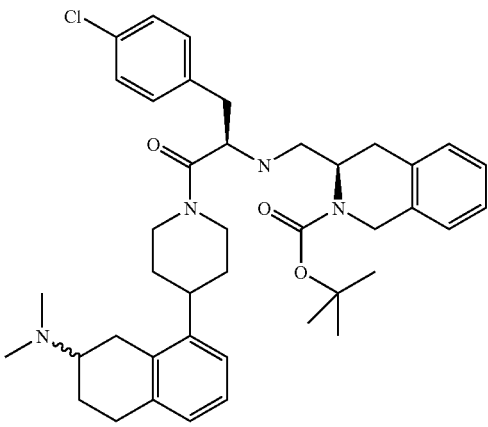

To the compound obtained in Step 1 of Example 31 (0.150 g, 0.685 mmol), in DCM, is added compound 4BC (0.307 g, 0.685 mmol), EDC (0.131 g, 0.685 mmol) and HOBT (0.106 g, 0.685 mmol). The mixture is stirred at r.t. for about 4 hours and then diluted with EtOAc (50 mL). The organics are washed with saturated NaHCO$_3$, H$_2$O, brine, and concentrated to dryness. The resulting residue is purified by flash chromatography (SiO$_2$, eluting with 5% 2.0 M ammonia in MeOH-DCM) to afford about 210 mg (45%). EIS-MS 686 [M+1]

Step 2: To the compound of Step 1 (0.20 g, 0.29 mmol), in CH$_2$Cl$_2$ (5 mL), is added TFA (5 mL) and the mixture is stirred at r.t. for about 45 minutes. After concentrating to dryness, the resulting residue is triturated with Et$_2$O, and the resulting solid is collected by filtration and dried to afford about 0.26 g of the final product (97%). EIS-MS 586.3 [M+1]

Examples 34–35 are prepared from the compound 30A and the appropriate B-C domain by following the substantially similar procedures described in Examples 1 and 2.

Examples 34–35

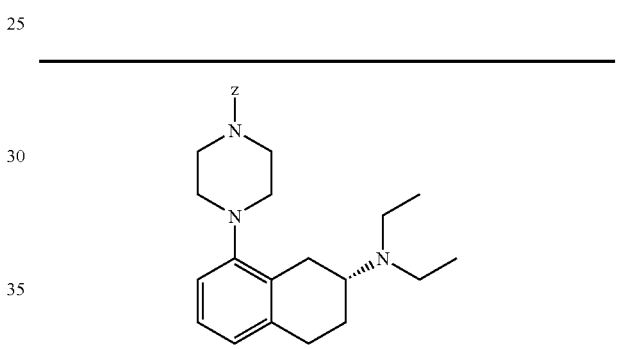

| No | Z | EIS-MS [M+1] | BC Domain |
|---|---|---|---|
| 34 | Cl-C₆H₄-CH₂-CH(C(=O)-)-NH-C(=O)-[tetrahydroisoquinoline-gem-dimethyl] Isomer 1 | 656.3 | 6BC Isomer 1 |
| 35 | Cl-C₆H₄-CH₂-CH(C(=O)-)-NH-C(=O)-[tetrahydroisoquinoline-gem-dimethyl] Isomer 2 | 656.3 | 6BC Isomer 2 |

Examples 36–37

Examples 36 and 37 are prepared from the amine compound,

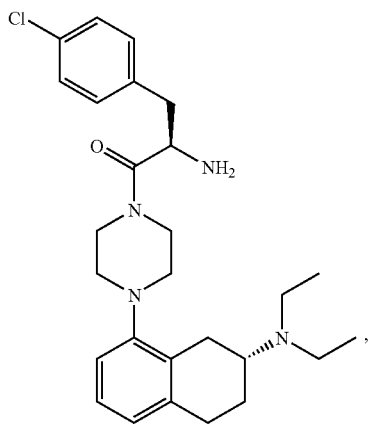

which is prepared from the compound 30A and 4-Cl-D-Phe by following a substantially similar procedure as described in Example 31, Steps 2 and 3 (62%). EIS-MS 569.1 [M+1]

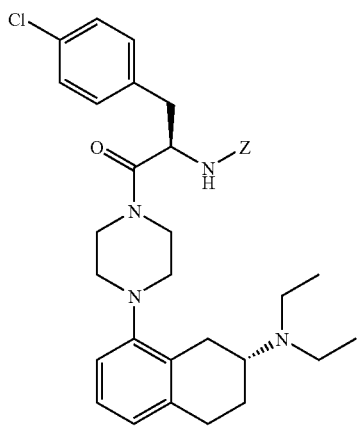

and the appropriate B-C domain by following a substantially similar procedure as described in Example 31, Steps 4 and 5.

| No | Z | EIS-MS [M + 1] | C Domain |
|---|---|---|---|
| 36 | 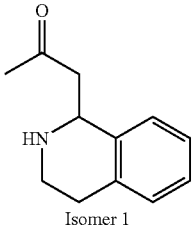<br>Isomer 1 | 642.1 | 6C Isomer 1 |
| 37 | 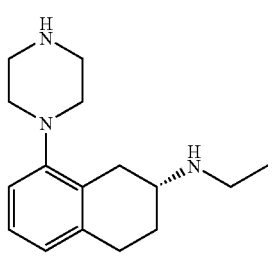<br>Isomer 2 | 642.1 | 6C Isomer 2 |

Example 38

1,2,3,4,-tetrahtdro-isoqunoline-3-carboxylic acid{1-(4-chlorobenzyl)-2-[4-(7-ethylamino-5,6,7,8-tetrahydro-naphthalen-1yl)-piperazin-1-yl]-2-oxo-ethyl}amide

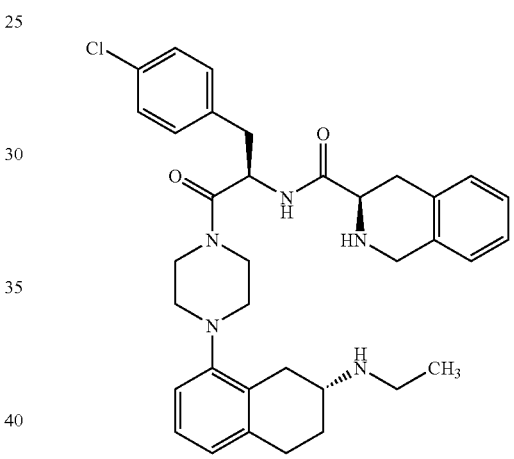

Step 1:

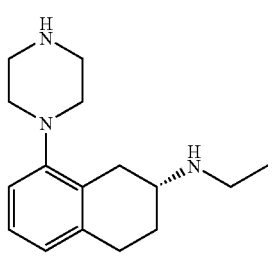

To the compound 26A (4.26 g, 12.85 mmol), in DMF (30 mL), is added ethyl bromide (2.89 mL, 38.55 mmol). The mixture is stirred at r.t. for about 48 hours, and an additional equivalent of ethyl bromide is added. The mixture is stirred for another 24 hours. The potassium carbonate is removed by filtration and washed with EtOAc. The filtrate is washed with $H_2O$, and the organics are dried over anhydrous $Na_2SO_4$ and concentrated to dryness. The resulting residue is purified by flash chromatography ($SiO_2$, eluting with EtOAc-TEA-MeOH, 98:1:1) to afford about 2.3 g (46%) diethyl amine and about 0.183 g (4%) mono-ethyl amine.

Step 2: The mono-ethyl amine is taken up in DCM (5 mL) and TFA (5 mL) is added. The mixture is stirred at r.t. for about 45 minutes. After concentrating to dryness, the resulting residue is taken up with 1N NaOH and the desired "free" amine is extracted into EtOAc (50 mL). The organic extracts are concentrated to dryness.

Step 3: The final compound is prepared by coupling the compound obtained above and the compound 1BC by following a substantially similar procedure as described in Examples 1 and 2 to afford about 181 mg (53%). EIS-MS 600.1 [M+H].

Example 39

1,2,3,4,-tetrahtdro-isoquinoline-3-carboxylic acid{1-(4-chlorobenzyl)-2-[4-(2-ethyl-1,2,3,4-tetrahydro-isoquinolin-8-yl)-piperazin-1-yl]-2-oxo-ethyl}amide

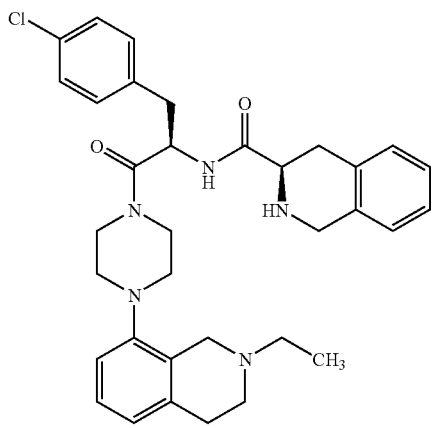

To compound 48A (226 mg, 0.92 mmol) and the compound 1BC (423 mg, 0.92 mmol), in DCM (10 mL), are added HATU (350 mg, 0.92 mmol) and DIPEA (0.323 mL, 1.84 mmol). The reaction is stirred at r.t. for about 12 hours and then concentrated to dryness. The resulting residue is purified by flash chromatography on silica gel. The coupled product is dissolved in a 1:1 mixture of DCM and TFA (10 mL) and stirred at r.t. for about 2 hours. After concentrating to dryness, the resulting residue is subjected to SCX ion exchange chromatography followed by flash chromatography on silica gel. The resultant foam is dissolved in DCM (10 mL) and 2.0 M HCl in diethyl ether added (5 mL). The slurry is concentrated to dryness, and the resultant solid dried under vacuum for 12 hours to give afford about 260 mg of the final compound (43%). EIS-MS 586.3 [M+1]

Example 40

1,2,3,4,-tetrahtdro-isoqunoline-3-carboxylic acid {1-(4-chloro-benzyl)-2-[4-{1H-indol-7-yl]-piperazin-1-yl]-2-oxo-ethyl}-amide

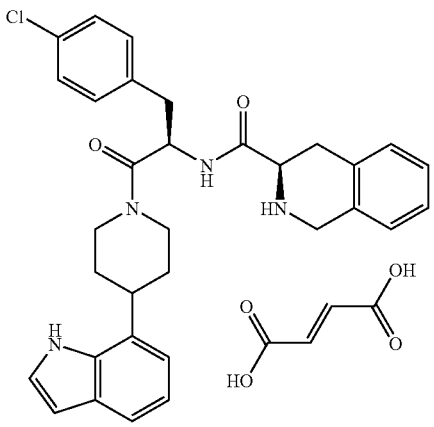

N-Boc-D-Tic-4-Cl-D-Phe-OH (100 mg, 0.22 mmol), the A domain compound of Preparation 69A (45 mg, 0.22 mmol) and HATU (84 mg, 0.22 mmol) are dissolved in 1 mL of 10% DMF in DCM followed by the addition of DIPEA (77 microliters, 0.44 mmol). The mixture is stirred under $N_2$ at r.t. for about 2 hours and then concentrated under vacuum. The residue is taken up in DCM (2 mL) and TFA is (2 mL) added. The mixture is stirred for about 2 hours and then concentrated to an oily solid. The mixture is "free-based" via SCX resin column and then chromatographed on silica gel. Product containing fractions are combined to give "free-based" material (46 mg). Fumaric acid (about 1 eq.) in methanol (10 mL) is added and the mixture is concentrated, triturated in ether, filtered and dried to give about 23 mg (16%) of the final product as the fumarate salt. EIS-MS: Found 542.3 M+1.

Examples 41–64

Examples 41–64 are prepared from the appropriate A domains and the compound 1BC by following a substantially similar procedure as described in Example 30.

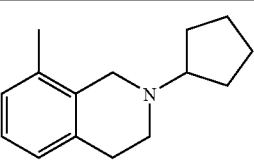

| No | Z | EIS-MS [M + 1] |
|---|---|---|
| 41 | | 626.3 |

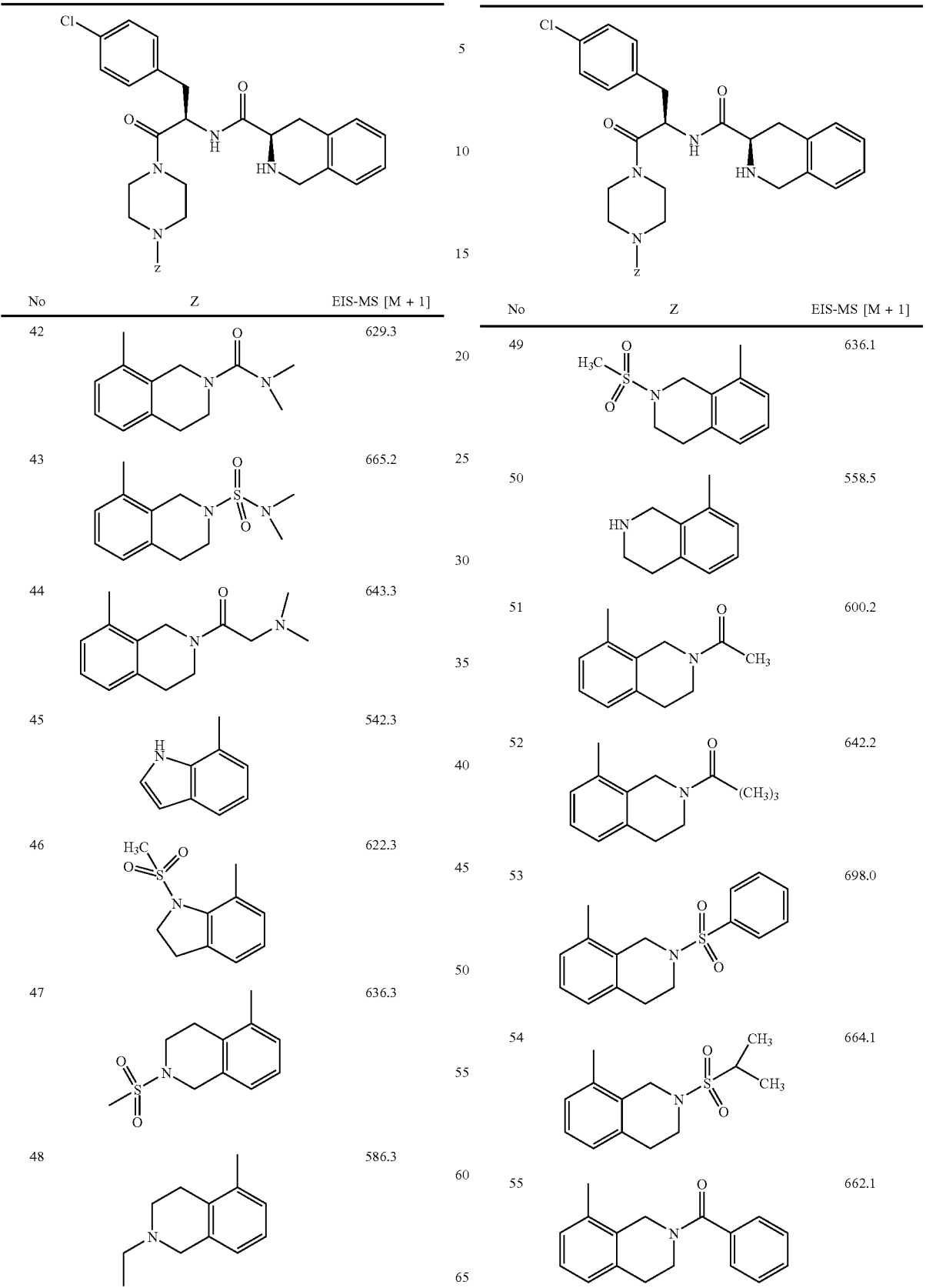

-continued

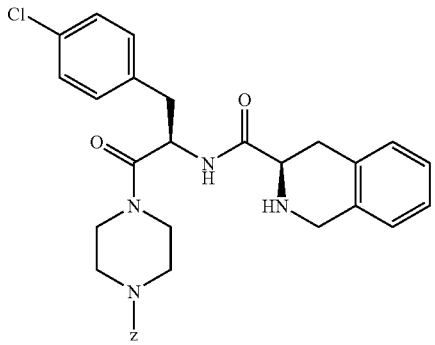

| No | Z | EIS-MS [M + 1] |
|---|---|---|
| 56 | 8-methyl-1,2,3,4-tetrahydroisoquinoline-2-carboxamide | 601.2 |
| 57 | methyl 8-methyl-1,2,3,4-tetrahydroisoquinoline-2-carboxylate | 616.3 |
| 58 | 8-methyl-1,2,3,4-tetrahydroquinoline | 558.3 |
| 59 | 1-acetyl-8-methyl-1,2,3,4-tetrahydroquinoline | 600.2 |
| 60 | 7-methylindoline | 544.3 |
| 61 | 1-methanesulfonyl-8-methyl-1,2,3,4-tetrahydroquinoline | 636.1 |
| 62 | 5-methyl-1,2,3,4-tetrahydroquinoline | 558.3 |

-continued

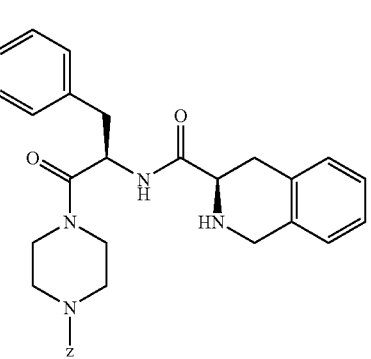

| No | Z | EIS-MS [M + 1] |
|---|---|---|
| 63 | 4-methyl-1H-indole | 542.3 |
| 64 | 8-methyl-2-methyl-1,2,3,4-tetrahydroisoquinoline | 572.1 |

Examples 65–68

Examples 65–68 are prepared from the appropriate A domains and the compound 1BC by following a substantially similar procedure as described in Example 39.

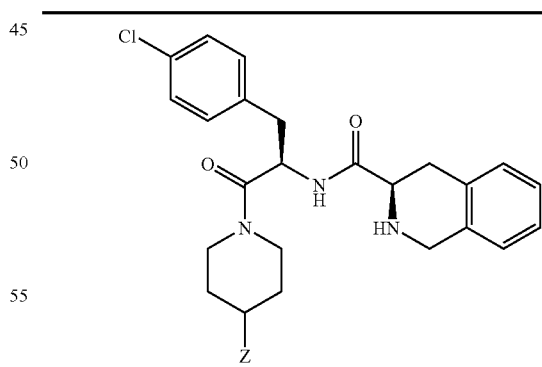

| No | Z | EIS-MS [M + 1] |
|---|---|---|
| 65 |  | 599.1 |

-continued

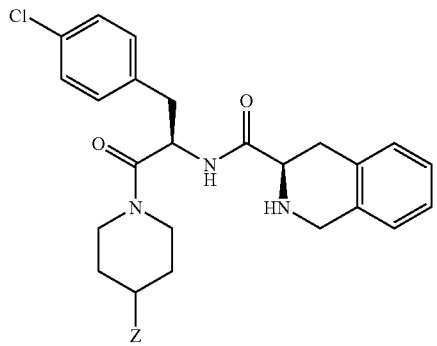

| No | Z | EIS-MS [M + 1] |
|---|---|---|
| 66 | ![structure with 8-methyl-N-ethyl tetrahydroisoquinoline] | 585.2 |
| 67 | ![structure with 8-methyl-N-methyl tetrahydroisoquinoline] | 571.0 |
| 68 | ![structure with 8-methyl-N-methylsulfonyl tetrahydroisoquinoline] | 635.2 |

Preparation of Novel C-Domain Pieces

Heck Coupling:

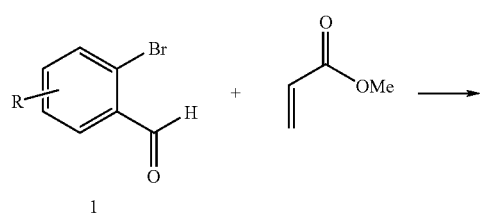

1a R = H
1b R = 5-OMe
1c R = 4,5-OMe
1d R = 5-NO$_2$

-continued

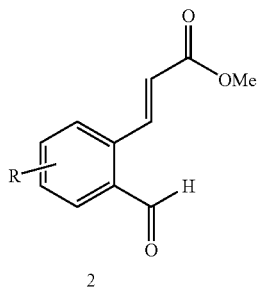

2a R = H
2b R = 5-OMe
2c R = 4,5-OMe
2d R = 5-NO$_2$

Preparation PP1

Synthesis of Compound (2a) by a Heck Coupling of 2-bromobenzaldehyde (1a) with methyl acrylate (Pd(OAc)$_2$/PPh$_3$ as the catalyst): A mixture of 2-bromobenzaldehye (1a) (24.5 g, 132 mmol), methyl acrylate (17.9 mL, 199 mmol), Pd(OAc)$_2$ (590 mg, 2.65 mmol, 2 mol %), PPh$_3$ (1.39 g, 5.30 mmol, 4 mol %) and Et$_3$N (46 mL, 331 mmol) was stirred at 80° C. for 15 h. Large amount of yellow solid was formed after the reaction was done. The mixture was cooled to r.t., concentrated, and mixed with H$_2$O (200 mL). The organic solid was collected by filtration, and then applied to a plug of silica gel (25 g) (EtOAc/hexane 1:1) to give a dark yellow solid. The solid was purified by crystallization (100 mL EtOAc bottom layer, 120 mL hexane top layer) to provide 17.57 g (70%) (100% pure by NMR) of the first crop and 5.23 g (21%) (95% by NMR) of the second crop of 2a.

Preparation PP2

Synthesis of Compound (2a) by a Heck Coupling of 2-bromobenzaldehyde (1a) with Methyl Acrylate (R=H) (Pd(OAc)$_2$/P(O-Tolyl)$_3$ as the catalyst): The compound 1a (9.998 g, 54.04 mmol) was dissolved in toluene (20 mL) at r.t. Methylacrylate (5.996 g, 69.65 mmol, 1.29 eq.), NEt$_3$ (15 mL), Pd(OAc)$_2$ and P(O-Tolyl)$_3$ were successively added and the mixture was stirred under reflux. After 2 hours, the reaction mixture was allowed to cool to r.t. Then the precipitated yellow catalyst was removed by filtration. The catalyst was rinsed with toluene (2×10 mL) and the filtrates were concentrated to dryness under reduced pressure. The residual oil was dried under vacuum over the weekend to give a crude solid (11.449 g). The solid was taken-up with isopropanol (25 mL) and stirred overnight at r.t. Then, the precipitate was filtered and rinsed with isopropanol (5 mL). The wet cake (8.240 g) was dried overnight at r.t. affording the highly pure 2-carboxaldehyde-methyl-cinnamate with 74% yield (7.627 g, 40.1 mmol).

Preparation PP3

Heck Coupling of 1b and methyl acrylate to form 2b (R=5-OMe): A mixture of 2-bromo-5-methoxybenzaldehyde (1b) (4.5 g, 20.9 mmol, Aldrich), methyl acrylate (2.7 g, 1.5 eq, 2.83 mL), $Et_3N$ (7.4 g, 3.5 eq, 10.2 mL), $Pd(OAc)_2$ (93 mg, 0.02 eq), and $P(O-Tol)_3$ was stirred and heated to 80° C. over 2–3 days. The reaction mixture was cooled to r.t., partitioned between EtOAc (50 mL) and brine (50 mL). The aqueous was extracted with EtOAc (2×50 mL). The combined organic was washed with brine (1×50 mL), dried over $MgSO_4$, filtered, concentrated to yield a yellow brown oil (5.01 g, 109%). This crude oil was purified in a hot solvent Hex/EtOAc (80 mL/15 mL) to yield 2b as a pale yellow solid (3.5 g, 76%).

Preparation PP4

Heck Coupling of 1c and Methyl Acrylate to Form 2c (R=4,5-OMe): To a solution of 1c (906 mg, 3.70 mmol) in toluene (2 mL) was added $Pd(OAc)_2$ (17 mg, 0.074 mmol, 2 mol %), $P(O-Tolyl)_3$ (45 mg, 0.148 mmol, 4 mol %), methyl acrylate (0.5 mL, 5.55 mmol) and $Et_3N$ (1.5 mL, 11.1 mmol). The mixture was stirred at 80° C. for 21 h, cooled to r.t., and mixed with $H_2O$ (40 mL). The organic compounds were extracted with EtOAc (50 mL), washed with brine (40 mL), dried ($Na_2SO_4$), and concentrated. The residue was purified by flash chromatography to provide 466 mg (47%) of recovered 1c followed by 450 mg (49%) of 2c (4,5-Ome).

Preparation PP5

Heck Coupling of 1d and Methyl Acrylate to Form 2d (R=5-$NO_2$): The procedure is same as that of 2c, yielding 82% of 2d after purification.

Preparation PP6

Reductive Amination

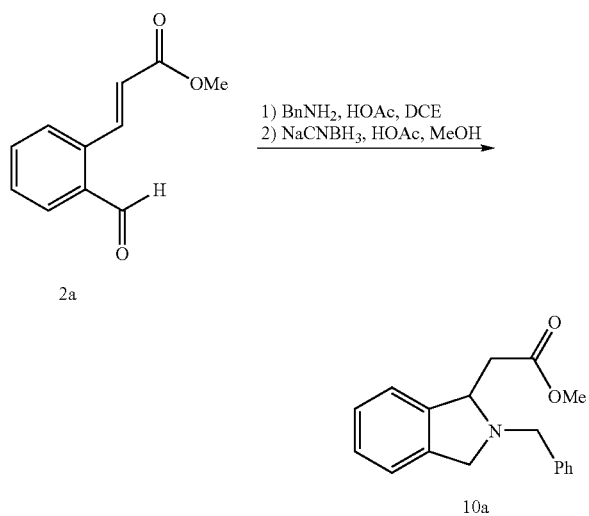

Reductive amination of (2a) with benzyl amine to form isoindoline (10a). To a solution of 2a (11.27 g, 59.2 mmol) in $ClCH_2CH_2Cl$ (60 mL) was added $BnNH_2$ (6.47 mL, 59.2 mmol), followed by HOAc (5.1 mL, 89 mmol). The mixture was stirred at r.t. for 1 h. $NaCNBH_3$ (5.58 g, 88.8 mmol) and MeOH (30 mL) were then added to the above solution. The resulting mixture was stirred at r.t. for another 2 h and quenched with sat. $NaHCO_3$ solution (150 mL). The mixture was extracted with EtOAc (2×100 mL) and the combined organic layers were washed with brine (150 mL), dried ($Na_2SO_4$), and concentrated to provide 15.3 g of crude product of 10a which was carried out for the next hydrogenolysis reaction.

Preparation PP7

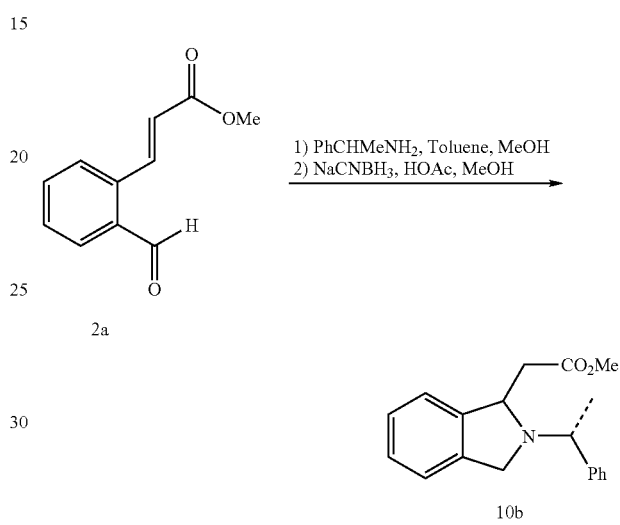

One-pot process from 2-carboxaldehyde-methyl-cinnamate to target cyclized isoindoline product using $NaBH_3CN$. 2-carboxaldehyde-methyl-cinnamate 2a (3.254 g, 17.1 mmol) was dissolved in a 1:1 MeOH: $PhCH_3$ mixture (20 mL) at r.t. R-(+)-phenethylamine (2.073 g, 17.1 mmol) was added and the solution was heated under reflux for 2 hours. HPLC in process control indicated that the imine formation was completed. Then, AcOH (2.055 g, 34.2 mmol) and $NaBH_3CN$ (2.15 g, 34.2 mmol) were successively added at r.t., the reaction mixture being cooled with a water-bath. The reaction mixture was post-agitated overnight. Water (10 mL), MeOH (20 mL) and 37% HCl (2.8 mL) were successively added and the organic layer was extracted. The aqueous layer was washed with $PhCH_3$ (10 mL). Then, the aqueous layer was made basic with 5N NaOH (20 mL) and MeOH was concentrated to partly remove MeOH. Extraction with EtOAc (2×25 mL) was performed. The combined organic layers were dried over MgSO4, filtered and rinsed with EtOAc (10 mL). The filtrates were concentrated under reduced pressure and the residual oil was dried under vacuum overnight at r.t. to afford the target cyclized isoindoline product 10b with 92% yield (4.642 g, 15.7 mmol). HPLC % area indicated that the 2 diastereomers were produced in a 55:45 ratio. $^1H$ NMR confirmed this result by integration of the methyl group of the phenethyl substituent. Note: The Heck or Heck-type coupling was performed in toluene with a slight excess of methylacrylate which was removed by distillation before the MeOH and the R-(+)-phenethylamine addition.

Preparation PP8

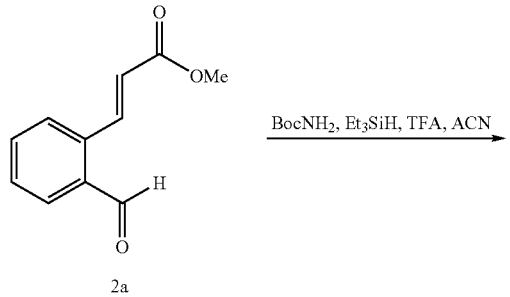

2a

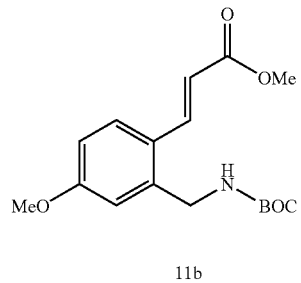

11b

Reductive amination of 2b with t-butyl carbamate to form 11b: A mixture of aldehyde 2b (600 mg, 2.72 mmol) Et$_3$SiH (955 mg, 3 eq, 1.31 mL), TFA (620 mg, 2 eq, 420 uL), t-butyl carbamate (980 mg, 3 eq) in acetonitrile (15 mL) was stirred at room temperature over 2 days. Removed the solvent on a Rotary evaporator and purified the crude residue on a flash column (100 g SiO$_2$, 7:1→6:1 Hex/EtOAc). Collected 307 mg good desired product 11b (35%); 195 mg product contaminated with aldehyde SM (22%).

Preparation PP10

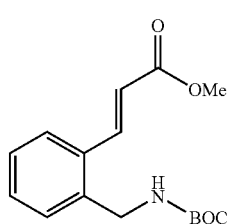

11a

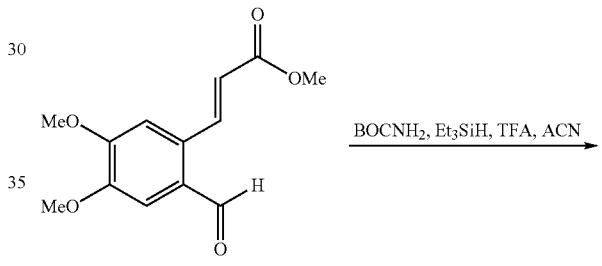

11c

Reductive amination of (2a) with t-butyl carbamate to form (11a): To a solution of aldehyde 2a (238 mg, 1.25 mmol) in CH$_3$CN (8 mL) was added t-butyl carbamate (439 mg, 3.75 mmol), followed by triethylsilane (0.6 mL, 3.75 mmol) and TFA (0.19 mL, 2.5 mmol). The mixture was stirred at r.t. overnight, quenched with sat. NaHCO$_3$ solution (20 mL) and extracted with EtOAc (2×30 mL). The combined organic layers were washed with brine (30 mL), dried (Na$_2$SO$_4$) and concentrated. The residue was purified by flash chromatography (hexane/EtOAc 3:1) to provide 317 mg (87%) of 11a.

Preparation PP9

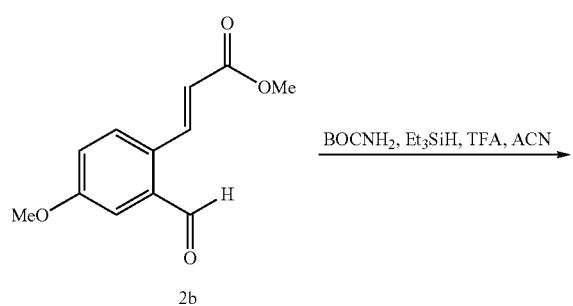

2b

Reductive amination of (2c) with t-butyl carbamate to form (11c): To a solution of aldehyde 2c (411 mg, 1.64 mmol) in CH$_3$CN (10 mL) was added t-butyl carbamate (580 mg, 4.93 mmol), followed by triethylsilane (0.8 mL, 4.93 mmol) and TFA (0.25 mL, 3.28 mmol). The mixture was stirred at r.t. overnight, quenched with sat. NaHCO$_3$ solution (30 mL) and extracted with EtOAc (2×30 mL). The combined organic layers were washed with brine (30 mL), dried (Na$_2$SO$_4$) and concentrated. The residue was purified by flash chromatography (hexane/EtOAc 3:1, hexane/EtOAc 1:1) to provide 535 mg (93%) of 11c.

Preparation PP11

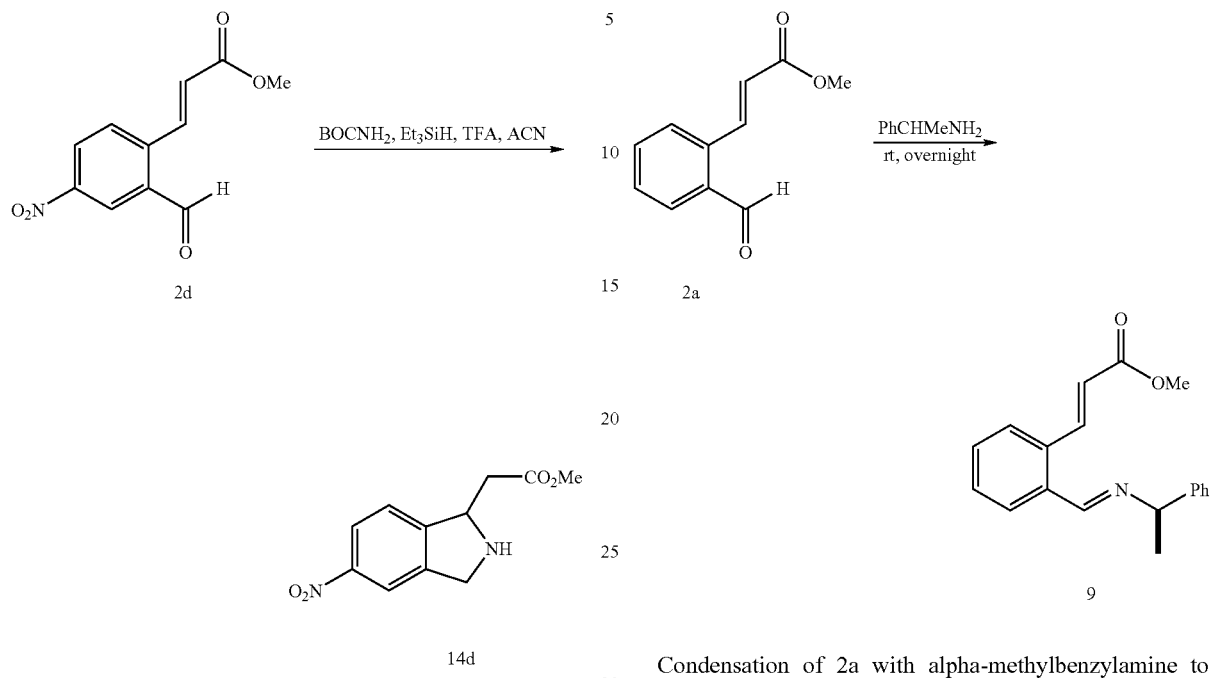

To a solution of 2d (1.02 g, 4.34 mg) in CH$_2$Cl$_2$/CH$_3$CN (1:1 24 mL) was added BocNH$_2$ (1.5 g, 13.02 mmol), Et$_3$SiH (2.1 mL, 13.02 mmol), and TFA (0.67 mL, 8,67 mmol). The mixture was stirred at r.t. for 7 h. A precipitate was formed during the reaction. The reaction mixture was quenched with sat. NaHCO$_3$ solution (30 mL), and diluted with CH$_2$Cl$_2$ (40 mL). The organic layer was washed with brine (30 mL), dried (Na$_2$SO$_4$), and concentrated. The residue was purified by flash chromatography (hexane/EtOAc 3:1, then CH$_2$Cl$_2$/EtOAc 10:1) to provide 2.08 g yellow solid which still containing BocNH$_2$. The product is not the desired Boc-carbamate 14c. LC-MS result showed that the product is the Schiff base intermediate.

To the above product (420 mg) in CH$_2$Cl$_2$ (10 mL) was added Et$_3$SiH (1 mL) and TFA (0.4 mL). The mixture was stirred at r.t. for 1 h and small amount of sample was taken for NMR. NMR analysis demonstrated that the starting material was consumed and the product was 14c. TFA (0.7 mL) was then added to the above mixture and the resultant solution was stirred at r.t. for another 5 h and concentrated. The residue was dissolved in EtOAc (20 mL) and washed with H$_2$O (10 mL). The aqueous layer was basified with sat. NaHCO$_3$ (30 mL) and the organic compounds were extracted with CH$_2$Cl$_2$ (2×25 mL). The combined organic layers were washed with brine (20 mL), dried (Na$_2$SO$_4$) and concentrated to provide 218 mg of the cyclized compound 14c.

Preparation PP12

Condensation of 2a with alpha-methylbenzylamine to Form Imine 9. 2-carboxaldehyde-methyl-cinnamate 2a (0.897 g, 4.72 mmol) was dissolved in MeOH (10 mL) at r.t. R-(+)-phenethylamine (0.577 g, 4.76 mmol) was added and the solution was heated under reflux for 2 hours. HPLC in process control indicated that the imine formation was completed. The solvent was stripped on a rotary evaporator and the resulting oil was dried at r.t. under vacuum overnight. The Schiff base 9 was obtained almost quantitatively (1.412 g, 4.81 mmol).

Preparation PP13

Michael Addition:

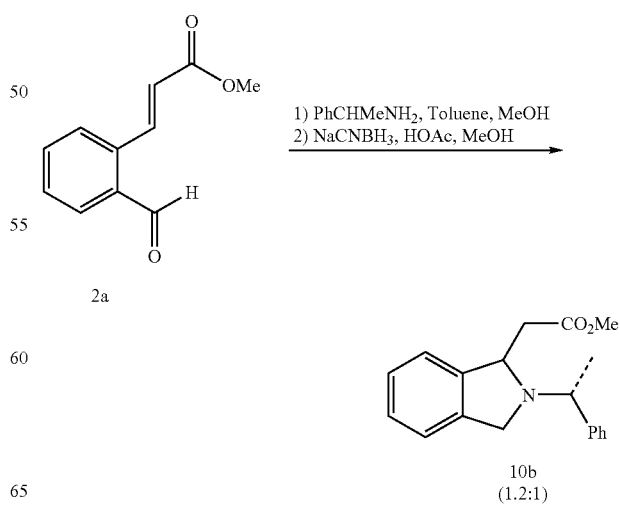

The compound of alpha-methyl benzylamine was applied as the auxiliary. As shown above, the one-pot reaction of aldehyde 2a and alpha-methyl benzylamine gave 90% of 10b with a ratio of 1.2:1.

Step-wise Reduction, Amination, and Cyclization:

Condensation of aldehyde 2a with alpha-methylbenzylamine in acetonitrile, methanol, methanol/toluene(1:1) or toluene afforded imine 9 in excellent yield. Reduction of the imine was initially carried out at r.t. with NaCNBH$_3$/HOAc. As a result, a poor ee ratio (1.2:1) was obtained, similarly to the previous described one-pot procedure. But when the reaction was carried out with NaBH$_4$/TFA at r.t., the ratio was elevated to 2:1. By lowering the reaction temperature to −78° C., the ratio was increased to 5 to 6:1.

Preparation PP14

Cyclization of t-Butyl carbamate (11a): The N-Boc isoindoline methyl ester 12 was originally synthesized from 11a via deprotection of Boc with TFA, followed by basic workup, and protection with a Boc group. This procedure has been greatly improved by a one-step procedure.

Preparation PP15

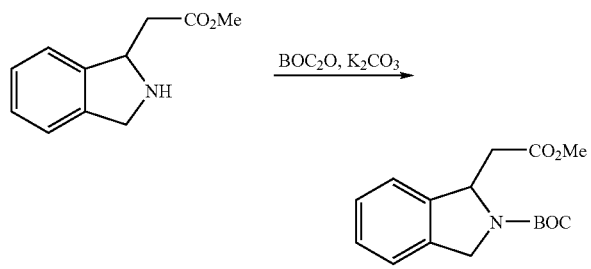

In a 3 L 3-neck round bottom flask equipped with a nitrogen inlet, thermocouple and mechanical stirrer, a solution of 160 g (1.15 moles) of K$_2$CO$_3$ in 180 mL of water was stirred at r.t. Solid BOC anhydride 120 g (0.55 moles) was added in one portion forming a semi-solution. To the reaction mixture, a solution of the crude amino ester starting material, 87 g (0.46 moles) in 120 mL of THF was added slowly at such a rate to keep the internal temperature below 35° C. A mild effervescence was observed. The reaction mixture was stirred for 18 hours at r.t. Analysis of a reaction aliquot via NMR (DMSO$_6$) indicates the desired product. The reaction was diluted with brine and the product extracted with EtOAc. The organic layer was dried over Na$_2$SO$_4$, filtered, and concentrated to yield a dark oil, 150.1 g, >100% yield. The crude material was taken on to the next step.

Preparation PP16

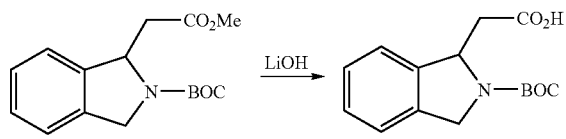

In a 3-L 3-neck round bottom flask equipped with a mechanical stirrer, thermocouple, and reflux condenser, a solution of 150 g (approx. 0.46 moles) of crude N-BOC ester starting material in 750 mL of methanol was stirred at r.t. To the solution, 750 mL of water was added and the cloudy mixture was stirred vigorously. Solid LiOH 25 g (1.03 moles) was added in small portions at such a rate to maintain the internal temperature below 45° C. Upon completion of addition, the reaction was stirred overnight at r.t. becoming a dark green color. After 18 hours the reaction was concentrated to yield a thick semisolid. The crude product was dissolved in EtOAc and washed with 1 N HCl quickly, followed by two brine washes. The organic layer was dried with Na$_2$SO$_4$, filtered and concentrated to yield 81 g of a dark green solid. The aqueous layers were combined and back extracted with methylene chloride, dried over Na$_2$SO$_4$, filtered, and concentrated to yield 6 g of a dark green solid. Both solids were combined to yield 87 g of desired product confirmed via NMR (DMSO$_6$).

Preparation PP17

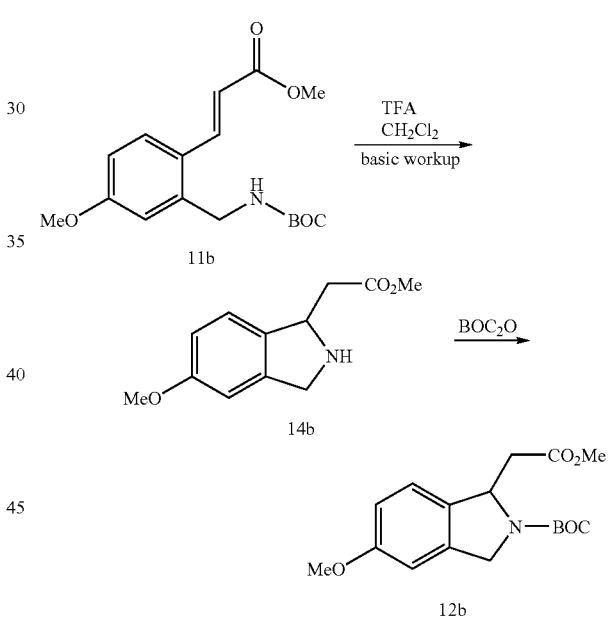

Synthesis of 14b: Dissolved the N-boc compound 11b (200 mg, 0.62 mmol) in CH$_2$Cl$_2$ (1.0 mL). Cooled the clear light yellow solution to 0° C. Added slowly TFA (~710 mg, 10 eq, ~500 microliter) via a syringe. Removed the cooling bath and stirred the clear light brown solution at r.t. overnight. TLC (3:1 Hex/EtOAc, UV) confirmed a complete reaction. Removed the TFA on a rotavapor. Added EtOAc and concentrated again (twice). The crude residue was partitioned between EtOAc (10–15 mL) and a sat. NaHCO$_3$ (10–15 mL). The aqueous was extracted with EtOAc (2×10 mL). The combined organic was dried over MgSO$_4$, filtered, and concentrated to yield a light brown wet solid (212 mg, 138%). NMR (CD$_3$OD) confirmed the desired isoindoline 14b. This crude isoindoline was used in the next protection step without purification.

Preparation PP18

Synthesis of 12b: To a mixture of the isoindoline 14b (190 mg, 0.859 mmol), K₂CO₃ (189 mg, 1.5 eq) in a solvent 1:1 THF/H₂O (1.0 mL) at r.t. was added BOC₂O (210 mg, 1.1 eq). The reaction mixture was stirred at r.t. overnight. TLC (3:1 Hex/EtOAc, UV) confirmed a complete reaction. Diluted the mixture with EtOAc (15 mL), and washed with H₂O (1×20 mL). The aqueous was extracted with EtOAc (1×20 mL). The combined organic was washed with brine (1×20 mL), dried over MgSO₄, filtered, concentrated to yield a clear brown oil (340 mg, 123%). This crude oil was purified on a prep TLC plate (2×1,000 micron, solvent 2:1.5:0.5 CHCl₃/Hex/EtOAc) to yield 12b a clear yellow oil (190 mg, 69%). ¹H and ¹³C NMR (CDCl₃) were obtained.

Procedure PP19

Synthesis of 12d (5-NO₂) by Boc-protection. The compound was prepared by following the same procedure as described for 12b.

Preparation PP20

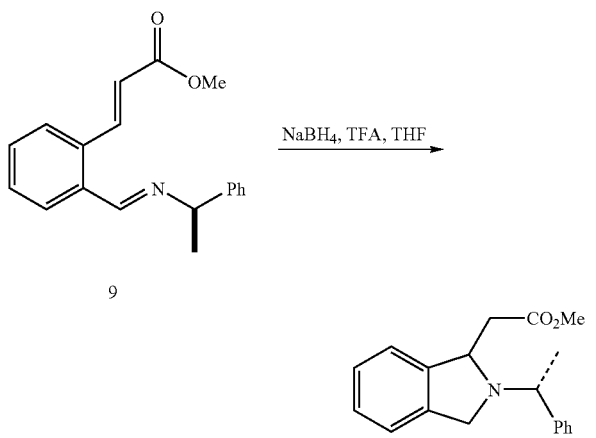

The imine 9 (1.412 g, 4.81 mmol) was dissolved in anhydrous THF (10 mL) at r.t. and TFA (5 mL) was added. The black solution was then cooled to −78° C. (dry ice bath) and NaBH₄ (0.893 g, 23.6 mmol, 5 eq.) was added in 2 portions over 5 minutes. Then, the reaction mixture was post-agitated at −78° C. for 3 hours and allowed to gently warm at r.t. overnight. Water (20 mL), cyclohexane (10 mL) and EtOH (20 mL) were successively added and the organic layer was extracted and discarded. The aqueous layer was made basic with 5N NaOH (20 mL) and extracted two times with a 2:1 EtOAC/PhCH₃ mixture (30 mL). The combined organic layers were dried over MgSO4, filtered and rinsed with EtOAc (10 mL). The filtrates were concentrated under reduced pressure and the residual oil was dried under vacuum overnight at r.t. to afford the target cyclized isoindoline product 10b (1.273 g, 4.31 mmol) with 91.4% yield. HPLC % area indicated that the 2 diastereomers were produced in a 84:16 ratio (de 68%). ¹H NMR confirmed this result by integration of the methyl group of the phenethyl substituent.

Preparation PP20

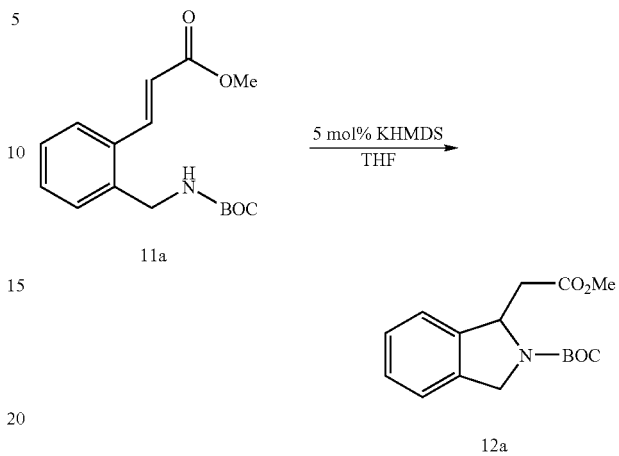

N-Boc methyl ester 11a (36.3 g, 0.125 mol) was dissolved in THF (250 mL), and the solution was cooled to about 0° C. A solution of potassium bis(trimethylsilyl)amide (1.24 g, 0.05 mol. eq.) was added slowly via a syringe under nitrogen atmosphere. The temperature was raised about 8 degrees during the addition. The cooling bath was removed and the solution was stirred at r.t. for 30–45 min. The clear brown solution was poured into a separation funnel containing about 100 mL of a saturated NH₄Cl. The layers were separated. The aqueous layer was extracted with EtOAc (2×50 mL). The combined organic was washed with brine (1×100 mL), dried over Na₂SO₄, filtered, concentrated on a Rotary evaporator to a clear yellow oil (37.3 g). This crude oil was purified on a flash column (600 g SiO₂), with a gradient solvent 6:1 Hex/EtOAc (2.1 L), 5:1 Hex/EtOAc (1.2 L), 4:1 Hex/EtOAc (1.5 L) to yield 12a as a clean yellow oil (34.5 g, 95%).

Preparation PP21

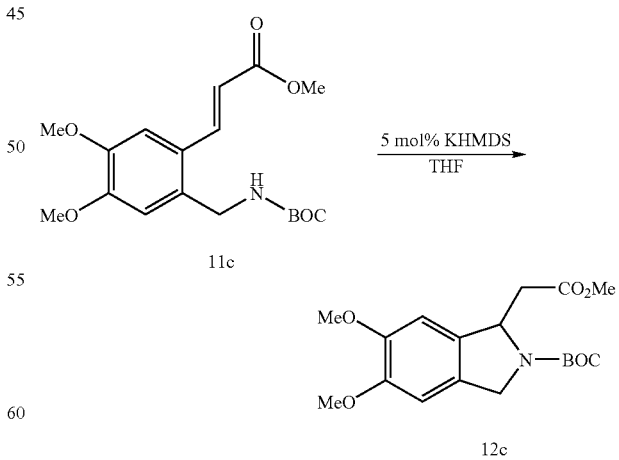

To a solution of 11c (535 mg, 1.52 mmol) in THF (10 mL) was added KHMDS (0.5 M in toluene, 0.1 mL, 0.05 mmol, 2 mol %). The mixture was stirred at r.t. for 20 min, quenched with sat. NH₄Cl solution (20 mL), and diluted with EtOAc (20 mL). The organic layer was separated, washed with brine (20 mL), dried (Na$_2$SO$_4$) and concentrated. The residue was filtered through a plug of silica gel (EtOAc/CH$_2$Cl$_2$ 1:10) to give 530 mg (99%) of 12c as an off white solid.

Preparation PP22

Deprotections:

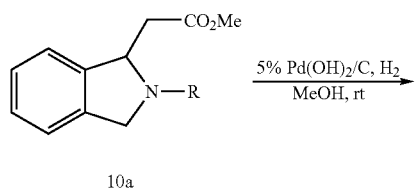

10a

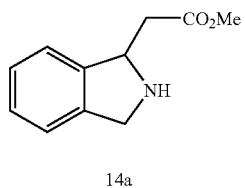

14a

Hydrogenolysis of 10a (R=Bn) to Form (14a): To a solution of crude 10a (15.3 g, 54.4 mmol) in MeOH (100 mL) was added Pd(OH)$_2$/C (Pearlman's catalyst, 1.02 g, 6 mol %) in a par-shaker bottle. The suspension was shaken under 30 psi H$_2$ pressure overnight in the par-shaker, and filtered through a plug of celite. The filtrate was concentrated to provide 10.1 g of crude 14a as brown oil. (The procedure is same for the methyl benzylamine isoindoline substrate 10b)

Preparation PP23

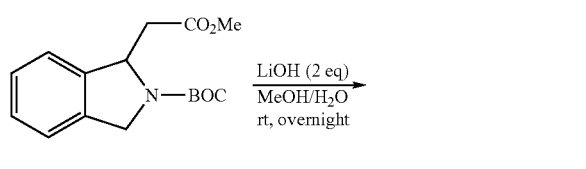

12a

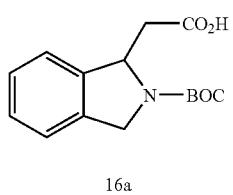

16a

In a typical reaction a mixture of the isoindoline ester 12a (92 mg, 0.316 mmol) in 1:1 MeOH/H$_2$O (2 ml) was treated with LiOH (15 mg, 2 eq) at r.t. overnight. Diluted the mixture with CH$_2$Cl$_2$ (5 ml) and water (5 ml). Adjusted the pH of the reaction mixture to 1–3 with a 10% NaHSO$_4$ solution. Separated the layers. The aqueous was extracted with CH$_2$Cl$_2$ (1×10 ml). The combined organic was dried over Na$_2$SO$_4$, filtered, concentrated to yield 16a as a pale yellow foam (76 mg, 87%). NMR (CDCl$_3$) showed a clean desired acid product.

It is noted that he reaction time must be more than 6 hours. The crude foam can be purified by slurry in warm hexane and then filter to yield a tan solid. Hydrolysis using KOH (2–5 eq) in 1:1 MeOH/H$_2$O overnight would give the same result.

Preparation PP24

Resolution:

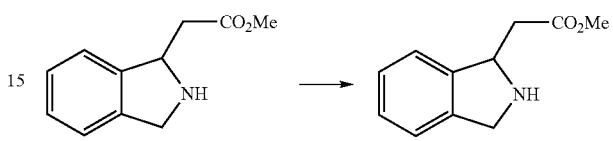

Purification of Partially Resolved Isoindoline-caboxylic acid methyl ester: A solution of the crude material (97.62 g) isoindolinecaboxylic acid methyl ester in CH$_2$Cl$_2$ (350 mL) was extracted with 1M HCl (400 mL, 200 mL). The combined aqueous portions were washed with CH$_2$Cl$_2$ (4×250 mL) and then made basic with K$_2$CO$_3$ solution (85 g in 150 mL of water). The mixture was extracted with CH$_2$Cl$_2$ (6×100 mL) and the combined organic extracts were dried (Na$_2$SO$_4$) and concentrated to give partially resolved Isoindolinecaboxylic acid methyl ester as an oil (33.2 g). 60% ee by chiral CE.

Preparation PP25

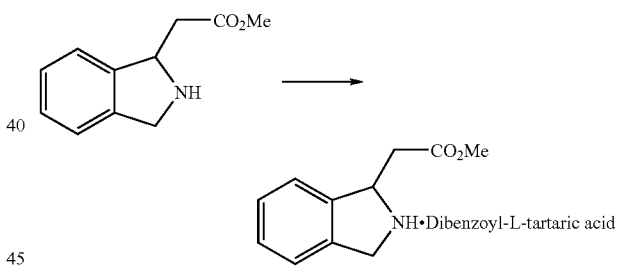

Resolution of Partially Resolved Isoindoline-caboxylic acid methyl ester: A solution of partially resolved isoindoline-caboxylic acid methyl ester (33.24 g, 0.174 mol) in EtOH (130 mL) was treated slowly with a solution of dibenzoyl-L-tartaric acid (56.06 g, 0.156 mol) in EtOH (200 mL). The solution was seeded with seeded with product and stirred at r.t. for 4 hours. Pure product was collected by filtration, washed with EtOH (30 mL) and dried to off-white crystals (60.49 g). 96.5% ee by chiral CE.

Preparation PP26

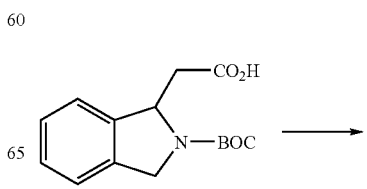

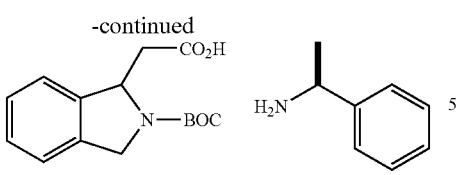

Resolution of N-BOC Isoindolinecaboxylic acid: A solution/slurry of racemic N-BOC Isoindolinecaboxylic acid (114.5 g, 0.413 mol) in EtOAc (1000 mL) was treated slowly with triethylamine (28.8 mL, 0.206 mol), followed by (S)-(−)-alpha-methylbenzylamine. The solution was seeded with product and stirred at r.t. overnight. The product was collected by filtration, washed with EtOAc (200 mL) and dried to a white powder (62.98 g). 97.6% ee by chiral CE.

Asymmetric Hydrogenation Routes

Part I: Synthesis of the Z-isomer (Precursor of Asymmetric Hydrogenation)

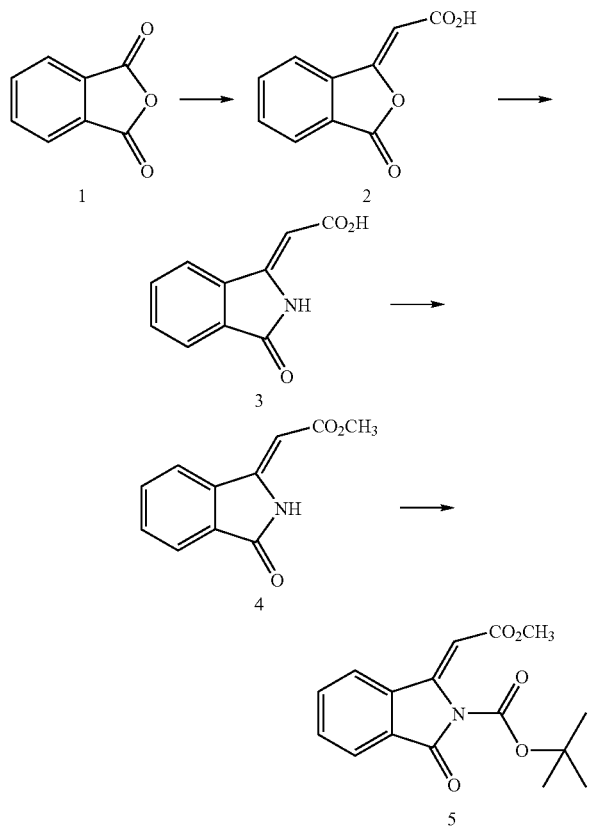

Preparation PP27

Z-isomer 5 was synthesized as outlined in Scheme P1. Compound 5 was shown to be a single isomer by HPLC and H-1 nmr. The double bond stereochemistry was derived from comparative NOE data using the purported E-isomer (Scheme P1). The best chiral induction was achieved using compound 8/Ferrotane/MeOH-THF. With regard to the conversion of 9 to 10, which would constitute a formal asymmetric synthesis of isoindolene 10, this has been achieved using Super hydride-$BF_3.OEt_2$ However, the product was a mixture of 10 and the corresponding de-BOC (deprotected) compound.

Preparation PP28

Compound 2 (Scheme P1)

Phthalic anhydride (751.5 g, 5.014 mole), potassium acetate (498 g, 5.014 mole) and acetic anhydride (1L) were stirred together under nitrogen. The mixture was slowly warmed to 145–150° C. and stirred for 10 minutes, then at 140° C. for 20 minutes. The mixture was allowed to slowly cool to 80° C. over 1 hour. Three volumes of water were added causing precipitation of a solid. After filtration, the filtered solid was washed with warm water and pulled as dry as possible for 30 minutes. The solid was then washed with ethanol and acetone respectively. If required further purification could be achieved by slurring the solid in acetone, at room temperature, for 15 minutes, then filtration. Drying in vacuo at 50° C. for 20 hours gave compound 2 as an off-white solid, 470 g (48%) with an NMR purity of approx. 90%.

Preparation PP29

Compound 3 (Scheme P1)

Compound 2 (470 g, 2.47 mole) was added to stirred aqueous ammonia (470 ml conc. $NH_3$ in 4.7 L water). The resultant mixture was stirred at room temperature for 1 hour then filtered. The filtered solid was washed with water. The combined aqueous filtrate and washings were carefully acidified with 6M aq. HCl (2.35 L). The precipitate was removed by filtration and dried in vacuo at 50° C. to give compound 3 as a yellow solid, 259 g (52%).

Preparation PP30

Compound 4 (Scheme P1)

Compound 3 (511 g, 2.7 mole) was slurred in toluene (10 vol). Thionyl chloride (385 g, 3.24 mole) was added over 10 minutes to the stirred mixture, which was then heated to reflux for 1.5 hours. H-1 NMR analysis indicated approx. 80% conversion to acid chloride). DMF (3.7 ml) was added and the mixture refluxed an additional 3 hours. The resultant mixture was allowed to cool to 35° C. and methanol (1.27L) added at such a rate that the reaction temperature was maintained at 30–35° C. The reaction mixture was kept at this temperature a further 15 minutes then concentrated in vacuo to give compound 4 as a brown solid, 536 g (quantitative).

Preparation PP31

Compound 5 (Scheme P1)

Compound 4 (750 g, 3.65 mole) was dissolved in acetonitrile (15 L). The stirred mixture was cooled to 0–5° C. and DMAP (624 g, 5.11 mole) added in one portion. After 10 minutes BOC anhydride (1115 g, 5.11 mole) was added in one portion: there was a slight exotherm accompanied by gas evolution. The mixture was stirred at room temperature for 5 hours, and then concentrated in vacuo. The residue was dissolved in EtOAc and washed with 10% aqueous citric acid, satd. aq. Na$_2$CO$_3$ and water respectively. After drying, concentration of the organics gave a thick syrup. This material was run through a plug of silica gel (1.5 kg) eluting with 1:1 EtOAc-hexane. Compound 5 was isolated as a dark solid, 619 g (55%). Careful chromatography on silica gel eluting with 20% EtOAc-hexane gave 5 as a fluffy white solid.

Scheme P2

Part II: Synthesis of the E-isomer (Precursor of asymmetric hydrogenation)

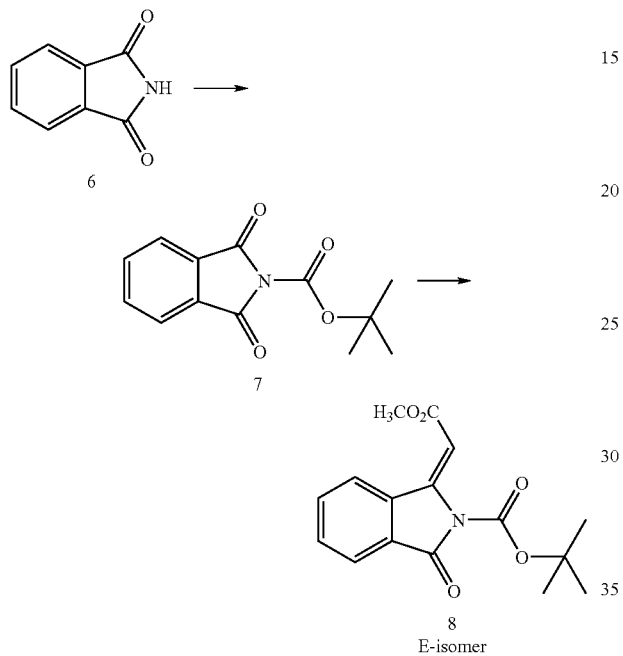

Preparation PP32

The E-isomer of Compound 8 (Scheme P2) was prepared as shown in Scheme P2.

Preparation PP33

Compound 7 (Scheme P2)

The compound 7 was prepared according to the procedure of Einhorn et al, *Synth. Commun.* 2001, 31(5), 741–748.

Preparation PP34

Compound 8 (Scheme P2)

Compound 7 (15.00 g, 60.7 mmole) and methyl(triphenyl phosphoranylidene)acetate (41.40 g, 121.3 mmole) were slurred in toluene (150 ml). The mixture was stirred at reflux and monitored for reaction of 7 by GC. After 1.5 hours the reaction appears complete by GC. After cooling to room temperature, the mixture was filtered. The solid on the filter was washed with toluene until colorless. The combined filtrate/washings were concentrated in vacuo to leave a tan solid. This material was coated on silica gel and chromatographed on silica gel (1 kg) eluting with 10% EtOAc-hexane. Compound 8 was isolated as a white or pale yellow powder, 5.52 g (30%).

Scheme P3

Asymmetric hydrogenation:

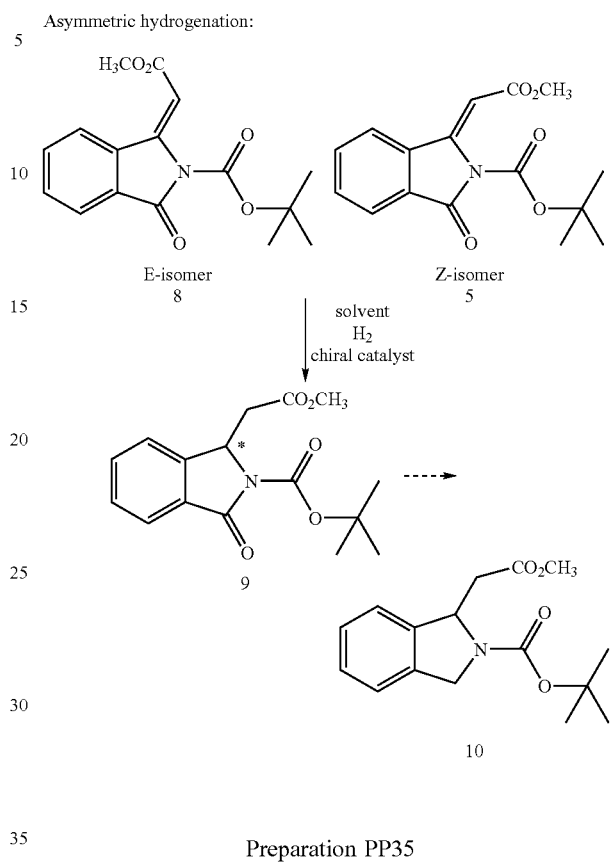

Preparation PP35

Screening of chiral hydrogenation conditions indicated that the best chiral induction was achieved using compound 8/Ferrotane/MeOH-THF. With regard to the conversion of 9 to 10, which would constitute a formal asymmetric synthesis of isoindolene 10, this has been achieved using Super hydride-BF$_3$.OEt$_2$. However, the product was a mixture of 10 and the corresponding de-BOC (deprotected) compound.

Scheme P4

Coupling of chiral isoindoline with d-4-chloro-Phenyl-alanine using tartrate salt:

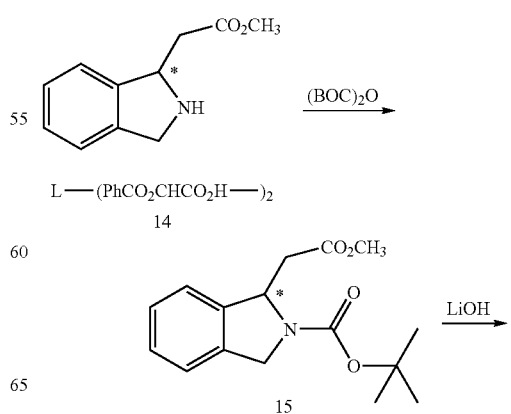

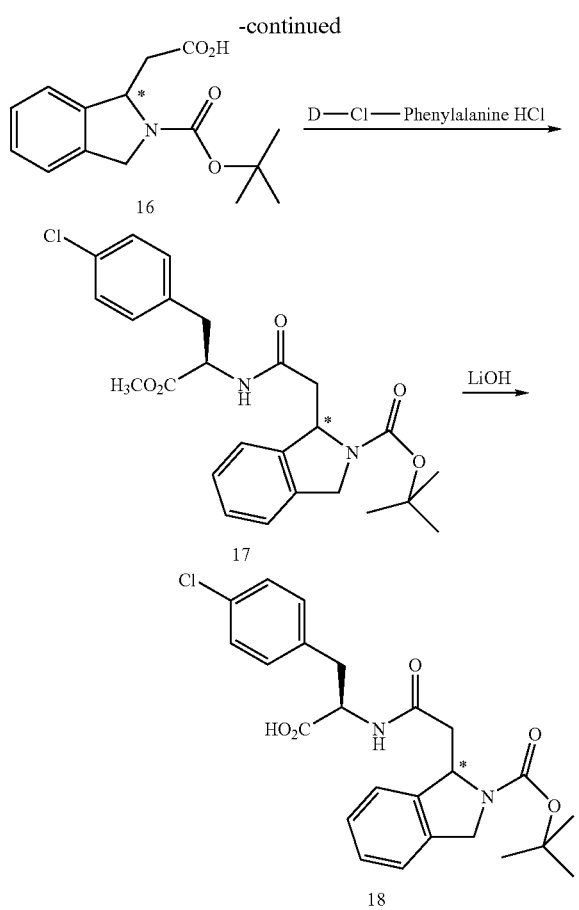

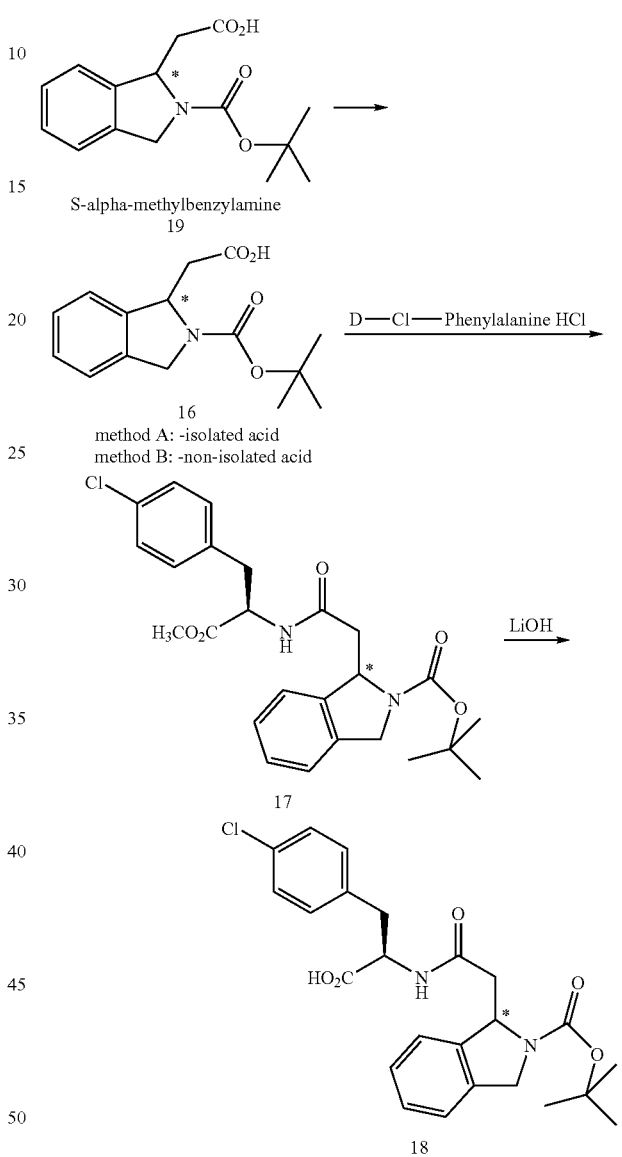

Preparation PP36

Compound 15 (Scheme P4)

Tartrate salt 14 (58.00 g, 100.27 mmole) was slurred in water (580 ml). Solid NaHCO₃ (25.27 g, 300.8 mmole) was carefully added. BOC anhydride (22.98 g, 105.28 mmole) was added in one portion and the progress of the reaction monitored by reverse phase HPLC. After 1 hour additional BOC anhydride (2.18 g, 10.00 mmole) was added. The reaction was complete (by HPLC) after 3 hours. The mixture was extracted with EtOAc (2×250 ml). The combined organic extracts were washed with water (250 ml) and dried (MgSO₄). Filtration and concentration in vacuo gave 15 as a clear light brown oil (31.33 g) contaminated with a small amount of t-BuOH and BOC anhydride. This material was used directly in the next reaction.

Preparation PP37

Compound 16 (Scheme P4)

Ester 15 (29.21 g, 100.26 mmole) was dissolved in 3:1 THF-water (100 ml). LiOH (6.00 g, 250.65 mmole) was added in 1 portion to the stirred solution. After 17 hours, the mixture was stripped to dryness and the residue dissolved in water (500 ml). EtOAc (250 ml) was added and solid NaHSO₄ added to the stirred mixture until the pH=3. The organic layer was separated and the aqueous layer extracted with EtOAc (250 ml). The combined EtOAc layers were dried (MgSO₄). Filtration and concentration in vacuo gave acid 16 as a light tan solid, 27.10 g (97%).

The chemistry used is shown in Scheme P5. Two protocols were used: method A used isolated 16, method B used a solution of 16 derived from resolved salt 19.

Preparation PP38

Compound 17 (Scheme P5, Method A)

Acid 16 (24.18 g, 87.2 mmole) and D-chloro-phenylalanine hydrochloride (21.81 g, 87.2 mmole) were dissolved in CH₂Cl₂ (100 ml) and DMF (25 ml). The mixture was stirred at ambient temperature. HOBT (13.55 g, 100.3 mmole) and Hunig's base (45.6 ml, 33.81 g, 261.6 mmole) were added. HATU (38.13 g, 100.3 mmole) was added in 1 portion (there was a rapid exotherm to 50° C.). The mixture was stirred for 90 minutes then diluted with EtOAc (750 ml). The resulting mixture was washed with water, 5% KHSO$_4$, brine and satd. NaHCO$_3$ respectively, then dried. Filtration and concentration in vacuo gave crude 17 as a brown foam. The product was purified by chromatography on silica gel (1 kg) eluting with 1:1 EtOAc-hexane. Ester 17 was isolated as a tan powder, 38.85 g (94%).

Preparation PP39

Compound 17 (Scheme P5, Method B)

Resolved salt 19 (96.27 g, 232.5 mmole) was partitioned between water (500 ml) and CH$_2$Cl$_2$ (250 ml) Solid KHSO$_4$ was added portion wise until pH=2.5. Separate the organic layer and extract the aqueous layer with CH$_2$Cl$_2$ (150 ml). The combined organic layers were dried (MgSO$_4$) then filtered. To this solution was added 4-chloro-D-phenylalanine (58.16 g, 232.5 mmole), HOBT (34.57 g, 255.8 mmole), Hunig's base (93.2 ml, 69.13 g, 534.9 mmole) and finally HATU (97.26 g, 255.8 mmole). The resultant mixture was stirred at room temperature for 18.5 hours, and then poured onto a plug of silica gel (1 kg). This was washed with 1:1 EtOAc-hexane until no more product elutes. Ester 17 was isolated as a pink foam, 101.79 g (93%): contains about 1% unreacted 16.

Preparation PP40

Compound 18 (Scheme P5)

Ester 17 (38.64 g, 81.7 mmole) was dissolved in 3:1 THF-water (200 ml). LiOH (2.15 g, 89.9 mmole) was added to the mixture, which was stirred at room temperature for 2 hours. The solvent was then removed in vacuo and the residual solid taken up in water (600 ml). This was extracted with MTBE (250 ml). The aqueous layer was separated and stirred with EtOAc (250 ml), and solid KHSO$_4$ was added portion wise until pH=3. The layers were separated and the aqueous extracted with EtOAc (250 ml). The combined organic layers were dried over MgSO$_4$. Filtration and concentration in vacuo gave acid 18 as a light pink foam, 38.41 g (35.71 g corrected for residual solvent, 95%).

Preparation PP41

Step 1: Esterification

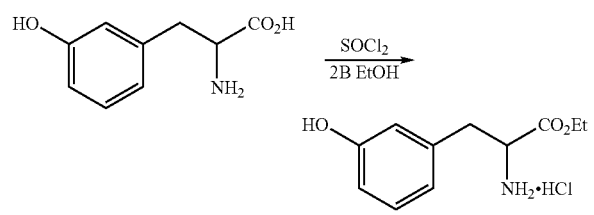

In a 22 L 4-neck round bottom flask equipped with a reflux condenser, thermocouple and nitrogen inlet, a slurry of 1000 g (5.4 moles) of m-tyrosine in 10 L of 2B-3 EtOH was cooled to 5° C. To the slurry, 350 mL (12.4 moles) of thionyl chloride were added dropwise via an addition funnel at such a rate to maintain the reaction temperature below 20° C. Upon completion of addition, the reaction was heated to reflux temperature and stirred for 18 hrs. The reaction was concentrated to one-third the volume and 8 L of MTBE were charged. The resulting thick slurry was stirred for 14 hrs in a rotary evaporator at r.t. The resulting solid was isolated on a filter pad and dried at 40° C. for 48 hrs yielding 1288 g (95%). NMR (DMSOd$_6$) indicated desired material.

Preparation PP42

Step 2: Pictet-Spengler

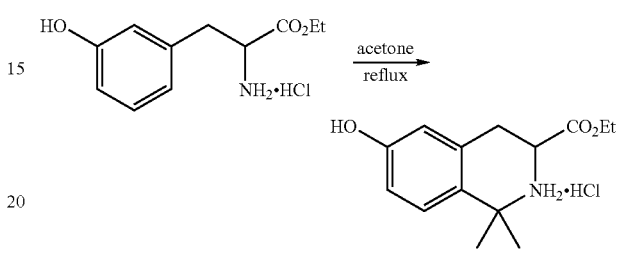

In a 22 L 4 neck round bottom flask equipped with a mechanical stirrer, thermocouple, and reflux condenser placed on top of a Soxhlet extractor charged with 4° A sieves, a semi-solution of m-tyrosine ethyl ester hydrochloride 1288 g (5.26 moles) in 13 L of acetone was heated to reflux temperature. The condensate was filtered through the sieves to remove water. The reaction was stirred vigorously at reflux for 48 hrs. An NMR sample in DMSOd$_6$ indicated the absence of starting material. The reaction was cooled to r.t. and concentrated to yield an off-white solid, 1411 g (94%).

Preparation PP43

Step 3: Triflation

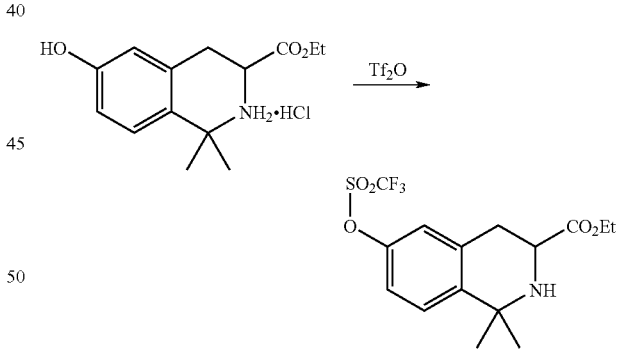

In a 22 L 4 neck round bottom flask equipped with a reflux condenser, mechanical stirrer, nitrogen inlet, and a thermocouple, 1240 g (4.35 moles) of the starting material salt in 12.4 L of methylene chloride was cooled to 4° C. To the mixture, 1452 mL (10.4 moles) of triethylamine were added and stirred into solution. Triflic anhydride, 1472 mL (5.22 moles) was added dropwise to the reaction at such a rate to maintain the internal temperature below 10° C. The ice bath was removed and the reaction warmed to r.t. and stirred for 18 hrs. The reaction was concentrated to an oil then dissolved in 4 L of EtOAc and concentrated again to an oil in an effort to remove excess triflic anhydride The crude residue was dissolved in 4 L of EtOAc and washed with water and saturated sodium bicarbonate solution. The organic layer was isolated and dried with sodium sulfate, filtered and concentrated to yield 1720 g (>100%) of a crude dark oil which was used without further purification.

Preparation PP44

Step 4: Deoxygenation

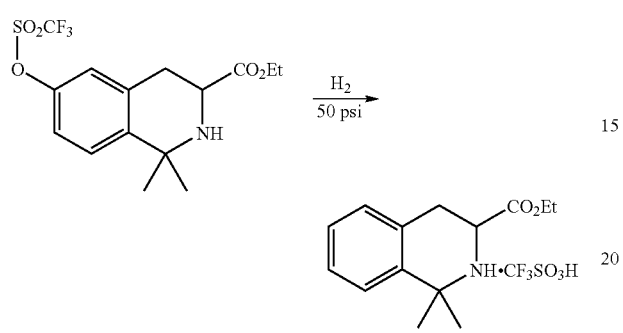

A solution of 1720 g (4.35 moles) of crude starting material in 14 L of acetone was charged to a 10 gallon stainless steel autoclave. To the solution, a slurry of 5% Pd/C in 1.2 L of toluene was added. The reaction mixture was evacuated and purged with $H_2$ gas at 50 psi two times. The reaction was stirred overnight at 50° C. with $H_2$ at 50 psi. A sample aliquot indicated no reaction had occurred. The mixture was filtered and concentrated to a thick oil and resubjected to reaction conditions. After 18 hrs, NMR of a sample aliquot indicated absence of starting material. The reaction mixture was filtered and the filtrate concentrated to yield 1581 g of an off-white solid (95%).

Preparation PP45

Step 5: Hydrolysis/Salt Formation

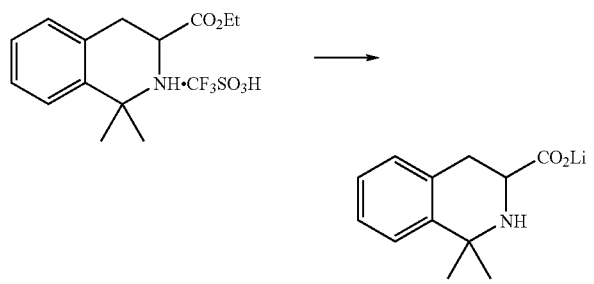

To a 2 L 3 neck round bottom flask equipped with a mechanical stirrer, thermocouple, and nitrogen inlet, a mixture of 700 g (1.83 moles) of the triflate salt starting material was charged. A solution of 427 g (1.83 moles) of the starting material free base in 13.3 L of THF was added followed by 700 mL of water. The semi-solution was stirred vigorously at r.t. To the reaction flask, 43.7 g (1.83 moles) of solid LiOH were added in small portions at such a rate to maintain the internal temperature below 35° C. The reaction was stirred for 18 hrs at r.t. and concentrated to yield a thick oil. THF (4 L) was added and the semi-solution was concentrated. This was repeated with toluene and the semi-solid was placed under house vacuum on the roto vap with stirring for 18 hrs to yield 650 g of a crude solid. The solid was reslurred in EtOAc, filtered, isolated and dried to yield 525 g (68%) of the lithium salt as an off-white solid.

Preparation PP46

Step 6: Coupling

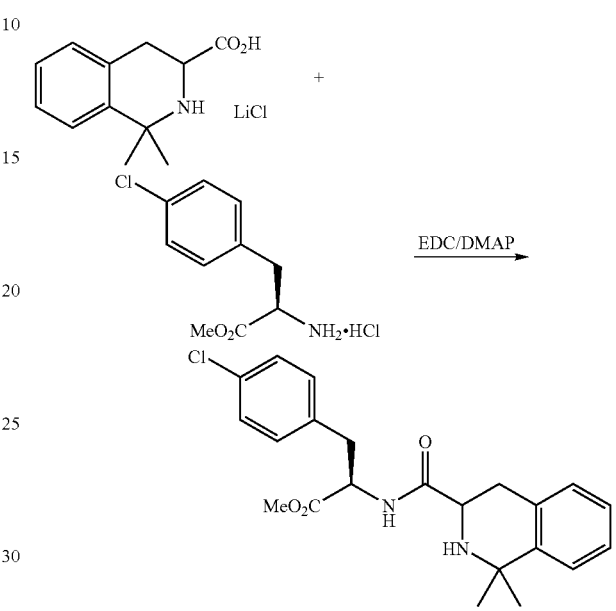

Solid d-chloro-phenylalanine 446 g (1.78 moles) was added to the semi-solution followed by 20 g (0.162 moles) of DMAP. The resulting mixture was stirred for 15 minutes then solid EDCI (1-(3-dimethylaminopropyl)-3-ethylcarbodiimide hydrochloride) 390 g (2.03 moles) was added. The reaction mixture was heated to 80° C. and stirred for 18 hours. Thin layer chromatography (1:1 EtOAc:Hex) indicated very little starting material present. The reaction was cooled to r.t. and concentrated to yield a thick oil. The crude oil was dissolved in EtOAc and washed with water, and brine. The solution was dried with sodium sulfate, filtered and concentrated to yield a thick oil, 426 g. The crude oil was chromatographed in several lots using a Waters Prep 500 chromatography apparatus. The eluent consisted of a gradient system, 5%–80% EtOAc in heptane at a flow rate of 240 ml/min over 38 minutes. The two diasteromers were separated and isolated to yield 119.04 g for the top spot and 111.3 g for the bottom spot. Conformation of both desired diastereomers was achieved via NMR ($DMSO_6$).

Preparation PP47

Resolution of tetrahydroisoquinolinecarboxylic acid ethyl ester to prepare l-tartaric acid salt:

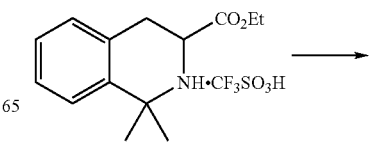

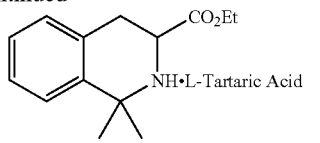

Preparation of free-base: A racemic mixture of tetrahydroisoquinolinecarboxylic acid (7.43 g) in EtOAc (60 mL) was treated with saturated NaHCO$_3$ solution (60 mL) and saturated Na$_2$CO$_3$ solution (10 mL). The mixture was agitated and the layers were separated. The organic phase was dried (Na$_2$SO$_4$) and concentrated to give the corresponding free-base as an oil (4.85 g)

Resolution: A mixture of the above free base (467 mg, 2.0 mmol), and L-tartaric acid (300 mg, 2.0 mmol) in acetone (4 mL) was stirred at r.t. overnight. The title L-tartaric acid salt was collected by filtration, washed with acetone (about 2 mL) and dried to a white powder (367 mg). 100% ee by chiral CE.

Preparation PP48

Resolution of N-BOC Tetrahydroisoquinolinecarboxylic Acid

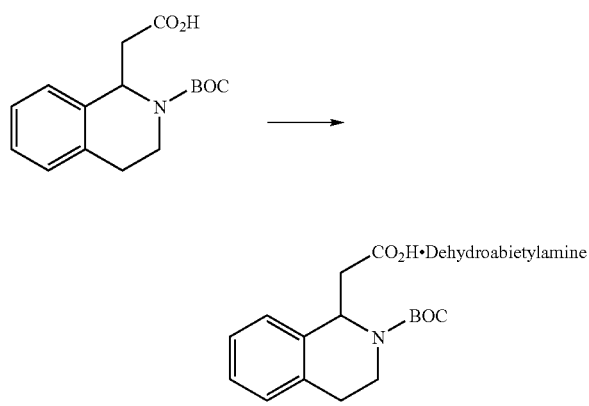

2-{2-[(tert-butyl)oxycarbonyl]-1,2,3,4-tetrahydroisoquinolyl}acetic acid dehydroabietylamine salt: Racemic 2-{2-[(tert-butyl)oxycarbonyl]-1,2,3,4-tetrahydroisoquinolyl}acetic acid (30.15 g, 103.5 mmol) was dissolved in i-PA (300 mL). Dehydroabietylamine (22.11 g, 52.7 mmol of a 68 weight % mixture) was added to the solution, which was then agitated on a multi-arm shaker for 63 h. The resultant thick paste was filtered and rinsed with i-PA (50 mL, 25 mL). Dried in a 50° C. vacuum oven to obtain a white solid (27.73 g, 52% ee by chiral CE analysis). The product was reslurred in i-PA (266 mL) and agitated on a multi-arm shaker for 23.5 h. Filtered the thick slurry and rinsed with cold i-PA (50 mL, 30 mL). Dried the cake in a 50° C. vacuum oven and obtained the product as a white solid (23.63 g, 40% yield, 94% ee by chiral CE analysis).

Scheme P6

Asymmetric Hydrogenation:

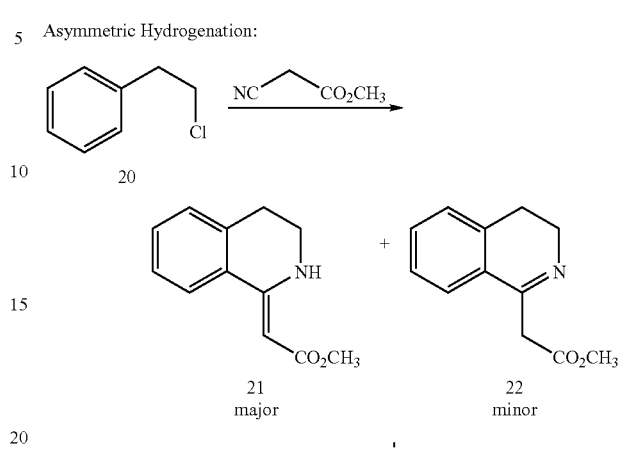

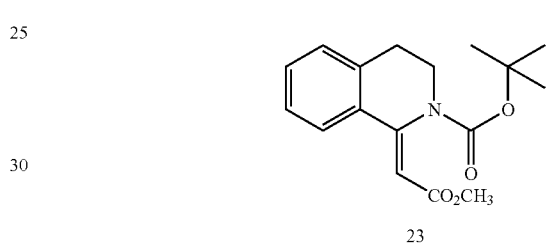

Preparation PP49

Enamine 21 (Scheme P6) was prepared as a substrate for asymmetric hydrogenation screening studies. It is formed as an approx. 10:1 mixture with imine 22. The enamine (21) may be NH-protected i.e., by a Boc protecting group. The resulting compound 23 may be subjected to asymmetric hydrogenation to afford the acetic acid or methylacetate substituted isoquinoline, which may be processed into a compound of formula I as demonstrated previously.

Preparation PP50

Compound 21 (Scheme P6)

Prepared as published W Sobotka et al, *J. Org. Chem.*, 1965, 30, 3667.

Scheme P7

Synthesis of Gem-dimethyl TIC:

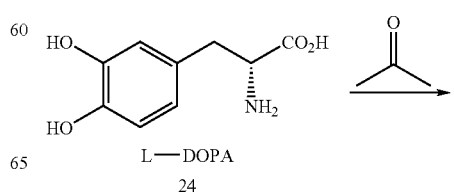

-continued

Preparation PP51

The chiral synthesis of gem-dimethyl TIC using L-Dopa as the starting material instead of tyrosine was successfully demonstrated up to the Pictet-Spengler reaction with L-DOPA and acetone. The product is a mixture of starting material 24 and product 25 (major component). The product was isolated by using common isolation procedures. An alternative isolation method is to react the mixture (24 and 25) with BOC anhydride wherein the less hindered N—H in 24 leads to preferential BOC protection of 24, allowing for ready separation of 25. Chemistry for the rest of the sequence i.e., deoxygenation reaction, has been demonstrated herein.

What is claimed is:

1. A compound of formula I:

(I)

or a pharmaceutically acceptable salts or stereoisomers thereof, wherein

G is N;
L and $L^1$ are independently hydrogen or together oxo;

A is a 5- or 6-membered carbocyclyl wherein the carbocyclyl being saturated, partially saturated or aromatic ring, and the carbocyclyl being optionally substituted with one to three substituents independently selected from R;
T is:

R is independently:
  hydrogen,
  halo,
  $C_1$–$C_8$ alkyl,
  $C_1$–$C_8$ alkoxy,
  $C_1$–$C_4$ haloalkyl,
  (D)C(O)$R^8$,
  $C_1$–$C_8$ alkyl-N($R^8$)$_2$,
  (D)OCO$R^8$,
  (D)OC(O)N($R^8$)$_2$,
  (D)N($R^8$)$_2$,
  (D)N$R^8$C(O)$R^8$,
  (D)N$R^8$C(O)O$R^8$,
  (D)N$R^8$SO$_2$$R^8$, or
  (D)SO$R^8$,
$R^1$ is independently:
  hydrogen, CONH($C_1$–$C_8$ alkyl), $C_1$–$C_8$ alkyl, (D)phenyl, (D)$C_3$–$C_7$ cycloalkyl or oxo provided that oxo is not attached to the ring carbon adjacent to G;
$R^3$ is aryl;
  wherein the aryl is optionally substituted with one to three substituents selected from the group consisting of:
  cyano, halo, $C_1$–$C_8$ alkyl, (D)$C_3$–$C_7$ cycloalkyl, $C_1$–$C_4$ alkoxy, $C_1$–$C_4$ haloalkyl benzyloxy and $C_1$–$C_4$ haloalkyloxy;
$R^4$ is independently:
  hydrogen, $C_1$–$C_8$ alkyl, C(O)$R^8$, C(O)O$R^8$, $C_3$–$C_7$ cycloalkyl or (CH$_2$)$_n$O($C_1$–$C_8$ alkyl), wherein n is 2–8;
each $R^8$ is independently;
  hydrogen,
  aryl, wherein aryl being phenyl or naphthyl,
  $C_1$–$C_8$ alkyl,
  $C_1$–$C_8$ alkoxy, or (CH$_2$)$_n$C$_1$–C$_4$ haloalkyl, wherein n is 2–8;
each R$^{10}$ is independently:
hydrogen, (C$_1$–C$_8$)alkyl, C(O)C$_1$–C$_8$ alkyl, aryl, or C$_3$–C$_7$ cycloalkyl;
each R$^{11}$ is independently:
hydrogen,
C$_1$–C$_8$ alkyl,
(CH$_2$)$_n$N(R$^8$)$_2$,
wherein n is 2–8;
each R$^{12}$ is independently:
hydrogen,
C$_1$–C$_8$ alkyl,
(D)C$_3$–C$_7$ cycloalkyl,
(D)phenyl
C(O)C$_1$–C$_8$ alkyl,
C(O)phenyl,
SO$_2$C$_1$–C$_8$ alkyl or
SO$_2$-phenyl;
D is a bond or —(CH$_2$)$_n$—;
n is 0–8;
p is 0–4; and
q is 0–1.

2. The compound of claim 1, wherein the 5- or 6-membered carbocyclyl is cyclohexyl, cyclopentyl, cyclohexenyl, cyclopentenyl or phenyl.

3. The compound of claim 2, wherein R is independently at each occurrence: hydrogen, halo, hydroxy, C$_1$–C$_8$ alkyl, C$_1$–C$_8$ alkoxy, (D)C(O)R$^8$, (D)OC(O)R$^8$, (D)C(O)aryl, (D)C(O)C$_1$–C$_4$ alkoxy, (D)N(R$^8$)$_2$, (D)NR$^8$COR$^8$, (D)NR$_8$C(O)C$_1$–C$_4$ alkyl, or (D)NR$^8$SO$_2$R$^8$ where R$^8$ independently at each occurrence being hydrogen, C$_1$–C$_8$ alkyl, C$_1$–C$_8$ alkoxy or phenyl.

4. The compound of claim 3, wherein R$^3$ is phenyl optionally pain-substituted with chloro, flouro, bromo, iodo, methoxy, benzyloxy or methyl.

5. The compound of claim 4, wherein R$^3$ is phenyl para-substituted with chloro, fluoro or methoxy.

6. The compound of claim 5, wherein R$^4$ is hydrogen.

7. The compound of claim 6, wherein —(CH$_2$)$_n$-T is where * denotes a chiral carbon atom which has a R or S configuration.

8. The compound of claim 7, wherein L and L$^1$ are together oxo and the chiral carbon has R configuration.

9. A compound of formula III, (III)

or a pharmaceutically acceptable salts or stereoisomers thereof, wherein
R$_a$ is selected from the group consisting of:
C$_1$–C$_6$ alkoxy, NH$_2$, NH(C$_1$–C$_6$ alkyl), N(C$_1$–C$_6$ alkyl)$_2$, NHC(O)O(C$_1$–C$_6$ alkyl), N(CH$_3$)SO$_2$(C$_1$–C$_6$ alkyl), NHSO$_2$(C$_1$–C$_6$ alkyl), NHC(O)(C$_1$–C$_6$ alkyl), OC(O)(C$_1$–C$_6$ alkyl), OC(O)NH$_2$, C$_1$–C$_6$ alkoxy, and hydrogen;
R$_b$ is selected from the group consisting of:
halo, C$_1$–C$_6$ alkyl, N(C$_1$–C$_6$ alkyl)$_2$, C$_1$–C$_4$ haloalkyl, C$_1$–C$_6$ alkoxy and hydrogen; and
p is 0–4.

10. A compound of formula IV, (IV)

or a pharmaceutically acceptable salts or stereoisomers thereof, wherein
R$_a$ is selected from the group consisting of:
C$_1$–C$_6$ alkoxy, NH$_2$, NH(C$_1$–C$_6$ alkyl), N(C$_1$–C$_6$ alkyl)$_2$, NHC(O)O(C$_1$–C$_6$ alkyl), N(CH$_3$)SO$_2$(C$_1$–C$_6$ alkyl), NHSO$_2$(C$_1$–C$_6$ alkyl), NHC(O)(C$_1$–C$_6$ alkyl), OC(O)(C$_1$–C$_6$ alkyl), OC(O)NH$_2$, C$_1$–C$_6$ alkoxy, and hydrogen;
R$_b$ is selected from the group consisting of:
halo, C$_1$–C$_6$ alkyl, N(C$_1$–C$_6$ alkyl)$_2$, C$_1$–C$_4$ haloalkyl, C$_1$–C$_6$ alkoxy and hydrogen; and
p is 0–4.

11. A compound selected from the group consisting of:

| Name of compound | Structure of compound |
|---|---|
| 1,2,3,4-tetrahydro-isoquinoline-3-carboxylic acid {1-(4-chlorobenzyl)-2-[4-(7-diethylamino-5,6,7,8-tetrahydro-naphthalen-1-yl)-piperazin-1-yl]-2-oxo-ethyl}-amide | 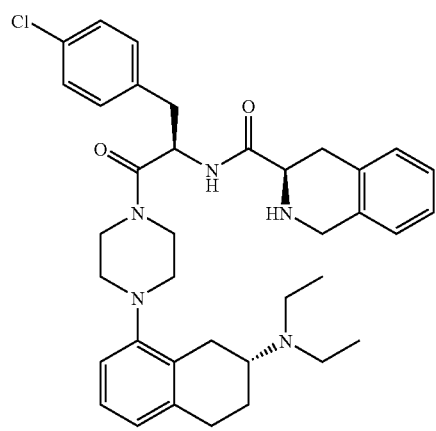 |
| 1,1-dimethyl-1,2,3,4-tetrahydro-isoquinoline-3-carboxylic acid {1-(4-chlorobenzyl)-2-[4-(7-diethylamino-5,6,7,8-tetrahydro-naphthalen-1-yl)-piperazin-1-yl]-2-oxo-ethyl}-amide | 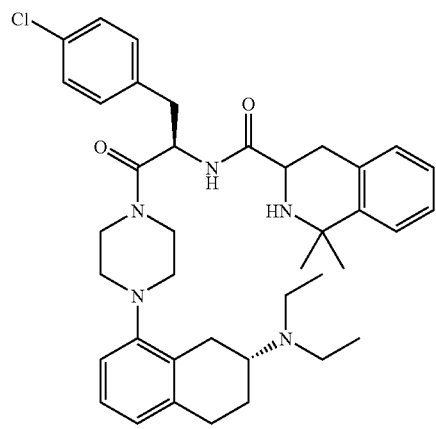<br>and its stereoisomers |
| N-{1-(4-chloro-benzyl)-2-[4-(7-diethylamino-5,6,7,8-tetrahydro-naphthalen-1-yl)-piperazin-1-yl]-2-oxo-ethyl}-2-(1,2,3,4-tetrahydro-isoquinolin-1-yl)-acetamide | 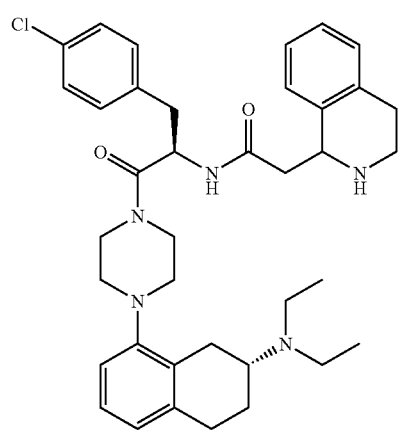<br>and its stereoisomers |

-continued

| Name of compound | Structure of compound |
|---|---|
| N-{1-(4-chloro-benzyl)-2-oxo-2-[4-(7-pyridin-1-yl-5,6,7,8-tetrahydro-naphthalen-1-yl)-piperazin-1-yl]-ethyl}-2-(2,3-dihydro-1H-isoindol-1-yl)-acetamide | 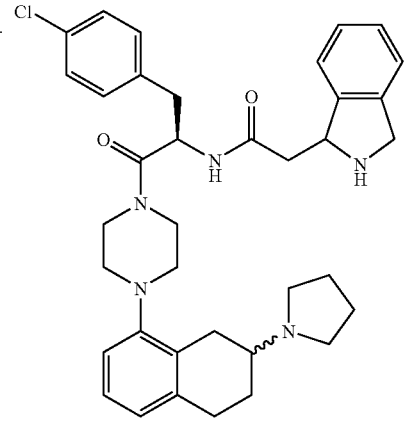 and its stereoisomers. |

12. A pharmaceutical composition which comprises a pharmaceutical carrier and at least one compound of formula I or its pharmaceutically acceptable salts or stereoisomers thereof as recited in claim 1.

13. The pharmaceutical composition of claim 12, which comprises a second active ingredient selected from the group consisting of: an insulin sensitizer, insulin mimetic, sulfonylurea, alpha-glucosidase inhibitor, HMG-CoA reductase inhibitor, sequestrant cholesterol lowering agent, beta 3 adrenergic receptor agonist, neuropeptide Y antagonist, phosphodiester V inhibitor, and an alpha 2 adrenergic receptor antagonist.

14. A process of making a pharmaceutical composition comprising a compound of formula I or its pharmaceutically acceptable salt or stereoisomers thereof as recited in claim 1 and a pharmaceutically acceptable carrier.

15. A method of treating obesity in a mammal in need of treatment thereof comprising the administration of a therapeutically effective amount of the compound of formula I as recited in claim 1.

16. A process for preparing a compound of formula I:

(I)

or a pharmaceutically acceptable salts or stereoisomers thereof, wherein

—CLL$^1$-(CH$_2$)$_n$-T is:

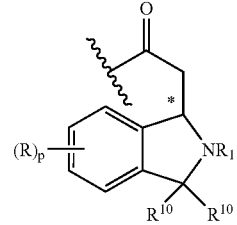

wherein R$_1$ is hydrogen, C$_1$–C$_8$ alkyl, Boc, CBZ, FMOC, phenyl or (C$_1$–C$_8$ alkyl)phenyl;

Q represents a moiety;

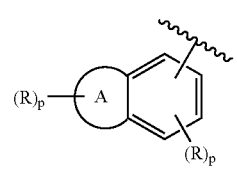

G is N;

is a 5- or 6-membered carbocyclyl wherein the carbocyclyl being saturated, partially saturated or aromatic ring, and the carbocyclyl being optionally substituted with one to three substituents independently selected from R;

R is independently:
  hydrogen,
  hydroxy,
  halo,
  $C_1$–$C_8$ alkyl,
  $C_1$–$C_8$ alkoxy,
  $C_1$–$C_4$ haloalkyl,
  (D)C(O)$R^8$,
  $C_1$–$C_8$ alkyl-N($R^8$)$_2$,
  (D)OCO$R^8$,
  (D)OC(O)N($R^8$)$_2$,
  (D)N($R^8$)$_2$,
  (D)$NR^8$C(O)$R^8$,
  (D)$NR^8$C(O)O$R^8$,
  (D)$NR^8SO_2R^8$, or
  (D)SO$R^8$,
$R^1$ is independently:
  hydrogen, CONH($C_1$–$C_8$ alkyl), $C_1$–$C_8$ alkyl, (D)phenyl, (D)$C_3$–$C_7$ cycloalkyl or oxo, provided that oxo is not attached to the ring carbon adjacent to G;
$R^2$ is independently:
  hydrogen,
  $C_1$–$C_8$ alkyl,
  $C_3$–$C_7$ cycloalkyl,
  C(O)$NH_2$,
  C(O)O($C_1$–$C_6$ alkyl),
  C(O)($CH_2$)$_n$N($C_1$–$C_6$ alkyl)$_2$,
  C(O)-phenyl,
  $SO_2$($C_1$–$C_6$ alkyl),
  $SO_2$N($C_1$–$C_6$ alkyl)$_2$,
  $SO_2$-phenyl or
  C(O)($C_1$–$C_6$ alkyl);
$R^3$ is aryl optionally substituted with one to three substituents selected from the group consisting of:
  cyano, halo, $C_1$–$C_8$ alkyl, (D)$C_3$–$C_7$ cycloalkyl, $C_1$–$C_4$ alkoxy, $C_1$–$C_4$ haloalkyl and $C_1$–$C_4$ haloalkyloxy;
$R^4$ is independently:
  hydrogen, $C_1$–$C_8$ alkyl, C(O)$R^8$, C(O)O$R^8$, $C_3$–$C_7$ cycloalkyl or ($CH_2$)$_n$O($C_1$–$C_8$ alkyl), wherein n is 2–8;
each $R^8$ is independently:
  hydrogen,
  aryl, wherein aryl being phenyl or naphthyl,
  $C_1$–$C_8$ alkyl,
  $C_1$–$C_4$ alkoxy, or
  ($CH_2$)$_n$$C_1$–$C_4$ haloalkyl, wherein n is 2–8;
each $R^{10}$ is independently:
  hydrogen, ($C_1$–$C_8$)alkyl, C(O)$C_1$–$C_8$ alkyl, aryl, or $C_3$–$C_7$ cycloalkyl;
D is a bond or —($CH_2$)$_n$—;
n is 0–8;
p is 0–4; and
q is 0–1;
comprising the steps of:
a) reacting a compound having a structural formula 1,

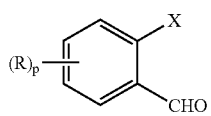
(1)

with $CH_2CH$=$C(O)OR^a$ wherein $R^a$ is hydrogen or $C_1$–$C_8$ alkyl and X is halo, in the presence of a catalyst and a base in a suitable organic solvent to give the compound of formula 2,

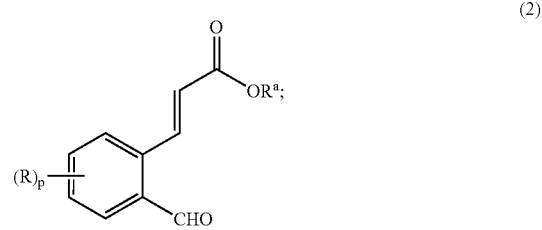
(2)

b) reductively aminating the compound of formula 2 in the presence of amine in an acidic condition to give a compound of formula 3,

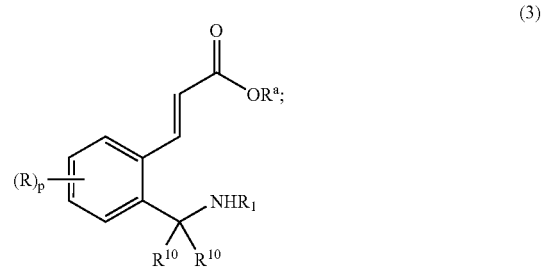
(3)

c) cyclizing the compound of formula 3 by Michael addition to give a compound of formula 4 or stereoisomers thereof,

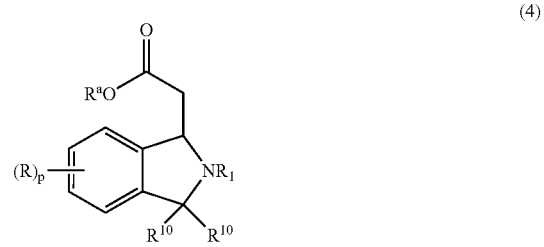
(4)

d) coupling the compound of formula 4 or stereoisomers thereof, wherein $R^a$ of compound 4 is H, with a compound of formula 5,

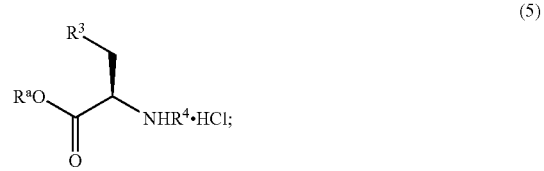
(5)

wherein $R^a$ of compound 5 is $C_1$–$C_8$ alkyl, to give a compound of formula 6;

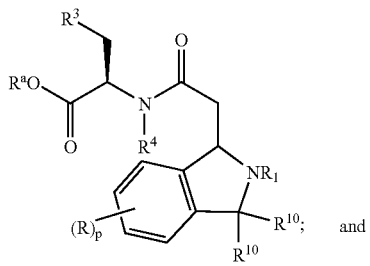

e) coupling the compound of formula 6, wherein $R^a$ is H, with a compound having a structural,

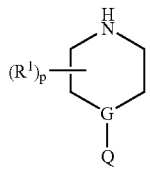

to afford the compound of formula 1.

17. The process of claim 16, wherein X for

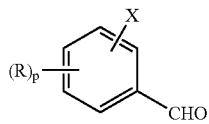

in Step (a) is 2-Br.

18. The process of claim 17, wherein $CH_2CH=C(O)OR$ in Step (a) is methylacrylate.

19. The process of claim 18, wherein the catalyst in Step (a) is selected from the group consisting of: $Pd(Ph_3P)_2Cl_2$, $Pd(Pb_3P)_4Cl_2$, $Pd(Ph_3P)_4$, $Pd(Ph_3P)_2Cl_2/CuI$, $Pd(OAc)_2/Ph_3P-Bu_4NBr$, $Pd(Ph_3P)_4Cl_2/H_2$ and $Pd(OAc)_2/P(O-tol)_3$; and wherein the base in Step (a) is $NR_3$ wherein R is hydrogen or $C_1$–$C_8$ alkyl.

20. The process of claim 19, wherein the amine in Step (b) is selected from the group consisting of: benzylamine, alpha-methylbenzylamine and $BocNH_2$.

21. The process of claim 20, wherein the Step (b) further comprises reducing of intermediate imine compound in the presence of reducing agent, the reducing agent being selected from the group consisting of: $NaCNBH_3$, $Na(OAc)_3BH$, $NaBH_4/H+$, and a combination of $Et_3SiH$ and TFA in $CH_3CN$ Or $CH_2Cl_2$.

22. The process of claim 16, wherein the stereoisomer of compound of formula 4 in Step (c) is a compound of formula 4a.

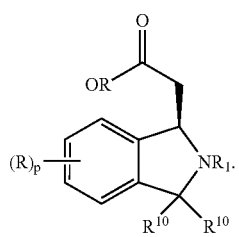

23. The process of claim 22, wherein the compound of formula 4a is prepared by asymmetric hydrogenation of a compound having structural formula,

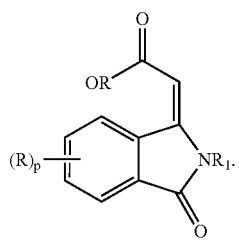

24. The process of claim 16, wherein the Michael addition in Step (c) is carried out in a basic workup condition.

25. The process of claim 16, wherein the Step (e) further comprises deprotecting or protecting of the compound of formula (6) at $NR_1$.

* * * * *